(12) United States Patent
Mikochik et al.

(10) Patent No.: US 11,845,754 B2
(45) Date of Patent: Dec. 19, 2023

(54) SUBSTITUTED PYRAZOLO[1,5-A]PYRIMIDINES FOR MODULATING CDK9 ACTIVITY

(71) Applicant: Kronos Bio, Inc., San Mateo, CA (US)

(72) Inventors: Peter Mikochik, Waltham, MA (US); Joseph Vacca, Telford, PA (US); David Freeman, Waltham, MA (US); Andrew S. Tasker, Simi Valley, CA (US)

(73) Assignee: Kronos Bio, Inc., San Mateo, CA (US)

( * ) Notice: Subject to any disclaimer, the term of this patent is extended or adjusted under 35 U.S.C. 154(b) by 62 days.

(21) Appl. No.: 17/476,237

(22) Filed: Sep. 15, 2021

(65) Prior Publication Data

US 2022/0002305 A1   Jan. 6, 2022

Related U.S. Application Data

(62) Division of application No. 16/667,027, filed on Oct. 29, 2019, now Pat. No. 11,155,560.

(60) Provisional application No. 62/910,058, filed on Oct. 3, 2019, provisional application No. 62/884,993, filed on Aug. 9, 2019, provisional application No. 62/752,635, filed on Oct. 30, 2018.

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ........................... A61K 31/519; C07D 487/04
USPC ........................................ 514/259.3; 544/263
See application file for complete search history.

(56) References Cited

U.S. PATENT DOCUMENTS

| | | | |
|---|---|---|---|
| 5,389,632 A | 2/1995 | Bru-Magniez et al. | |
| 6,372,743 B1 | 4/2002 | Darrow et al. | |
| 7,119,200 B2 | 10/2006 | Guzi et al. | |
| 7,161,003 B1 | 1/2007 | Guzi et al. | |
| 7,196,078 B2 | 3/2007 | Guzi et al. | |
| 7,205,308 B2 | 4/2007 | Guzi et al. | |
| 7,304,068 B2 | 12/2007 | Gudmundsson et al. | |
| 7,645,762 B2 | 1/2010 | Paruch et al. | |
| 7,662,826 B2 | 2/2010 | Seno et al. | |
| 7,741,318 B2 | 6/2010 | Clasby et al. | |
| 8,188,097 B2 | 5/2012 | Moritani et al. | |
| 8,211,854 B2 | 7/2012 | Guzi et al. | |
| 8,815,874 B2 | 8/2014 | Yamamoto et al. | |
| 8,957,077 B2 | 2/2015 | Cox et al. | |
| 8,963,976 B2 | 3/2015 | Kawanishi et al. | |
| 9,370,517 B2 | 6/2016 | Barfacker et al. | |
| 9,777,006 B2 | 10/2017 | Guilford | |
| 9,828,381 B2 | 11/2017 | Faghih et al. | |
| 2001/0007867 A1 | 7/2001 | Chen | |
| 2004/0038993 A1 | 2/2004 | Shipps et al. | |
| 2006/0205743 A1 | 9/2006 | Kataoka et al. | |
| 2007/0060595 A1 | 3/2007 | Yoshizawa et al. | |
| 2007/0082900 A1 | 4/2007 | Guzi et al. | |
| 2007/0275963 A1 | 11/2007 | Guzi et al. | |
| 2009/0137574 A1 | 5/2009 | Kampen et al. | |
| 2010/0317607 A1 | 12/2010 | Wynne et al. | |
| 2011/0244465 A1 | 10/2011 | Harvey et al. | |
| 2011/0294781 A1 | 12/2011 | Yamamoto et al. | |
| 2014/0303149 A1 | 10/2014 | Arora et al. | |
| 2017/0145018 A1 | 5/2017 | Wenglowsky et al. | |
| 2017/0174692 A1 | 6/2017 | Marineau et al. | |
| 2017/0175200 A1 | 6/2017 | Lyden et al. | |
| 2018/0057497 A1 | 3/2018 | Samajdar et al. | |
| 2018/0258092 A9 | 9/2018 | Samajdar et al. | |
| 2018/0319801 A1 | 11/2018 | Gray et al. | |
| 2019/0031664 A1 | 1/2019 | Masse et al. | |

FOREIGN PATENT DOCUMENTS

| | | |
|---|---|---|
| EP | 0 714 898 A1 | 6/1996 |
| EP | 2608669 B1 | 10/2002 |
| EP | 1 780 212 A1 | 5/2008 |
| EP | 2585467 A1 | 5/2013 |
| EP | 2069348 B1 | 12/2015 |
| JP | 2002308879 A | 10/2002 |
| JP | 2005008581 A | 1/2005 |
| WO | WO 1998003510 A1 | 1/1998 |
| WO | WO 2001023388 A2 | 4/2001 |
| WO | WO 2003091256 A1 | 11/2003 |
| WO | WO 2004022561 A1 | 3/2004 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Gao et al., "Overcoming Resistance to the THZ Series of Covalent Transcriptional CDK Inhibitors," Cell Chemical Biology, Feb. 2018, vol. 25 (2) pp. 135-142, Elsevier Inc.
Gregory, et al., "CDK9 inhibition by dinaciclib potently suppresses Mcl-1 to induce durable apoptotic responses in aggressive MYC-driven B-cell lymphoma in vivo," Leukemia, 2015, vol. 29, pp. 1437-1441, Nature Publishing Group.

(Continued)

*Primary Examiner* — Douglas M Willis
(74) *Attorney, Agent, or Firm* — Michael Blessent; Bozicevic, Field & Francis LLP

(57) ABSTRACT

Inhibitors of CDK9 that are pyrazolo[1,5-a]pyrimidine derivatives and salts thereof, corresponding to formula (I):

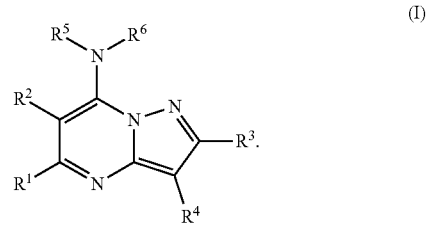

11 Claims, No Drawings

(56) References Cited

FOREIGN PATENT DOCUMENTS

| | | | |
|---|---|---|---|
| WO | WO 2004026229 A2 | 4/2004 | |
| WO | WO 2004087707 A1 | 10/2004 | |
| WO | WO 2005063756 A1 | 7/2005 | |
| WO | WO 2006087120 A2 | 8/2006 | |
| WO | WO 2007/044449 A2 | 4/2007 | |
| WO | WO 2008/045267 A2 | 4/2008 | |
| WO | WO 2008/130569 | 10/2008 | |
| WO | WO 2008151304 | 1/2010 | |
| WO | WO 2011042798 A1 | 4/2011 | |
| WO | WO 2011068667 A1 | 6/2011 | |
| WO | WO 2011105628 A1 | 9/2011 | |
| WO | WO 2012170827 A3 | 5/2012 | |
| WO | WO 2013123169 A1 | 8/2013 | |
| WO | WO 2013130943 A1 | 9/2013 | |
| WO | WO 2014075168 A1 | 5/2014 | |
| WO | WO 2004089471 A2 | 10/2014 | |
| WO | WO 2015124941 A1 | 8/2015 | |
| WO | WO 2016/201370 A1 | 12/2016 | |
| WO | WO 2017059080 A1 | 4/2017 | |
| WO | WO 2017069270 A1 | 4/2017 | |
| WO | WO 2017180499 A2 | 10/2017 | |
| WO | WO 2019/023654 A2 | 1/2019 | |
| WO | WO-2020092314 A1 * | 5/2020 | ........... A61K 31/519 |

OTHER PUBLICATIONS

Heathcote, et al., "A Novel Pyrazolo[1,5-a]pyrimidine Is a Potent Inhibitor of Cyclin-Dependent Protein Kinases, 1, 2 and 9, Which Demonstrates Antitumor Effects in Human Tumor Xenografts Following Oral Administration," Journal of Medicinal Chemistry, 2010, vol. 53, pp. 8508-8522, ACS publications.

International Search Report and Written Opinion dated Feb. 7, 2020 in International Application No. PCT/US2019/058482.

Smail, et al., "Medicinal attributes of pyrazolo[1,5-a]pyrimidine based scaffold derivatives targeting kinases as anticancer agents," Future Journal of Pharmaceutical Sciences, Dec. 2016, vol. 2(2), pp. 1-33, Elsevier.

Kaliszczak, et al., "Development of cyclin-dependent kinase inhibitor devoid of ABC transporter-dependent drug resistance," British Journal of Cancer, 2013, pp. 1-12, Cancer Research UK.

Krystof, et al., "Perspective of Cyclin-dependent kinase 9 (CDK9) as a Drug Target," Current Pharmaceutical Design, 2012, vol. 18, pp. 2883-2890, Bentham Science Publishers.

Lucking, et al., "Identification of Atuveciclib (BAY 1143572), the First Highly Selective, Clinical PTEFb,CDK9 Inhibitor for the Treatment of Cancer," Chemical Medicinal Chemistry, 2017, vol. 12, pp. 1776-1793, Wiley Online Library, The Authors.

Morales, et al., "Overview of CDK9 as a target in cancer research," Cell Cycle, 2016, vol. 15(4), pp. 519-527, Taylor & Francis Group.

Parry, et al., "Dinaciclib (SCH 727965), a Novel and Potent Cyclin-Dependent Kinase Inhibitor," Molecular Cancer Therapetuics, 2010, vol. 9(8), pp. 2344-2353, AACR, American Associate for Cancer Research.

Paruch, et al., "Discovery of Dinaciclib (SCH 727965) A Potent and Selective Inhibitor of Cyclin-Dependent Kinases," Medical Chemistry Letters, 2010, vol. 1, pp. 204-208, American Chemical Society.

Pillipson, et al., "Discovery and Sar of novel pyrazolop1,5-a]pyrimidines as inhibitors of CDK9," Bioorganic & Medicinal Chemistry, Oct. 2015, vol. 23(19) pp. 1-55, Elsevier.

Sonawane, et al., "Cyclin Depdendent Kinase 9 Inhibitors for Cancer Therapy," Journal of Medicinal Chemistry, 2016, vol. 59, pp. 8667-8684, American Chemical Society.

Wilson, et al., "Design, synthesis and biological evaluation of 6-pyridlmethylaminopurines as CDK inhibitors," Bioorganic and Medicinal Chemistry, Nov. 2011, vol. 19(22), pp. 6949-6965, Elsevier.

Kosugi, T. et al. Mitogen-Activated Protein Kinase-Activated Protein Kinase 2 (MAPKAP-K2) as an Antiinflammatory Target: Discovery and in Vivo Activity of Selective Pyrazolo[1,5-a]pyrimidine Inhibitors Using a Focused Library and Structure-Based Optimization Approach. *Journal of Medicinal Chemistry*, Jul. 2, 2012, vol. 55, No. 15, pp. 6700-6715. Table 5 compounds 51-52.

Tomomi Kosugi et al.: "Mitogen-Activated Protein Kinase-Activated Protein Kinase 2 (MAPKAP-K2) as an Anti-Inflammatory Target: Discovery and in Vivo Activity of Selective Pyrazolo [1,5-a] pyrimidine Inhibitors Using a Focused Library and Structure-Based Optimization Approach", Journal of Medicine Chemistry, vol. 55, No. 15, Aug. 9, 2012 (Aug. 9, 2012), pp. 6700-6715.

Novinson T et a.: "Synthesis and antifungal properties of certain 7-alkylaminopyrazolo (1,5-a)pyrimidines", Journal of Medicinal Chemistry, American Chemical Society, US, vol. 20, No. 2, Jan. 1, 1977 (Jan. 1, 1977), pp. 296-299.

* cited by examiner

SUBSTITUTED PYRAZOLO[1,5-A]PYRIMIDINES FOR MODULATING CDK9 ACTIVITY

CROSS-REFERENCE TO RELATED APPLICATIONS

This application is a divisional application of U.S. application Ser. No. 16/667,027, which was filed on Oct. 29, 2019 and which issued as U.S. Pat. No. 11,155,560, and which claims the benefit of U.S. Provisional Patent Application Nos. 62/752,635, 62/884,993, and 62/910,058; filed on Oct. 30, 2018, Aug. 9, 2019, and Oct. 3, 2019, respectively, which are hereby incorporated by reference in their entirety.

FIELD

The disclosure provides for compounds that modulate the activity of cyclin-dependent kinase 9 (CDK9), pharmaceutical compositions comprising such compounds, and methods of using the compounds and/or pharmaceutical compositions for treatment, amelioration, and/or prevention of diseases arising from the activity of CDK9, e.g., hyperproliferative diseases, virally induced infectious diseases, and cardiovascular diseases.

BACKGROUND

The cyclin-dependent kinase (CDK) family of proteins are key regulators of the cell cycle and gene transcription. The cell cycle is a regulatory cellular mechanism for the timing of cell growth and division. The cell cycle is a multipronged process that directs cellular proliferation through a series of checkpoints that correct for DNA damage, genetic derangements, and other errors. Nonhuman Primates in Biomedical Research (Second Edition, 2012). Each stage is controlled by a combination of cyclins and CDKs, where the CDKs phosphorylate a specific set of cyclins to trigger entry into the next stage of the cell cycle. Cell Cycle Merri Lynn Casem B A, PhD, in Case Studies in Cell Biology, 2016. Accumulation of cyclin proteins through regulation of cyclin mRNA transcription function as "biological switches" to turn CDKs on and off and move the cell from one stage to the next. [Id.].

CDKs 1, 2, 3, 4 and 6 regulate time of the cell division cycle while CDK 7 and CDK 9 regulate the activity of transcription through regulation of RNA polymerase II via phosphorylation of its carboxy terminal domain. Lucking, et al., Chem Med Chem 2017, 12, 1776-1793.

CDK9 controls the transcriptional activity of key oncogenic proteins such as AR, MYC, MCL-1, and BCL-2 and stimulates pro-inflammatory transcription factors such as NFkB and STAT3. Gregory et al., Leukemia. 2015 June; 29(6): 1437-1441; Kryštof, et al., Curr Pharm Des. 2012 July; 18(20): 2883-2890. CDK9 forms a heterodimer with one of four cyclin partners (cyclin T1, cyclin K, cyclin T2a, or cyclin T2b) called positive transcription elongation factor (PTEFb). RNA polymerase II pauses mRNA transcription after 20-40 nucleotides along the DNA template due to interaction of negative elongation factors which serve as a major regulatory control mechanism for transcription of rapidly induced genes. PTEFb overcomes pausing of RNA polymerase II by phosphorylation of the carboxy terminal domain of RNA polymerase II, and inactivation of negative elongation factors. Compounds targeting CDK9 and PTEFb are currently undergoing clinical study. The enzymatic activity of CDK9 is important for stimulating transcription elongation of most protein coding genes. Kryštof, et al., Curr Pharm Des. 2012 July; 18(20): 2883-2890.

A number of CDK inhibitors with heterocyclic core structures have been developed. For example, purine scaffolds have been the source of CDK inhibitors developed for treating cancer, including seliciclib (Cyclacel Pharmaceuticals, Inc) and other purine derivatives. S. C. Wilson et al., Bioorg & Med Chem 2011 November; 19(22): 6949-6965. Besides CDK9 these purine derivatives also target CDK7 and CDK2, whereas CDK2 inhibition causes safety and toxicity concerns. CDK9 inhibitors based on a triazine core have also been developed, e.g., Atuveciclib. Lucking et al., Chem Med Chem 2017, 12, 1776-1793. Unfortunately, treatment with CDK9 inhibitors remains relatively unsuccessful and involves many adverse effects. Morales et al., Cell Cycle 2016, vol. 15, no. 4, 519-527. Therefore, a need exists for new CDK9 inhibitors for treating diseases mediated by CDK9.

SUMMARY

In an embodiment, the disclosure provides for pyrazolo [1,5-a]pyrimidines, and derivatives thereof, that are inhibitors of CDK9.

In an embodiment, the disclosure provides for a compound of formula (I):

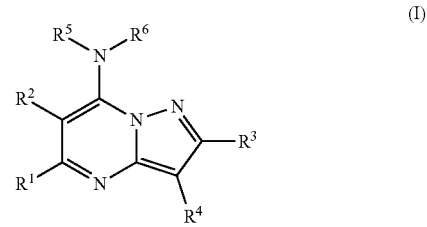

or a pharmaceutically acceptable salt thereof, wherein:
$R^1$ is C1-C6 alkyl, C3-C6 cycloalkyl, tetrahydrofuranyl, or tetrahydropyranyl, optionally substituted at any position with one or more of D, halo, $R^7CO_2R^8$, $CO_2R^8$, $CO_2H$, $R^7CO_2H$, $NH_2$, $NHR^8$, OH, $OR^8$, SH, $SR^8$, $NHCOR^8$, $NHSO_2R^8$, $SO_2NH_2$, $SO_2NHR^8$,
or $R^1$ is $NH_2$, $NHR^8$, OH, $OR^8$, $NHCOR^8$, $NHSO_2R^8$, $SO_2NH_2$, $SO_2NHR^8$,
or $R^1$ and $R^2$ together form a fused C5-C6 cycloaryl, optionally substituted at any position with one or more of D, halo, $NH_2$, $NHR^8$, $NR^7R^8$, OH, $OR^8$, SH, $SR^8$, $NHCOR^8$, $NHSO_2R^8$, $SO_2NH_2$, or $SO_2NHR^8$;
$R^2$, $R^3$, $R^4$ and $R^5$ are independently H, D, halo, or C1-C5 alkyl or C3-C6 cycloalkyl optionally substituted at any position with one or more of D, halo, $NH_2$, $NHR^8$, $NR^7R^8$, OH, $OR^8$, SH, $SR^8$, $NHCOR^8$, $NHSO_2R^8$, $SO_2NH_2$, or $SO_2NHR^8$,
or $R^3$ and $R^4$ together form a fused C5-C6 cycloaryl, optionally substituted at any position with one or more of D, halo, $NH_2$, $NHR^8$, $NR^7R^8$, OH, $OR^8$, SH, $SR^8$, $NHCOR^8$, $NHSO_2R^8$, $SO_2NH_2$, or $SO_2NHR^8$,
or $R^2$ and $R^5$ together form a fused C5-C6 cycloaryl, optionally substituted at any position with one or more of D, halo, $NH_2$, $NHR^8$, $NR^7R^8$, OH, $OR^8$, SH, $SR^8$, $NHCOR^8$, $NHSO_2R^8$, $SO_2NH_2$, or $SO_2NHR^8$;
$R^6$ is H or D;
$R^7$ is $(CH_2)_n$ wherein n is an integer from 1 to 6; and R[8] is C1-C6 alkyl or C3-C6 cycloalkyl, optionally substituted at any position with one or more of D, halo, OH, SH, or $NH_2$.

In another embodiment, in the compound or salt thereof of formula (I), R[1] is C1-C6 alkyl or C3-C6 cycloalkyl, optionally substituted at any position with $NH_2$, or R[1] is NHCOR[8]; R[2], R[3], R[4], and R[6] are H; R[5] is cyclobutyl, cyclopentyl, or cyclohexyl, optionally substituted at any position with D, $NH_2$, OH, NHR[8], OR[8], or combinations thereof; and R[8] is C1-C4 alkyl.

In another embodiment, in the compound or salt thereof of formula (I), R[1] is methyl, ethyl, isopropyl, sec-butyl, 3-pentyl, cyclopropyl, cyclopentyl, or $NHCOCH_3$; R[2], R[3], R[4], and R[6] are H; and R[5] is cyclobutyl, cyclopentyl, or cyclohexyl, optionally substituted at any position with $NH_2$.

The compound may be in the form of a composition including a pharmaceutically acceptable carrier.

In another embodiment, the disclosure provides for methods of treating, preventing, or ameliorating CDK9-mediated diseases such as hyperproliferative diseases (e.g., cancer), virally induced infectious diseases, and cardiovascular diseases, by administering an effective amount of a pyrazolo [1,5-a]pyrimidine derivative described herein to a subject in need thereof.

DETAILED DESCRIPTION

In an embodiment, a compound described herein capable of use in compositions or methods described herein comprises, consists of, or consists essentially of a compound of formula (I) or a salt thereof. In an aspect, the composition is formulated in a pharmaceutical composition or form.

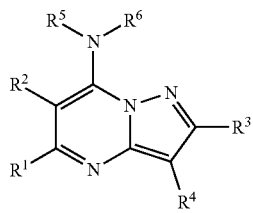

(I)

Any of the compounds described via formula (I) or shown as specific compounds may be a single stereoisomer or a mixture of possible stereoisomers. For example, if a single chiral carbon is present, the compound may be the (S) or (R) stereoisomer, with respect to the chiral carbon, or the compound may be a non-racemic mixture of (S) and (R) isomers, or the compound may be the (S) isomer alone or the (R) isomer alone. If the compound contains more than one chiral carbon, the compound may be a single diastereomer or a mixture of diastereomers.

By "salt" is meant a pharmaceutically acceptable salt, e.g., a hydrochloride salt. A "pharmaceutically acceptable salt" is a salt that retains the activity of the compound without significant adverse effects. Examples of pharmaceutically acceptable salts include salts of organic or inorganic acids, e.g., hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, and formic acid. The salt may contain one or more equivalents of acid per compound, i.e., the compound may be in the form of a dichloride salt.

The active compounds disclosed can also be in the form of their hydrates. The term "hydrate" includes, e.g., hemihydrate, monohydrate, dihydrate, trihydrate, and tetrahydrate.

The compounds of this disclosure may exhibit their natural isotopic abundances, or one or more of the atoms may be artificially enriched in a particular isotope having the same atomic number, but an atomic mass or mass number different from the atomic mass or mass number predominantly found in nature. The present disclosure includes all suitable isotopic variations of the compounds described herein.

"Alkyl" means branched and straight-chain saturated aliphatic hydrocarbons, and specifying the number of carbon atoms as in "C1-C6 alkyl" means all isomers thereof having 1, 2, 3, 4, 5, or 6 carbons in a linear or branched arrangement. Thus, "C1-C6 alkyl" includes methyl, ethyl, n-propyl, i-propyl, n-butyl, t-butyl, i-butyl, etc.

"Cycloalkyl" means cyclic saturated aliphatic hydrocarbons of the specified number of carbons.

"D" is deuterium.

"Halo" means a halogen substituent, e.g., F, Cl, or Br.

Examples of compounds of formula (I) include:

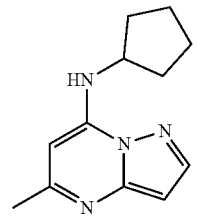

1

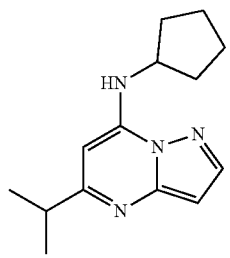

2

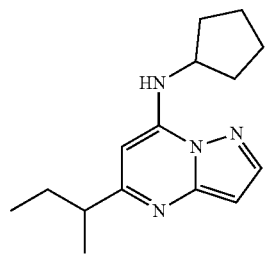

3

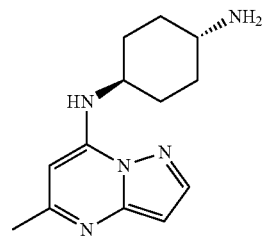

4

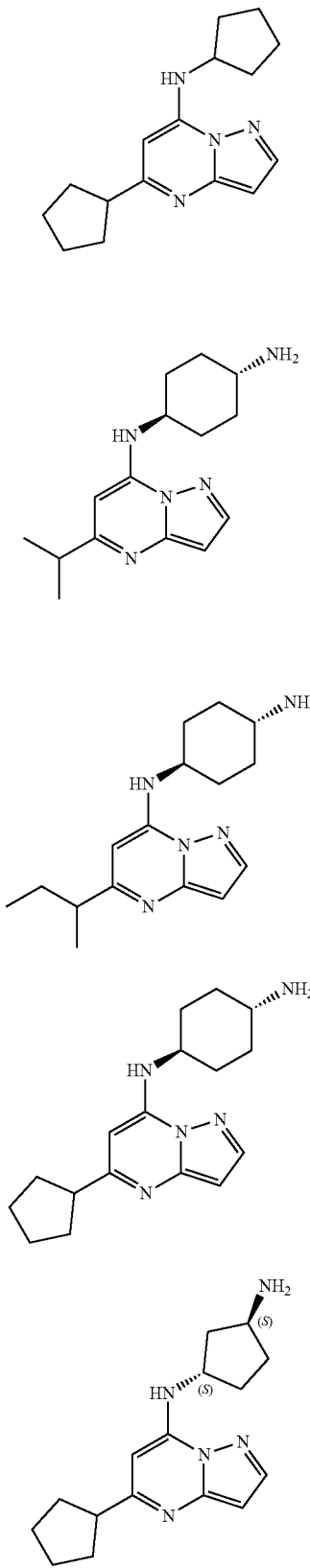
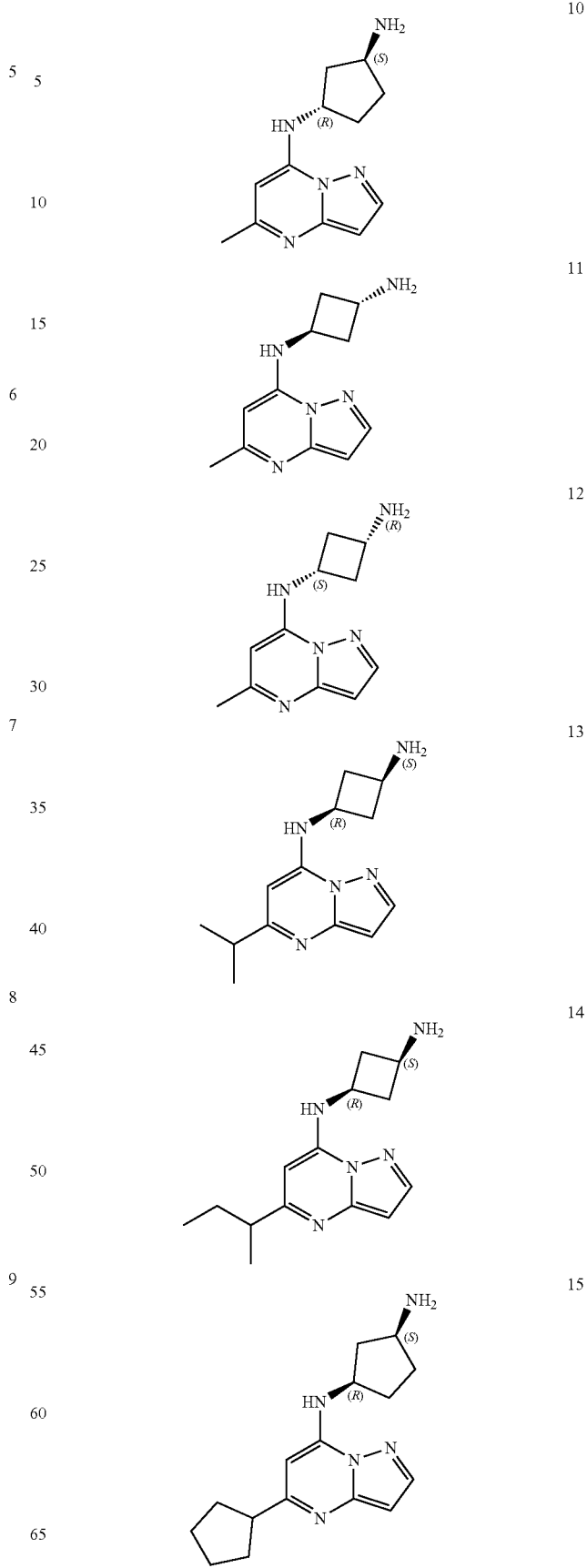

-continued
16
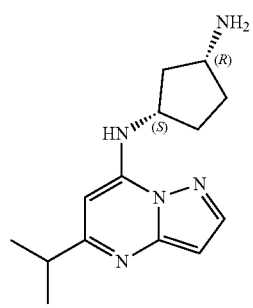
17
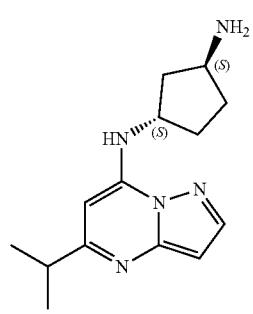
18
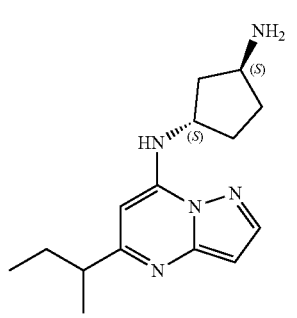
19
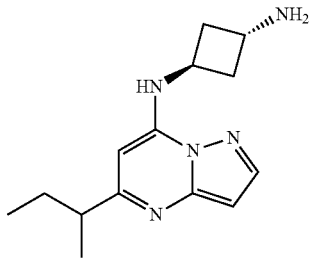
20
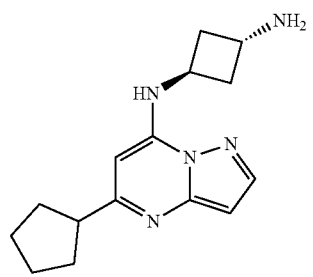
-continued
21
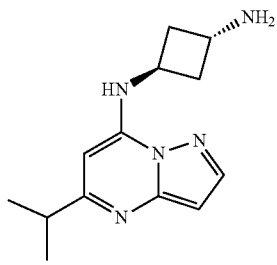
22
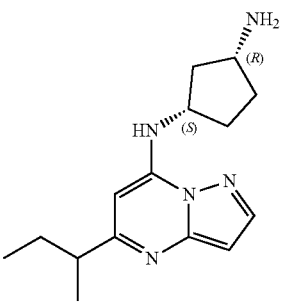
23
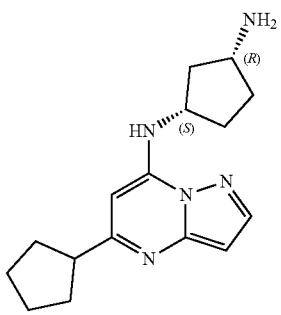
24
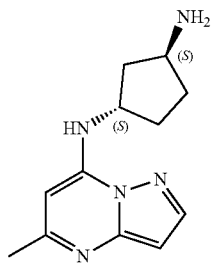
31
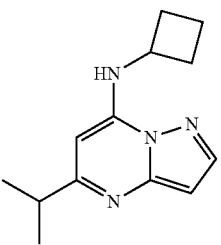

| | |
|---|---|
| 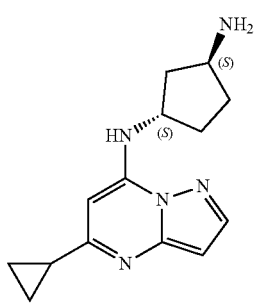 32 | 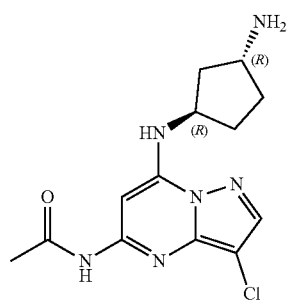 37 |
| 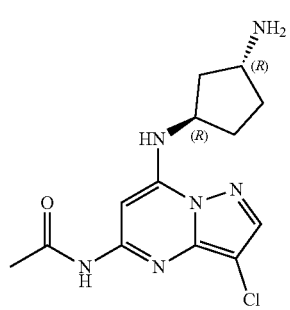 33 | 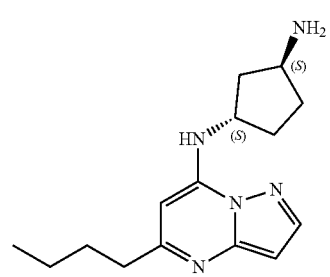 38 |
| 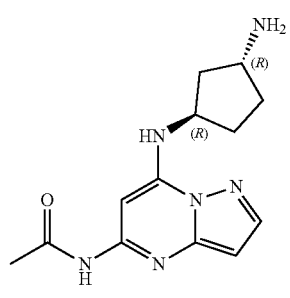 34 | 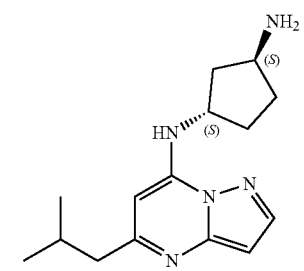 39 |
| 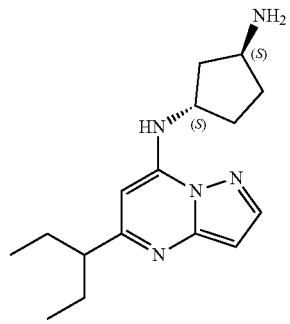 35 | 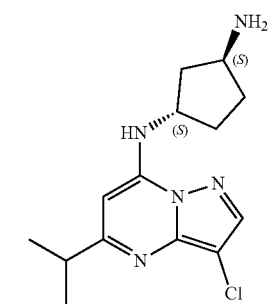 40 |
| 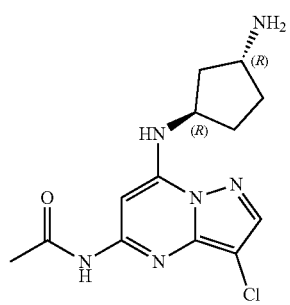 36 | 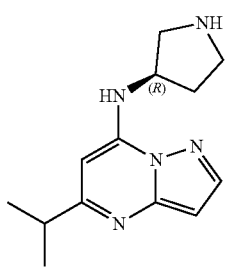 41 |

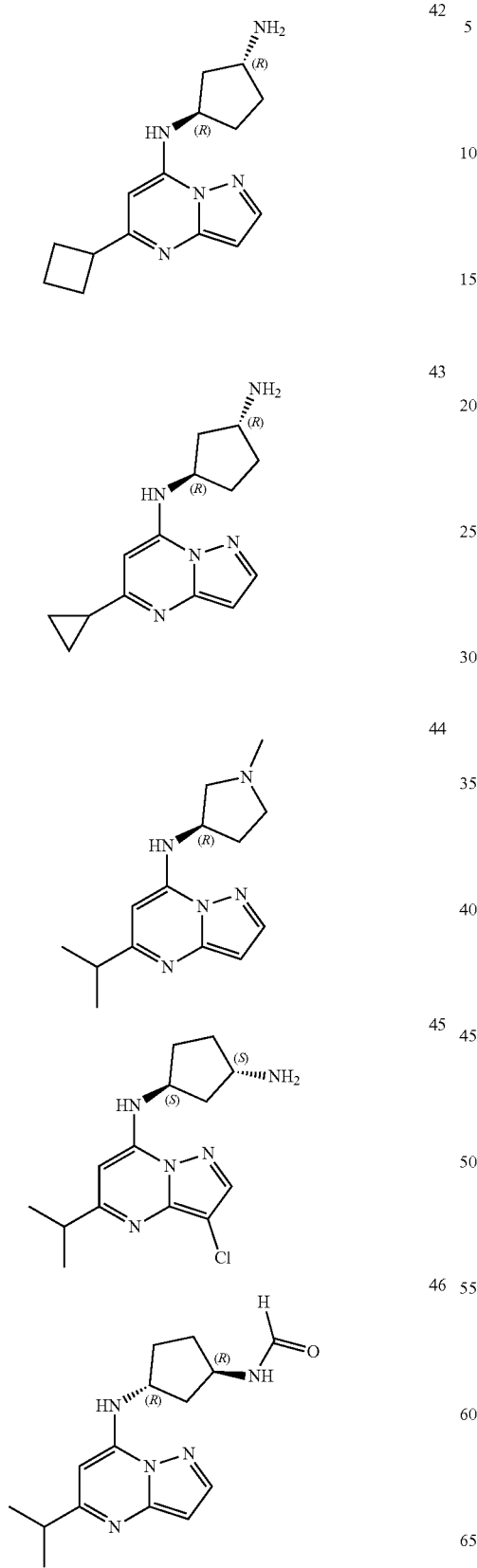
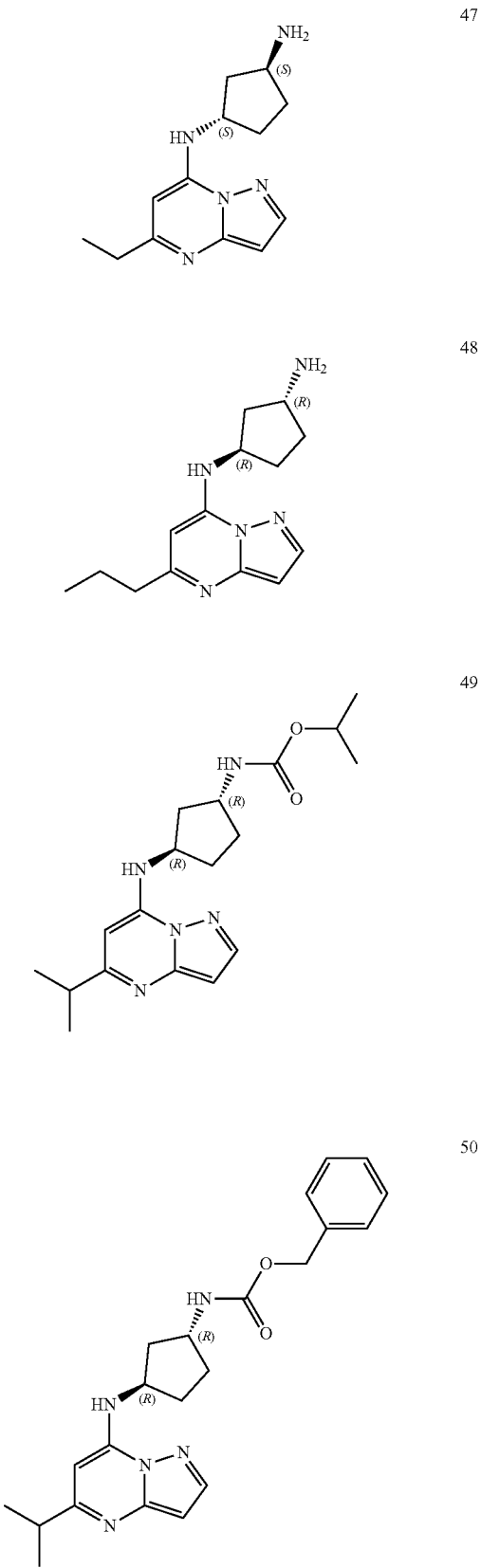

51 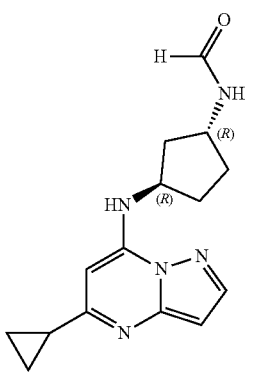
52 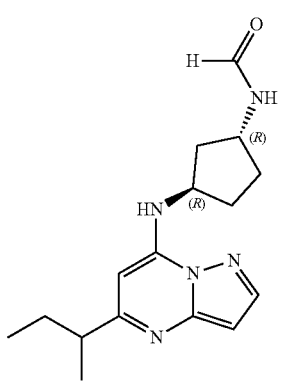
53 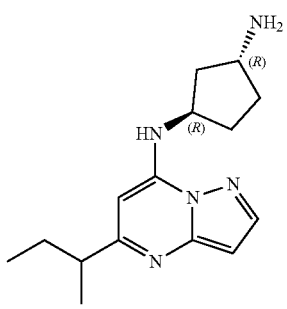
54 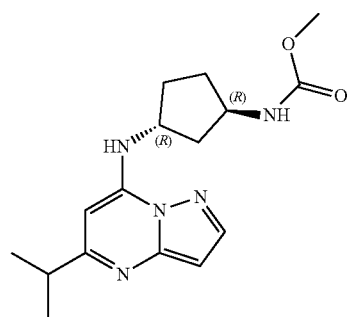
55 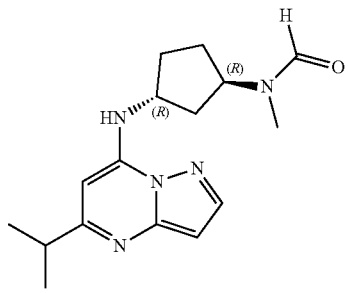
56 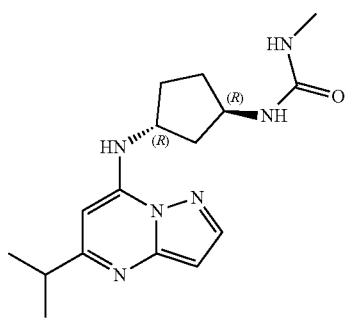
57 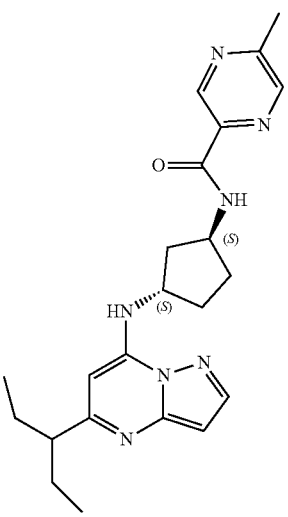
58 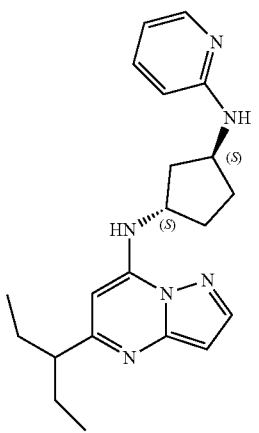

59
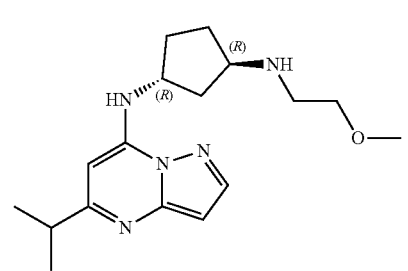
60
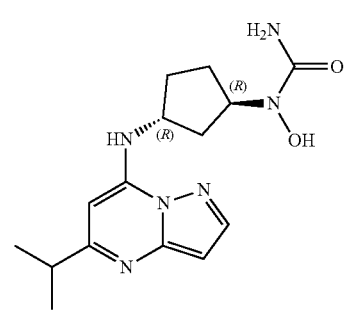
61
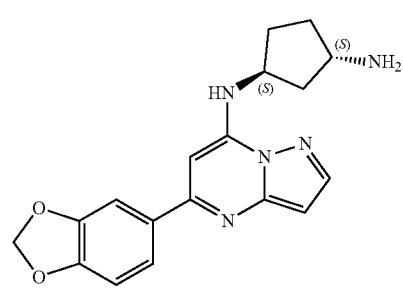
62
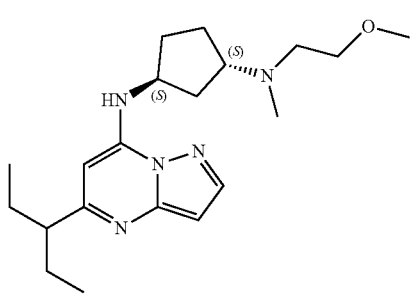
63
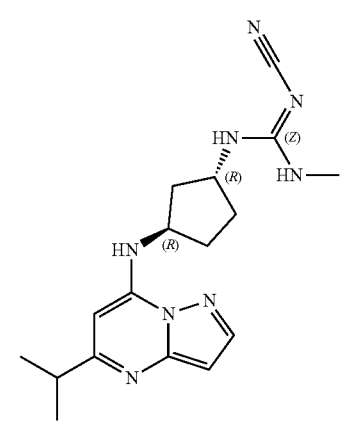
64
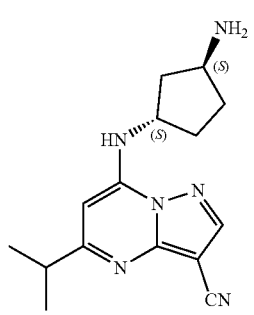
65
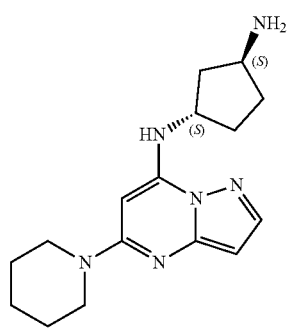
66
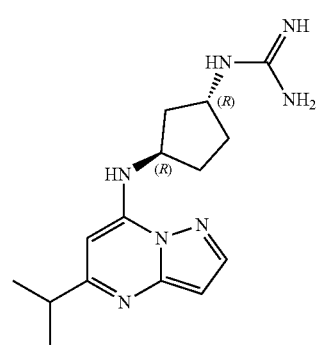
67
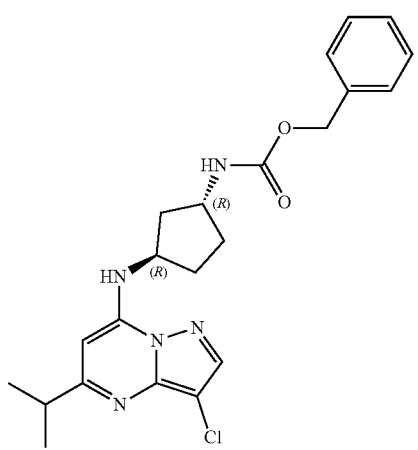

| 68 | 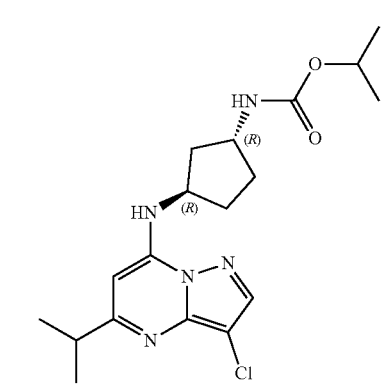 | 72 | 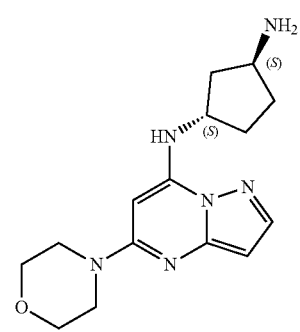 |
| 69 | 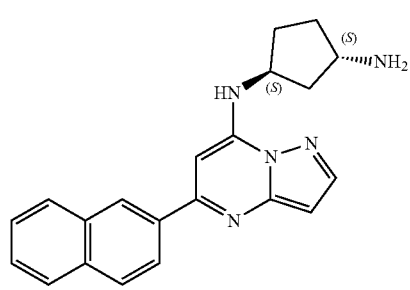 | 73 | 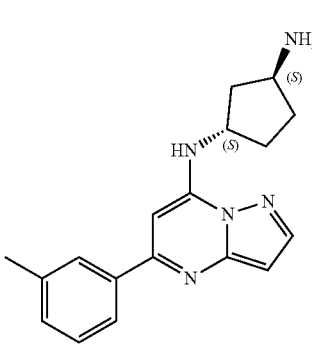 |
| 70 | 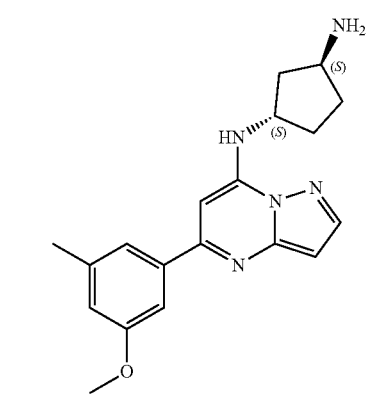 | 74 | 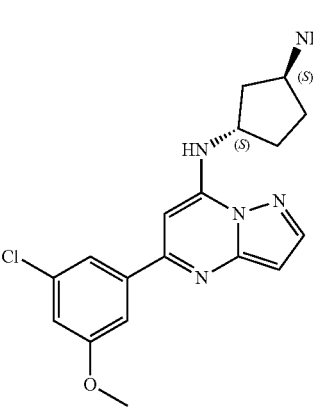 |
| 71 | 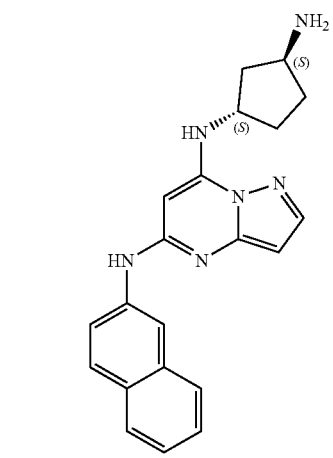 | 75 | 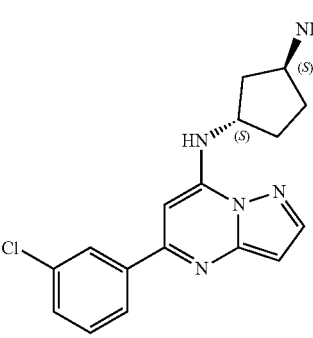 |

-continued
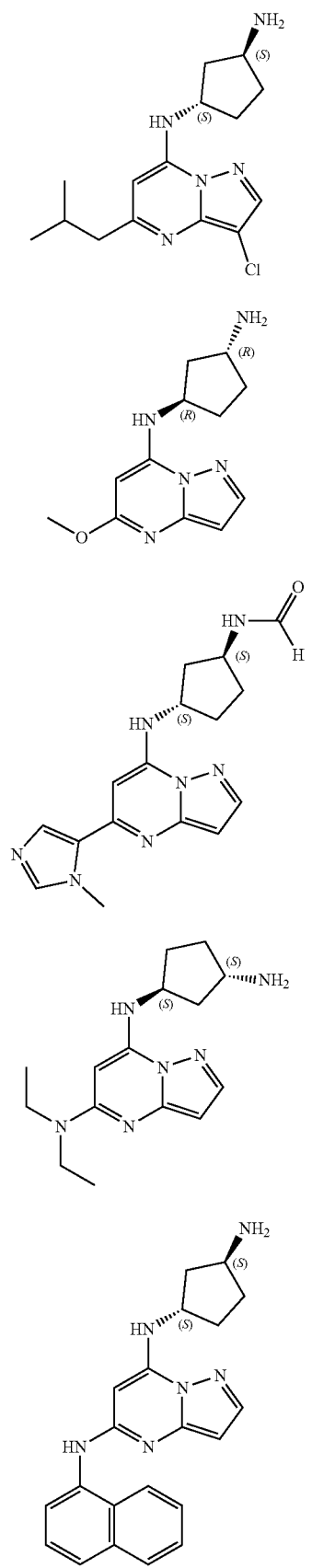
-continued
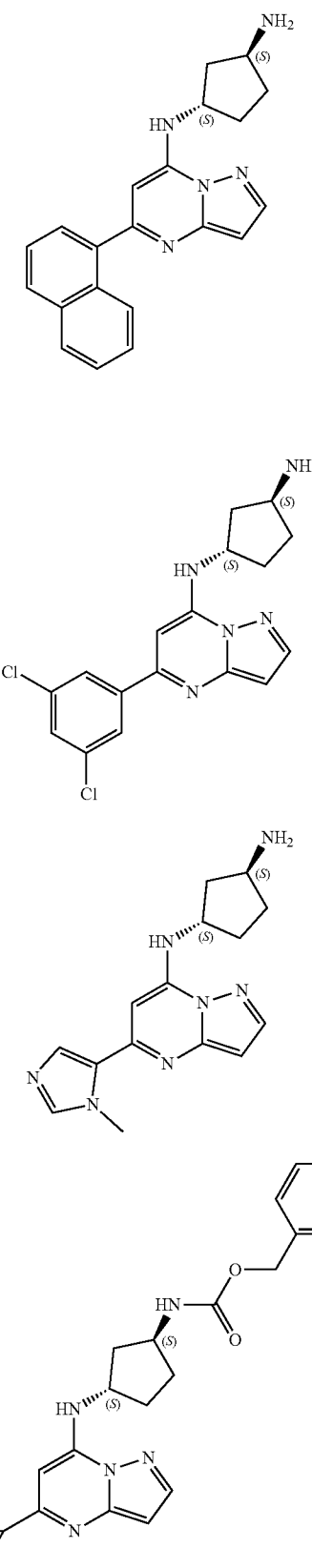

85
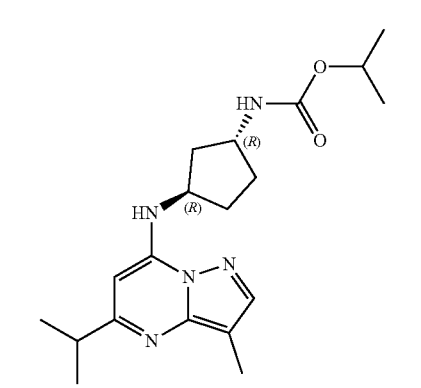
86
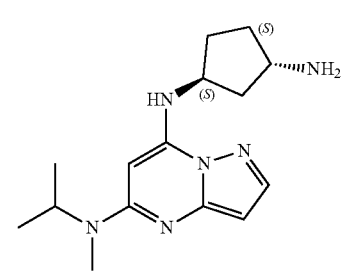
87
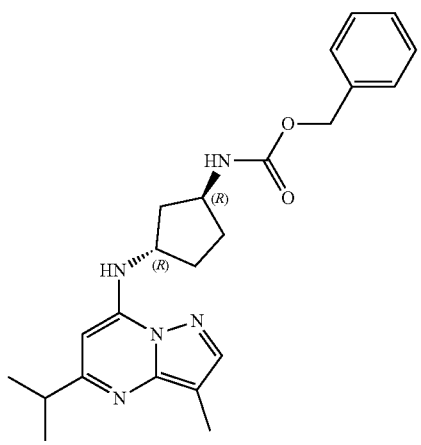
88
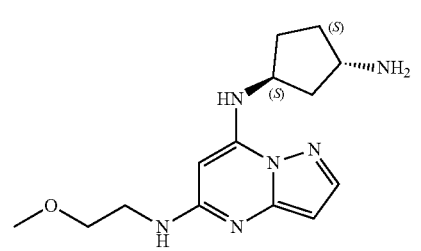
89
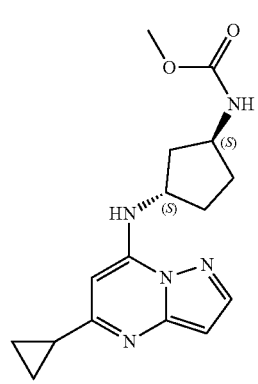
90
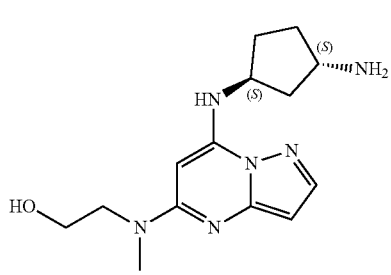
91
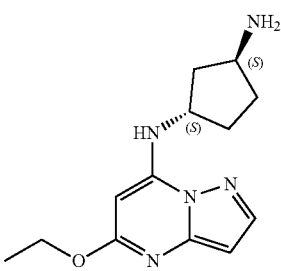
92
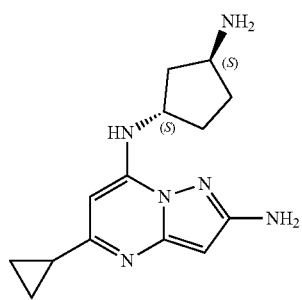
93
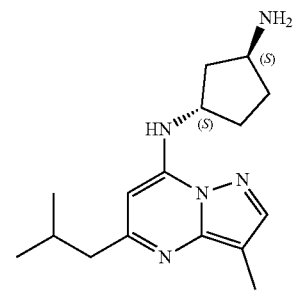

94
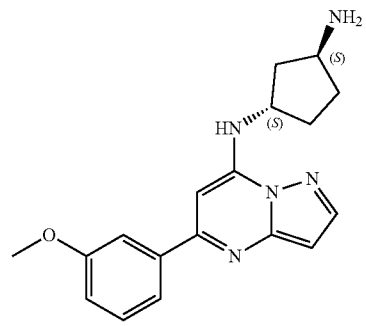
95
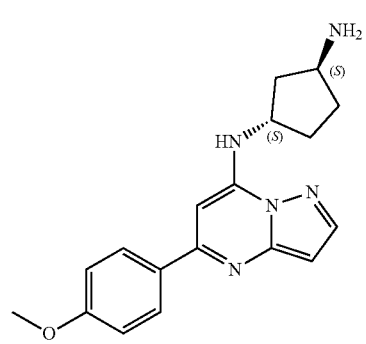
96
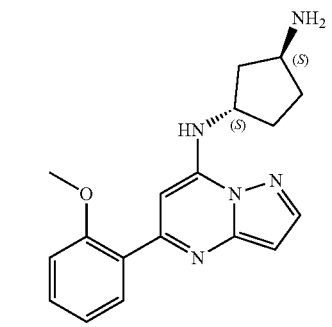
97
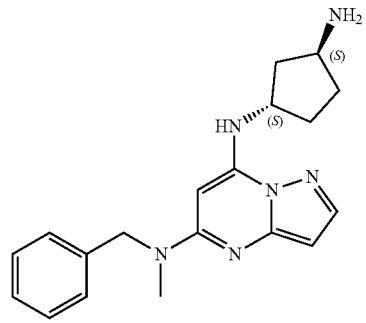
98
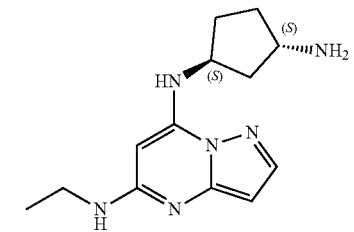
99
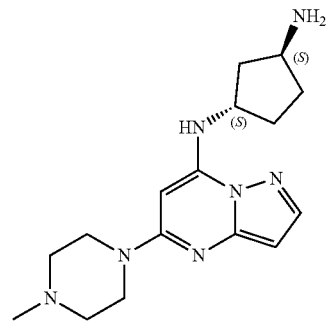
100
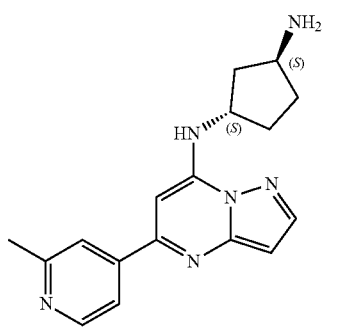
101
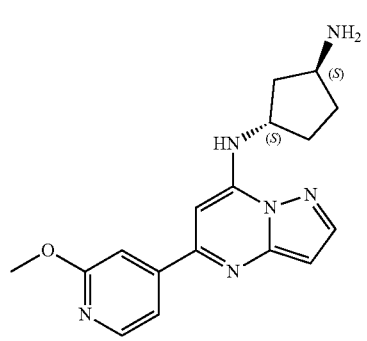
102
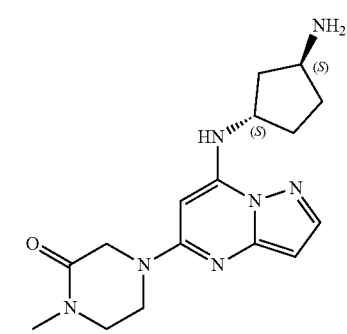
103
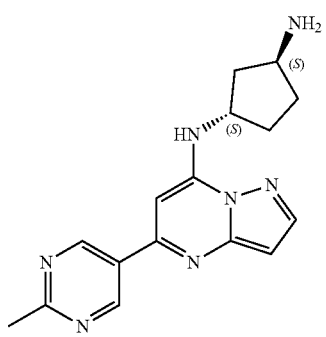

| | |
|---|---|
| 104 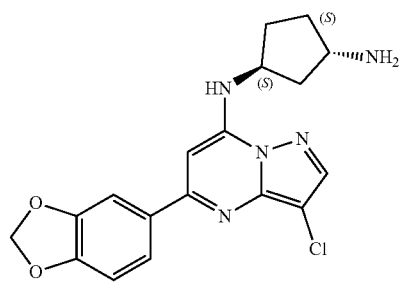 | 109 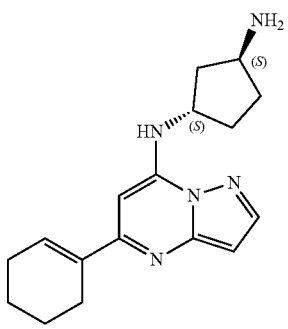 |
| 105 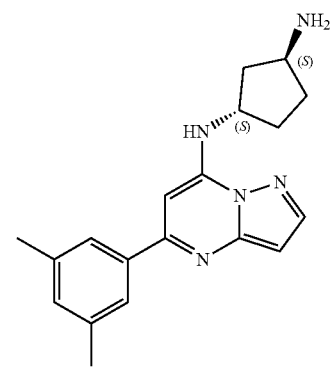 | 110 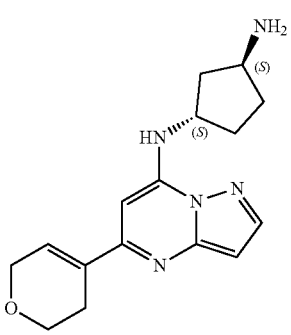 |
| 106 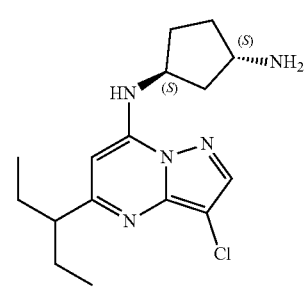 | 111 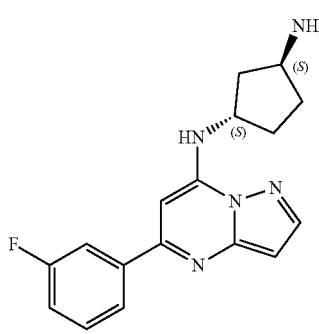 |
| 107 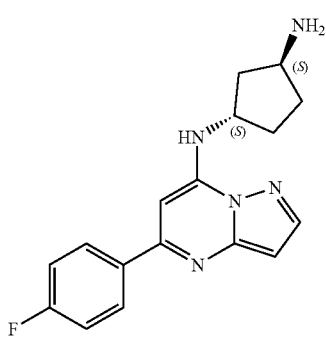 | 112 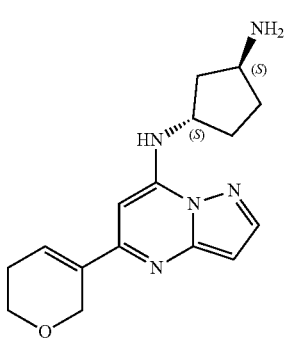 |
| 108 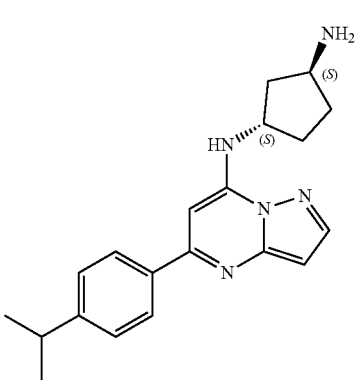 | |

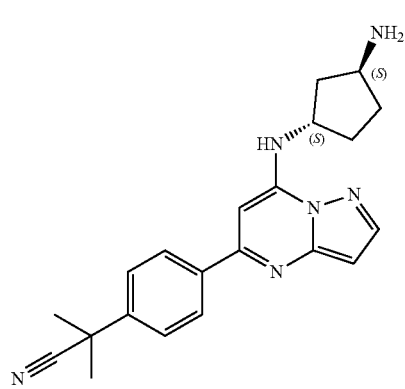 113
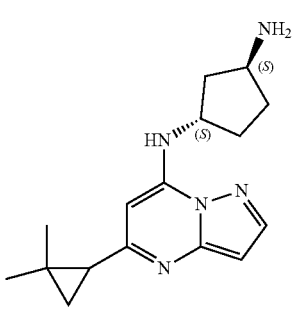 117
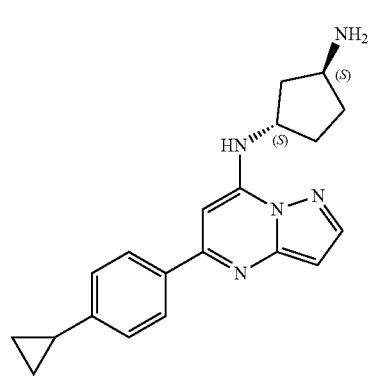 114
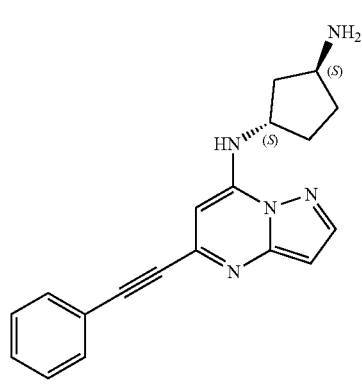 118
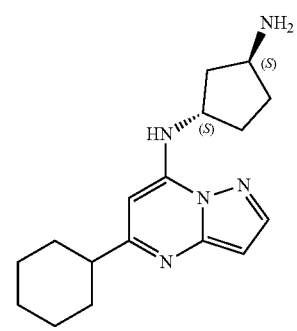 115
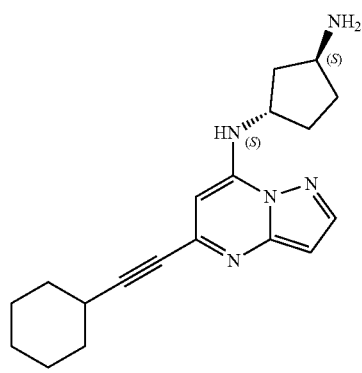 119
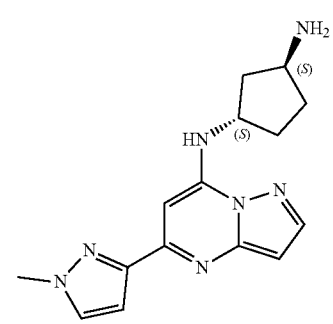 116
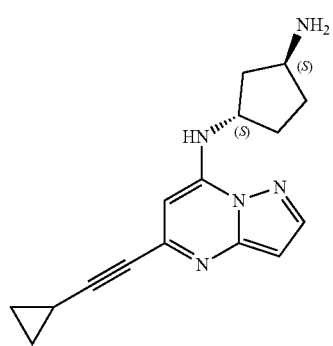 120

| 121 | 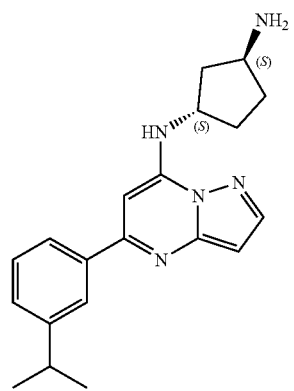 | 125 | 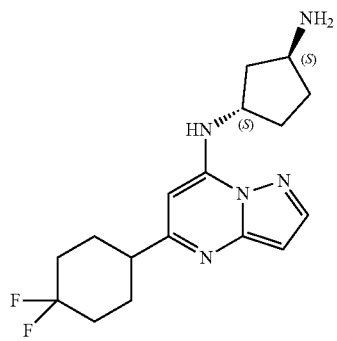 |
| 122 | 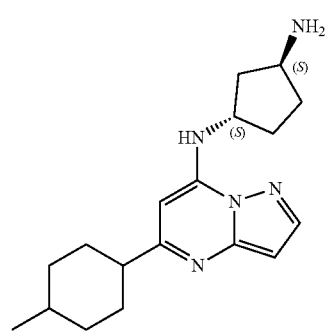 | 126 | 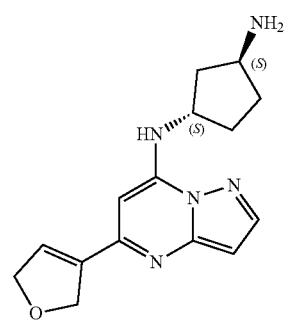 |
| | | 127 | 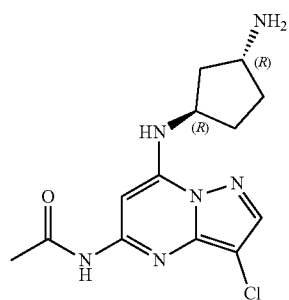 |
| 123 | 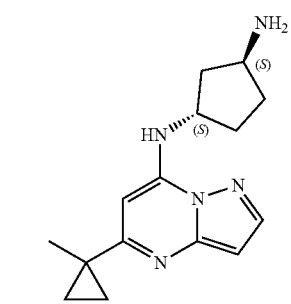 | 128 | 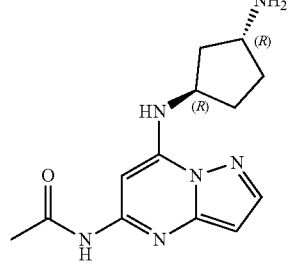 |
| 124 | 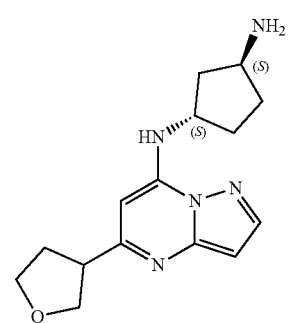 | 129 | 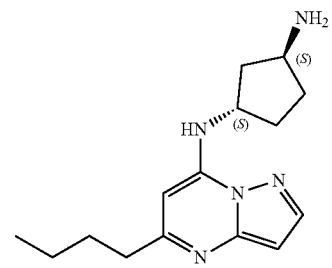 |

| | |
|---|---|
| 130 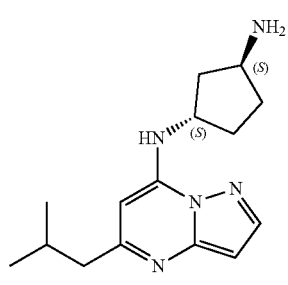 | 135 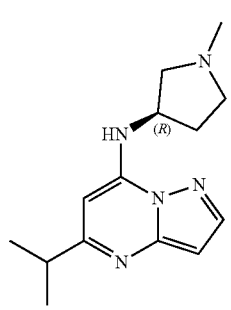 |
| 131 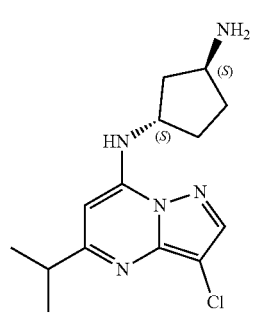 | 136 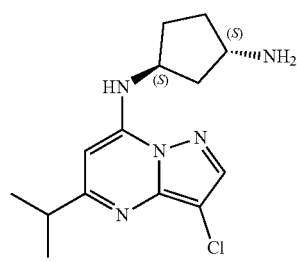 |
| 132 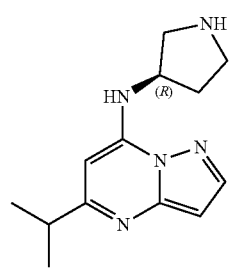 | 137 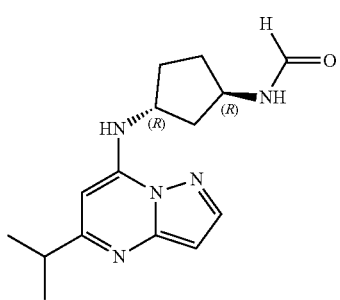 |
| 133 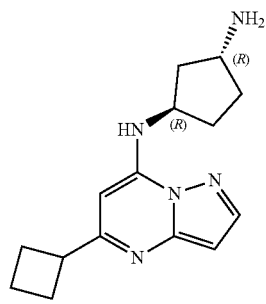 | 138 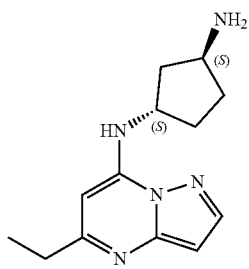 |
| 134 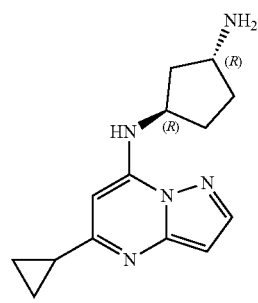 | 139 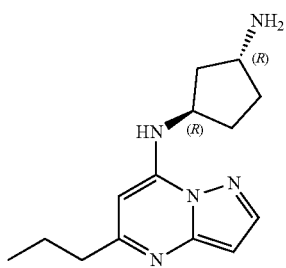 |

140 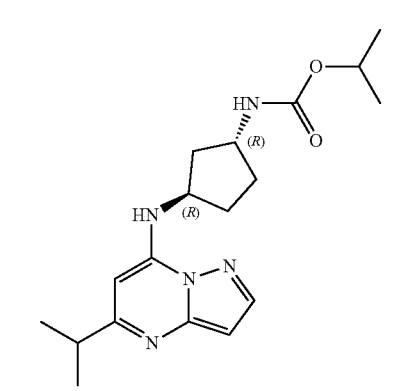
141 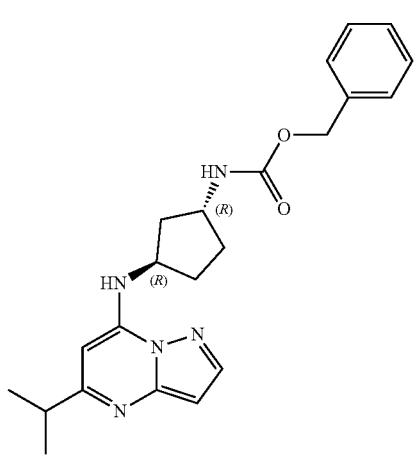
142 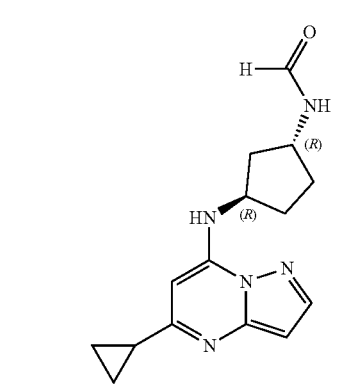
143 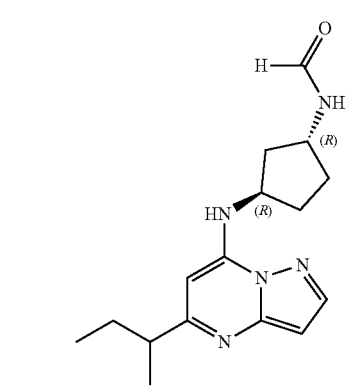
144 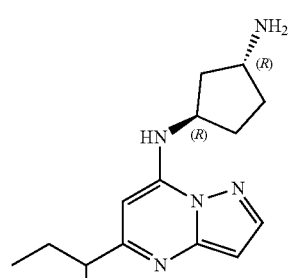
145 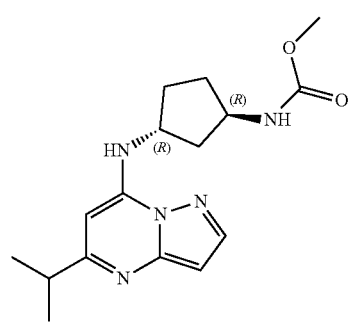
146 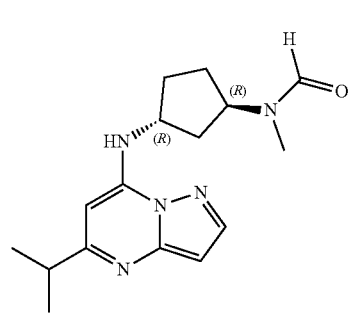
147 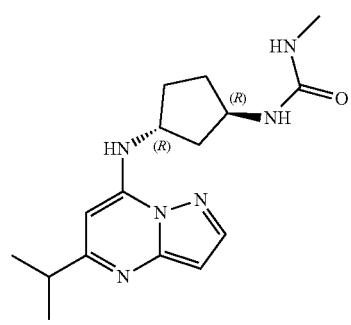

148 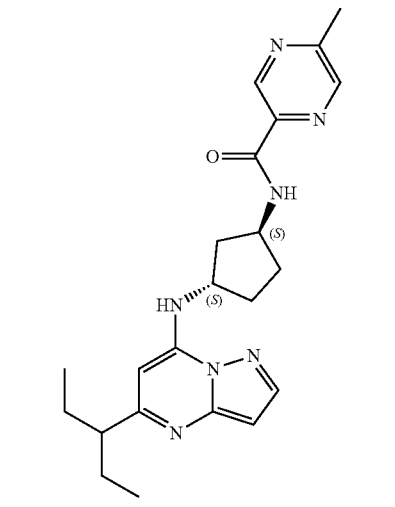
149 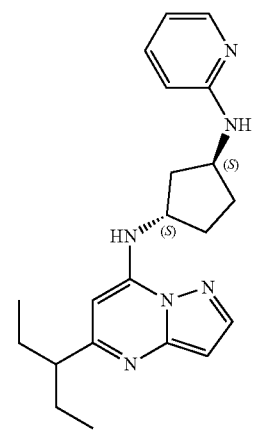
150 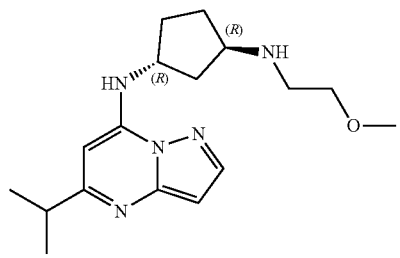
151 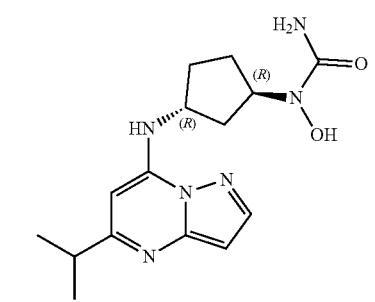
152 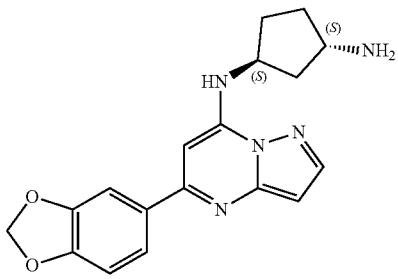
153 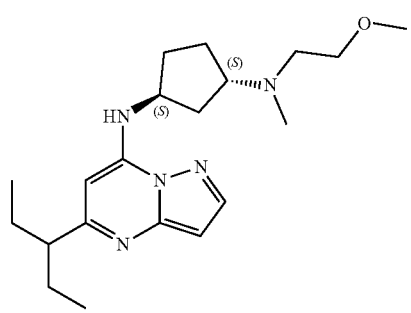
154 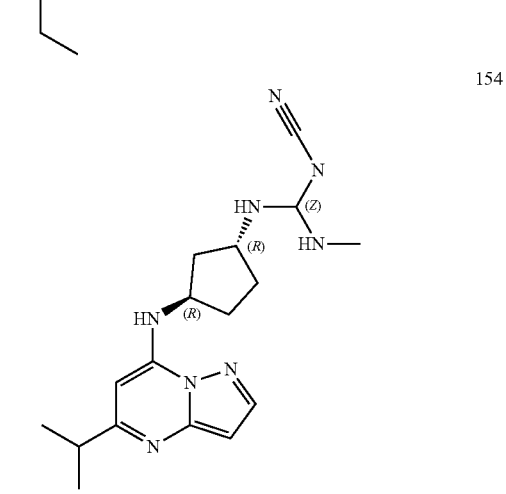
155 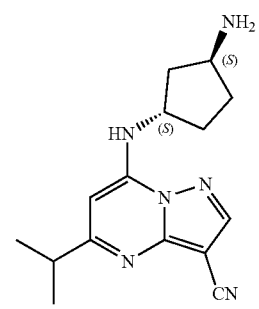
156 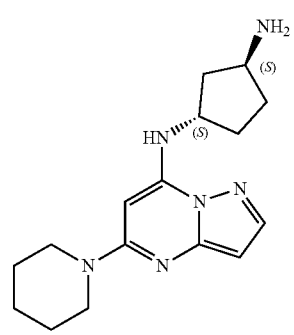

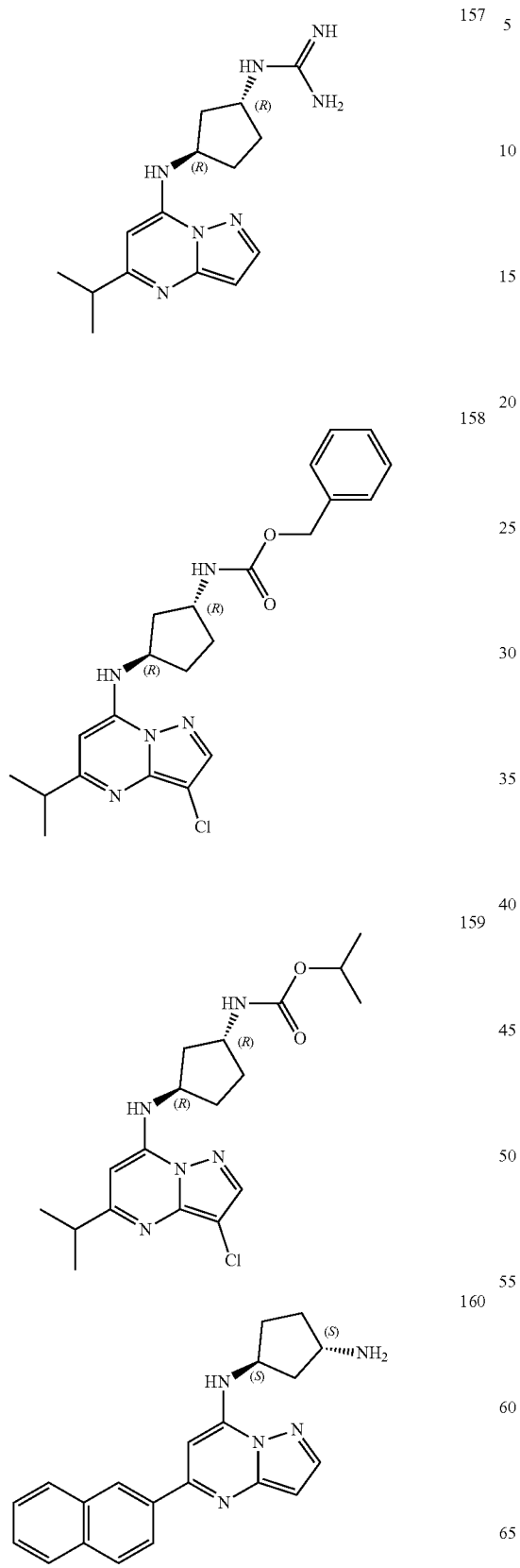
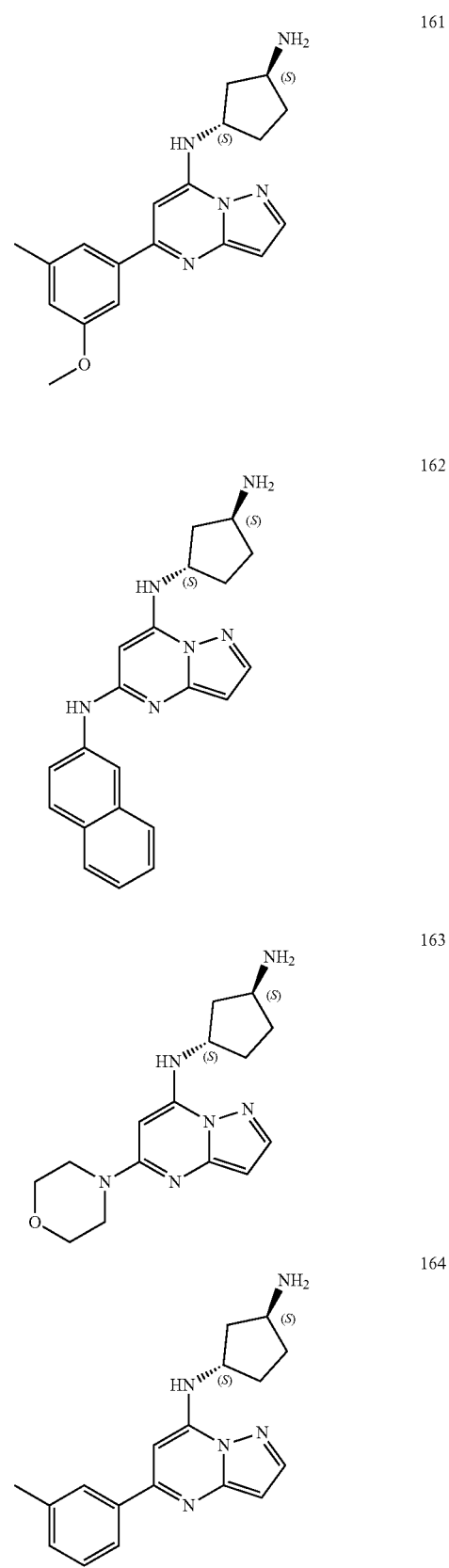

| 165 | 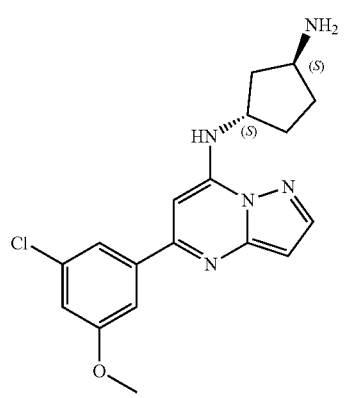 | 170 | 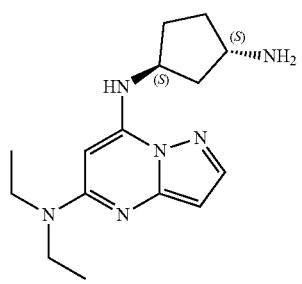 |
| --- | --- | --- | --- |
| 166 | 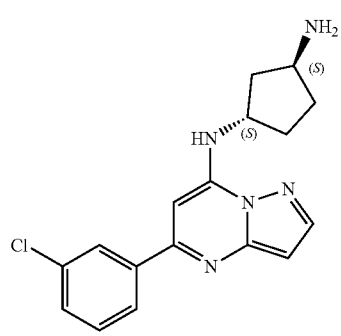 | 171 | 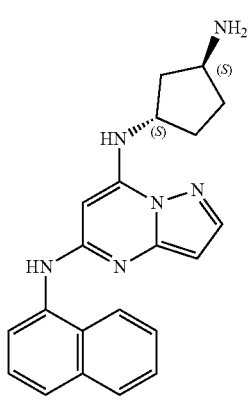 |
| 167 | 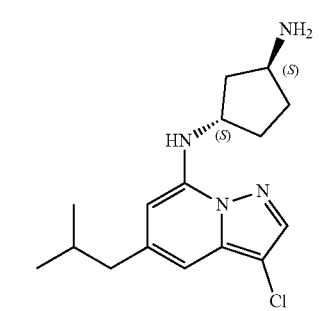 | 172 | 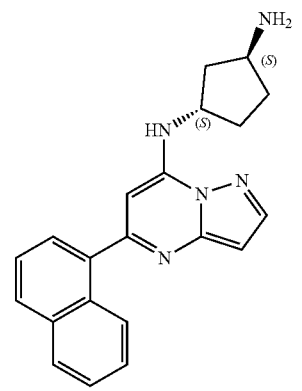 |
| 168 | 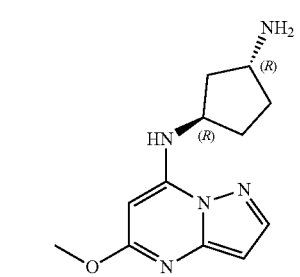 | 173 | 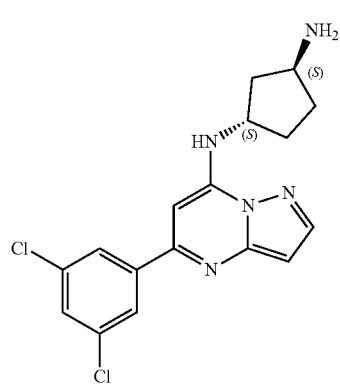 |
| 169 | 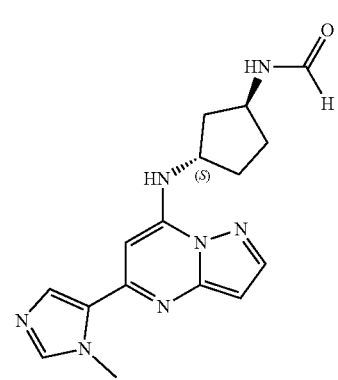 | | |

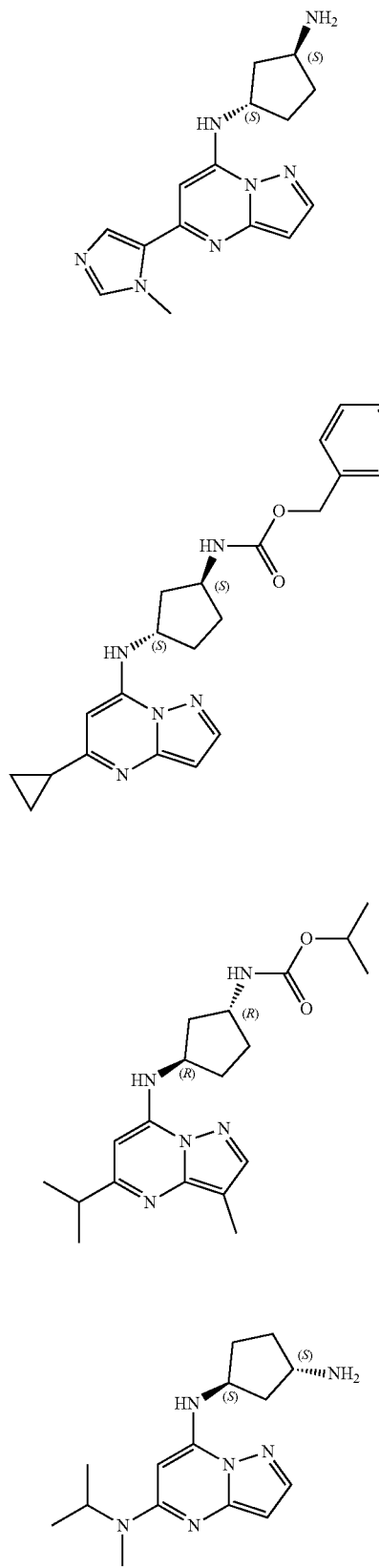
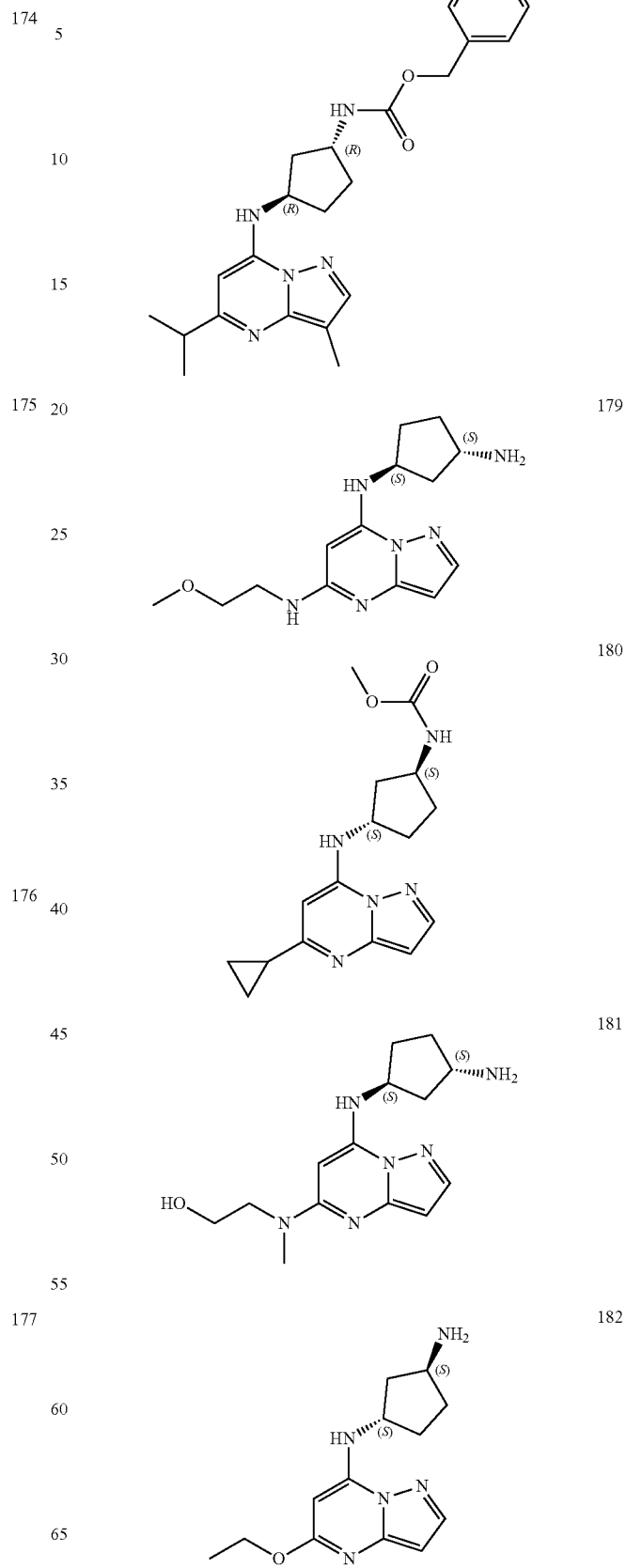

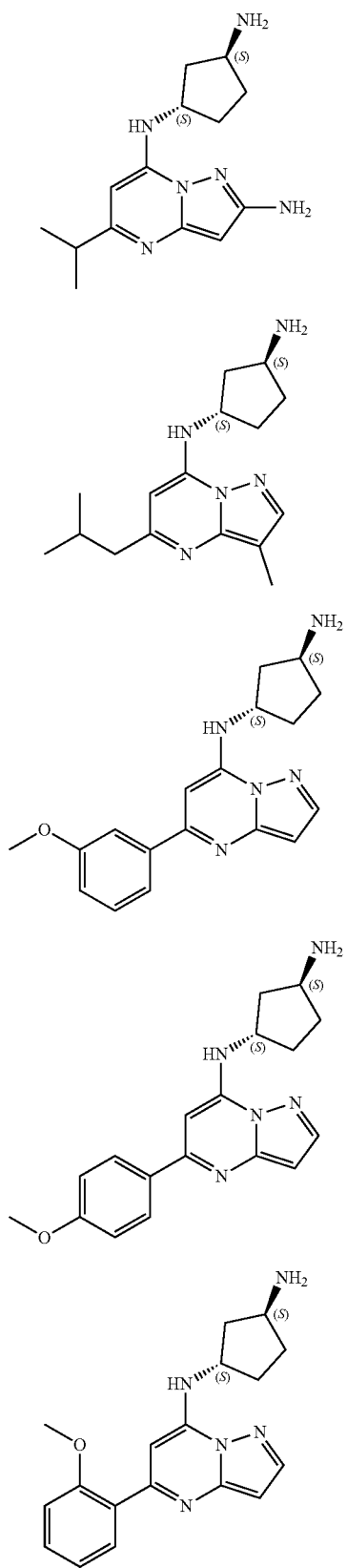
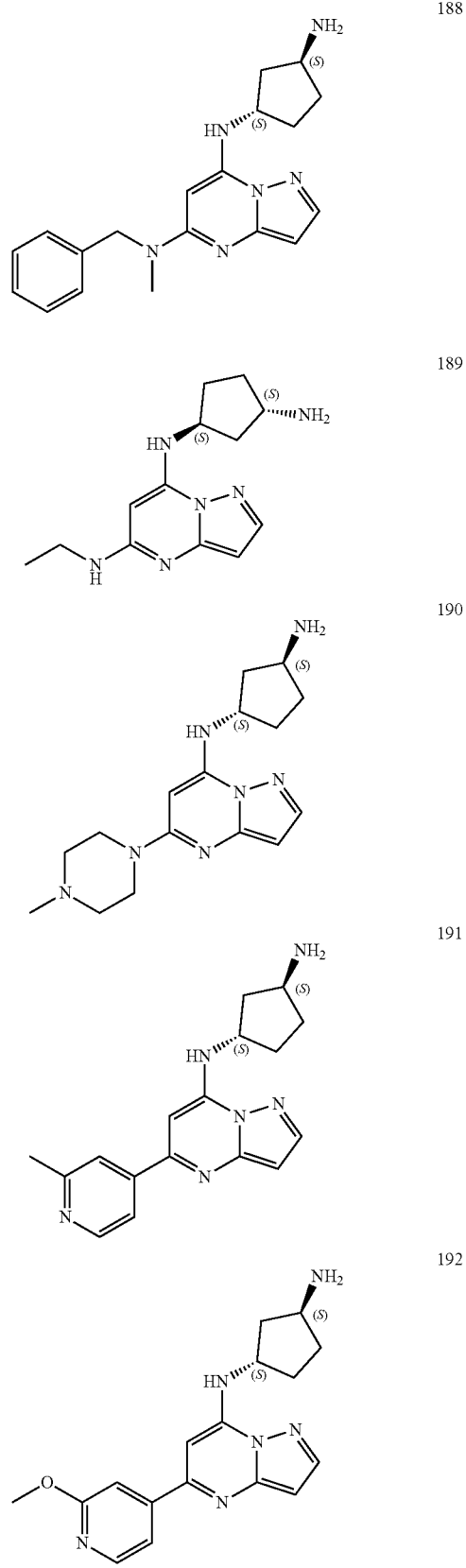

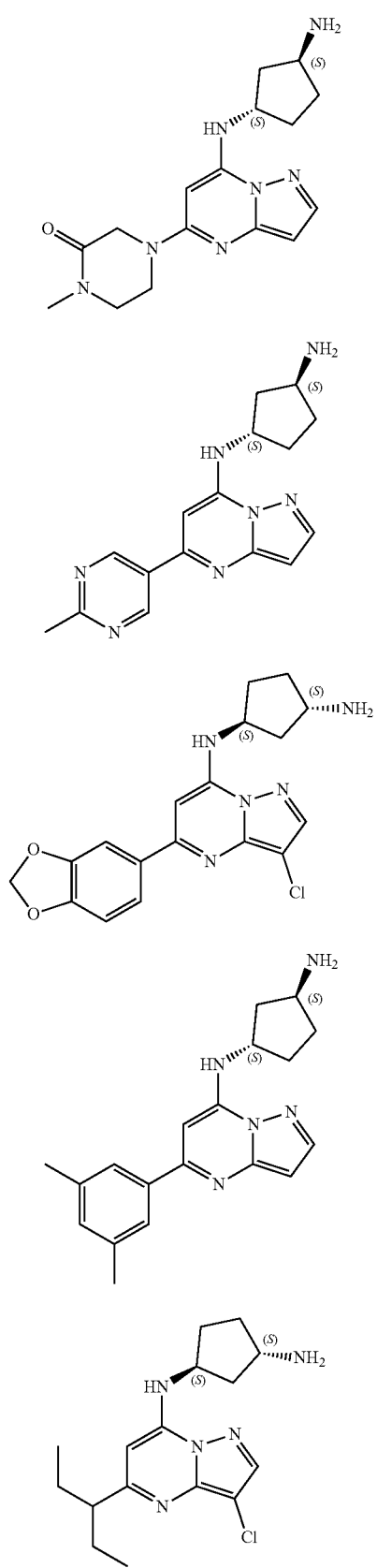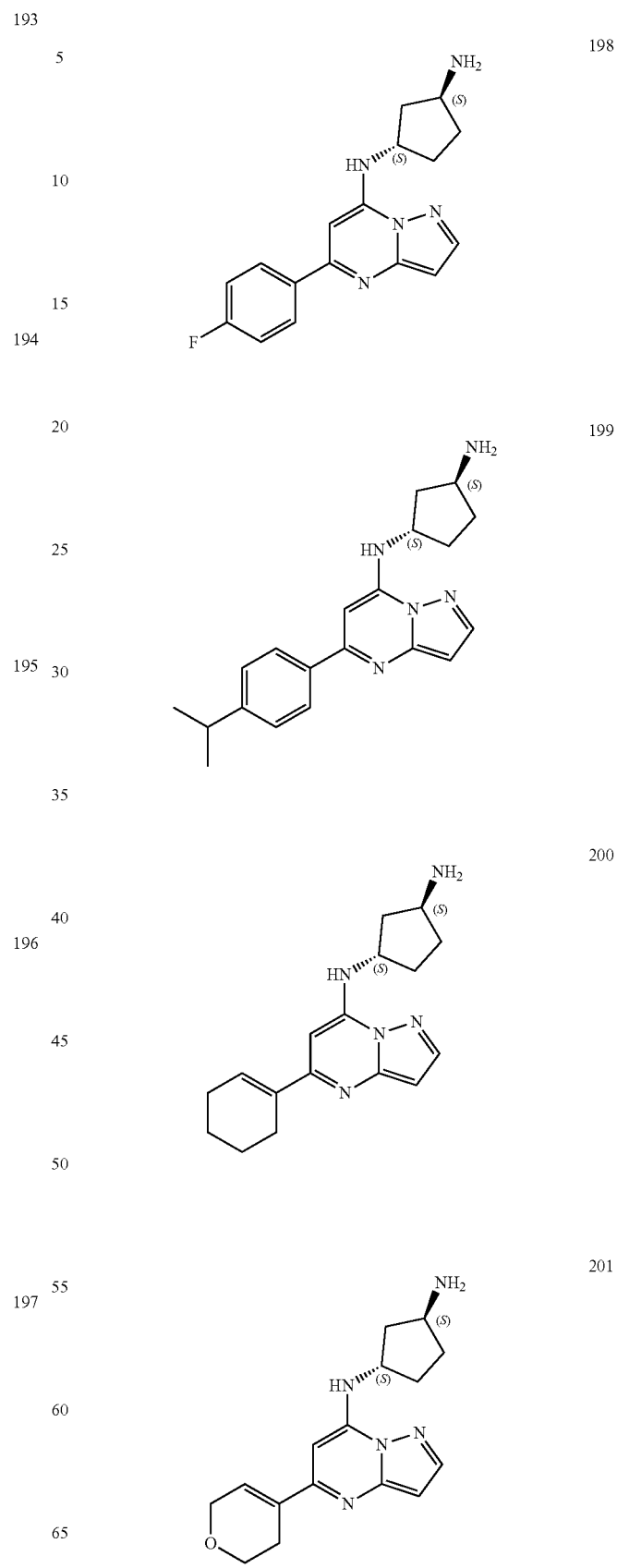

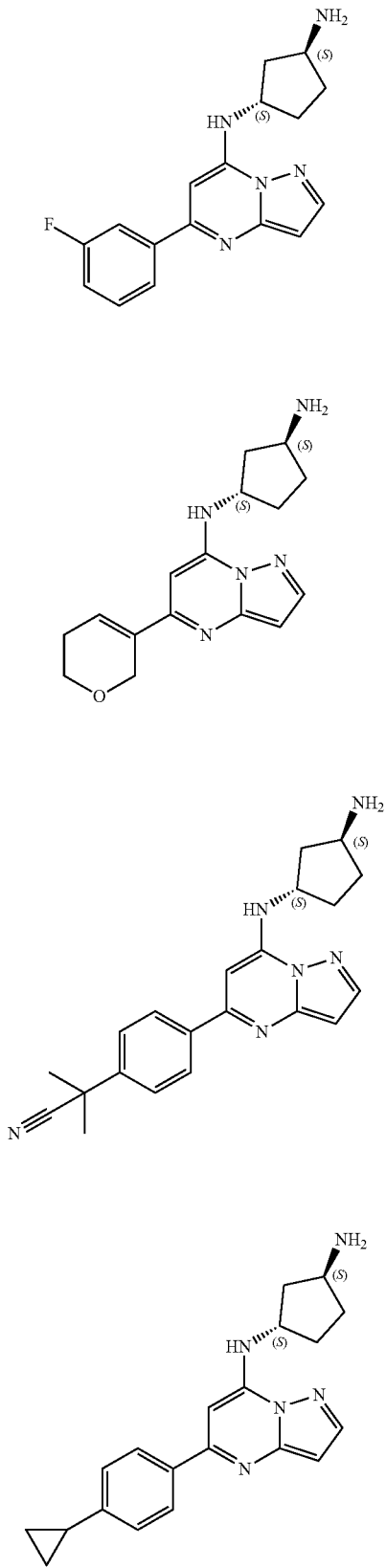

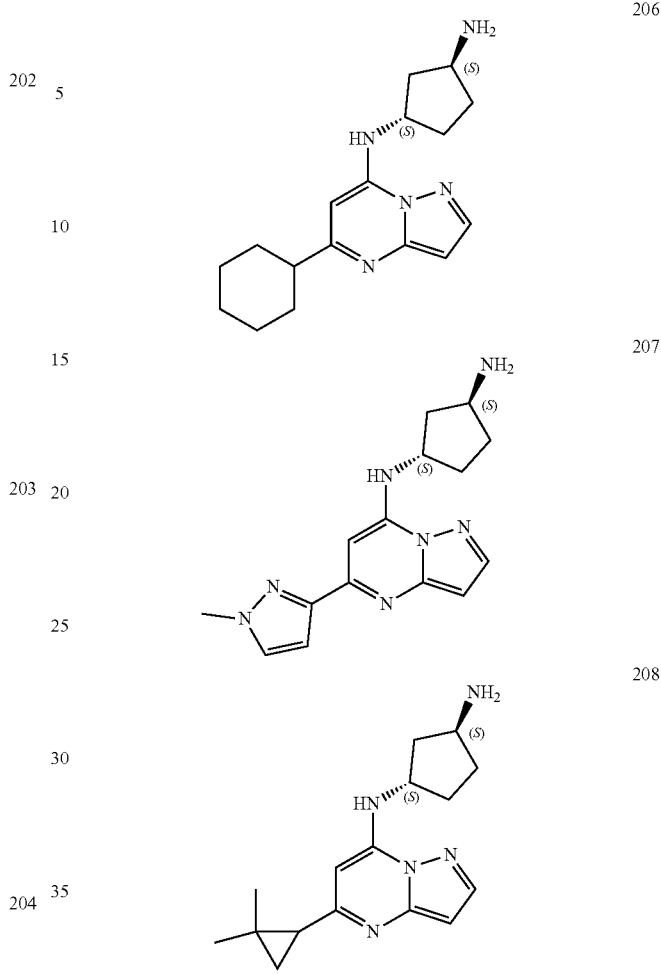

An "effective amount" or "therapeutically effective amount" is an amount of the compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose will be that amount of the compound that is the lowest dose effective to produce the desired effect with no or minimal side effects.

A suitable, non-limiting example of a dosage of the compounds according to the present disclosure is from about 1 ng/kg to about 1000 mg/kg, such as from about 1 mg/kg to about 100 mg/kg, including from about 5 mg/kg to about 50 mg/kg. Other representative dosages of a PI3K inhibitor include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

Yet another embodiment of the present disclosure is a pharmaceutical composition for treating a CDK9-mediated disease. The CDK9-mediated disease may be a hyperproliferative diseases (e.g., cancer), virally induced infectious diseases, or a cardiovascular disease. Examples include acute myelogenous leukemia, primary peritoneal carcinoma, chronic lymphocytic leukemia, relapsed multiple myeloma, non-Hodgkin's lymphoma, acute lymphoblastic leukemia, acute byphenotypic leukemias, advanced breast cancer, non-small cell lung cancer, liver cancer such as hepatocellular carcinoma, and solid advanced tumors. In particular, the compounds may be used to treat a cancer caused by aberrant expression of MYC- or MCL-1, a hematologic malignancy, or a solid tumor.

The pharmaceutical composition comprises a pharmaceutically acceptable carrier and an effective amount of the compounds described herein.

A pharmaceutical composition of the present disclosure may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a pharmaceutical composition of the present disclosure may be administered in conjunction with other treatments. A pharmaceutical composition of the present disclosure maybe encapsulated or otherwise protected against gastric or other secretions, if desired.

The pharmaceutical compositions of the disclosure are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present disclosure are formulated into pharmaceutically-acceptable dosage forms by conventional methods known to those of skill in the art using pharmaceutically acceptable carriers well-known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, salicylate, etc. Each pharmaceutically acceptable carrier used in a pharmaceutical composition of the disclosure is "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the disclosure may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, to prolong the effect of a drug (e.g., pharmaceutical formulation), it is desirable to slow its absorption from subcutaneous or intramuscular injection. This may be accomplished by use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

As used herein, a "subject" is a mammal, preferably, a human. In addition to humans, categories of mammals within the scope of the present disclosure include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present disclosure may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, the terms "prevent", "preventing" and grammatical variations thereof mean to administer a compound or composition of the present disclosure to a subject who has not been diagnosed as having the disease or condition at the time of administration, but who could be expected to develop the disease or condition or be at increased risk for the disease or condition. Preventing also includes administration of at least one compound or a composition of the present disclosure to those subjects thought to be predisposed to the disease or condition due to age, familial history, genetic or chromosomal abnormalities, due to the presence of one or more biological markers for the disease or condition and/or due to environmental factors.

The following examples serve to illustrate certain aspects of the disclosure and are not intended to limit the disclosure.

EXAMPLES

The following examples describe preparation and testing of representative compounds.

Example 1: N-cyclopentyl-5-methyl-pyrazolo[1,5-a]pyrimidin-7-amine (1)

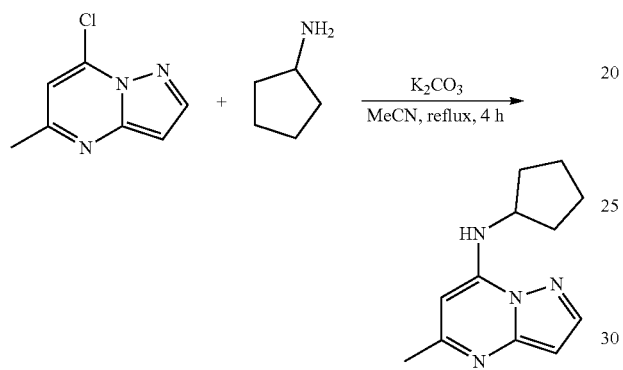

A stirred solution of 7-chloro-5-methyl-pyrazolo[1,5-a]pyrimidine (50.0 mg, 0.3000 mmol), cyclopentanamine (30.48 mg, 0.3600 mmol) and K$_2$CO$_3$ (82.34 mg, 0.6000 mmol) in MeCN (4 mL) was heated to reflux for 4 h. The reaction mixture was filtered, concentrated under reduced pressure and purified by column chromatography, eluent 30% ethyl acetate in hexane, to give N-cyclopentyl-5-methyl-pyrazolo[1,5-a]pyrimidin-7-amine (51.58 mg, 0.2358 mmol, 79.046% yield) (1) as light yellow, amorphous solid. The reaction mixture was monitored by TLC (40% ethyl acetate in hexanes; Product Rf=0.4, SM Rf=0.6).

Example 2: N-cyclopentyl-5-isopropyl-pyrazolo[1,5-a]pyrimidin-7-amine (2)

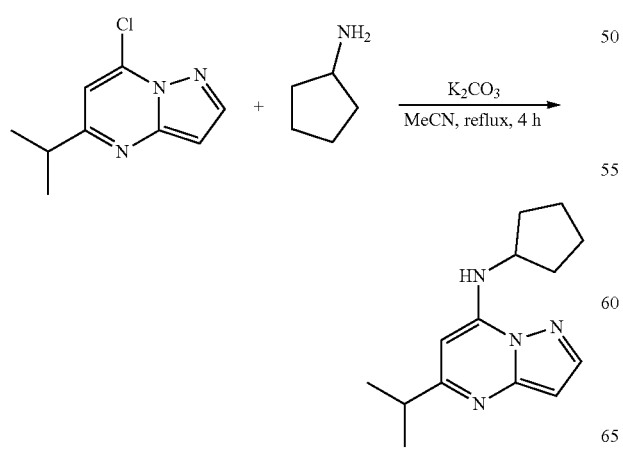

To a stirred solution of 7-chloro-5-isopropyl-pyrazolo[1,5-a]pyrimidine (65.0 mg, 0.3300 mmol), cyclopentanamine (0.04 mL, 0.4000 mmol) and K$_2$CO$_3$ (91.69 mg, 0.6600 mmol) in MeCN (4 mL) were heated to reflux for 4 h. The reaction mixture was filtered, concentrated under reduced pressure and purified by column chromatography, eluent 15% ethyl acetate in hexane to give N-cyclopentyl-5-isopropyl-pyrazolo[1,5-a]pyrimidin-7-amine (48.02 mg, 0.1953 mmol, 58.789% yield) (2) as light yellow, amorphous solid. The reaction mixture was monitored by TLC (20% ethyl acetate in hexanes; Product Rf=0.3, SM Rf=0.6).

Example 3: N-cyclopentyl-5-sec-butyl-pyrazolo[1,5-a]pyrimidin-7-amine (3)

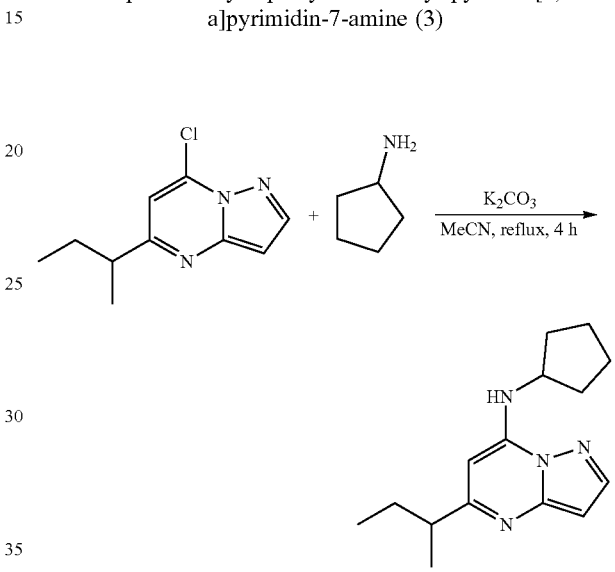

To a stirred solution of 7-chloro-5-sec-butyl-pyrazolo[1,5-a]pyrimidine (50.mg, 0.2400 mmol), cyclopentanamine (24.37 mg, 0.2900 mmol) and K$_2$CO$_3$ (82.28 mg, 0.6000 mmol) in MeCN (5 mL) were heated to reflux for 4 h. The reaction mixture was filtered, concentrated under reduced pressure and purified by column chromatography to get N-cyclopentyl-5-sec-butyl-pyrazolo[1,5-a]pyrimidin-7-amine (21.27 mg, 0.0823 mmol, 34.519% yield) (3) as light yellow, amorphous solid. The reaction mixture was monitored by TLC (30% ethyl acetate in hexanes, Product Rf=0.4, SM Rf=0.5).

Example 4: [4-[(5-methylpyrazolo[1,5-a]pyrimidin-4-ium-7-yl)amino]cyclohexyl]ammonium dichloride (4)

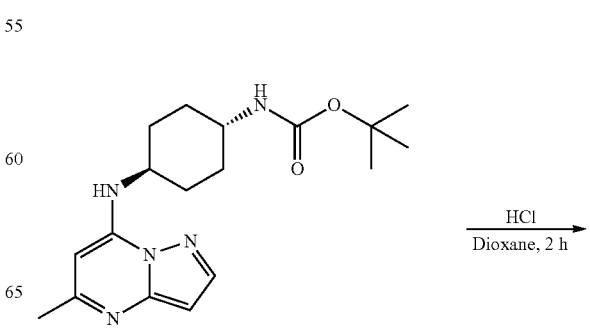

55
-continued

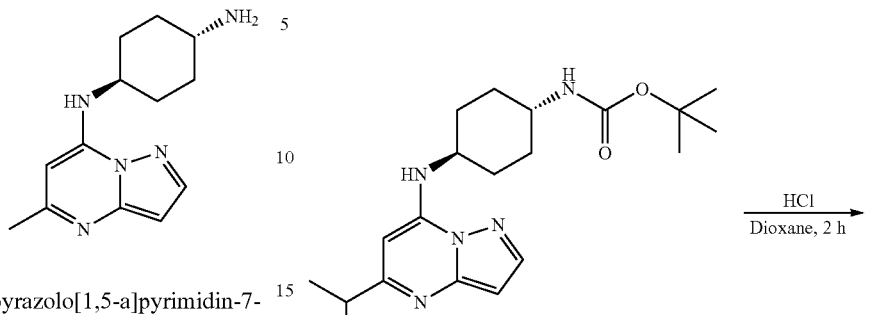

To tert-butyl N-[4-[(5-methylpyrazolo[1,5-a]pyrimidin-7-yl)amino]cyclohexyl]carbamate (60.0 mg, 0.1700 mmol), HCl in dioxane (2 mL, 0.1700 mmol) was added and stirred at room temperature for 2 h. The reaction mixture was evaporated in vacuo to give [4-[(5-methylpyrazolo[1,5-a]pyrimidin-4-ium-7-yl)amino]cyclohexyl]ammonium dichloride (39.89 mg, 0.1247 mmol, 71.803% yield) (4) as a white solid. The reaction mixture was monitored by TLC (100% ethyl acetate; Product Rf=0.1, SM Rf=0.8).

Example 5: N,5-dicyclopentylpyrazolo[1,5-a]pyrimidin-7-amine (5)

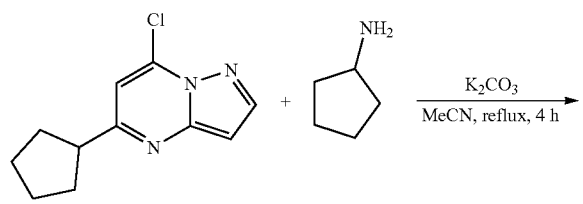

A stirred solution of 7-chloro-5-cyclopentyl-pyrazolo[1,5-a]pyrimidine (50.0 mg, 0.2300 mmol), cyclopentanamine (23.05 mg, 0.2700 mmol) and K₂CO₃ (77.81 mg, 0.5600 mmol) in MeCN (5 mL) was heated to reflux for 4 h. The reaction mixture was filtered, concentrated under reduced pressure and purified by column chromatography to get N,5-dicyclopentylpyrazolo[1,5-a]pyrimidin-7-amine (33.17 mg, 0.1227 mmol, 54.396% yield) (5) as a light yellow solid. The reaction mixture was monitored by TLC (30% ethyl acetate in hexanes; Product Rf=0.4, SM Rf=0.5)

56

Example 6: [4-[(5-isopropylpyrazolo[1,5-a]pyrimidin-4-ium-7-yl)amino]cyclohexyl]ammonium dichloride (6)

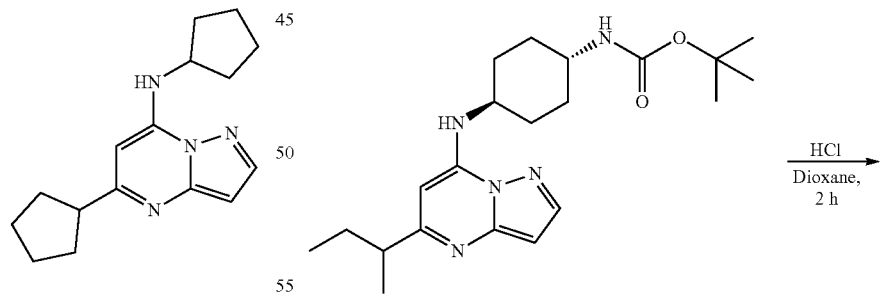

To tert-butyl N-[4-[(5-isopropylpyrazolo[1,5-a]pyrimidin-7-yl)amino]cyclohexyl]carbamate (80.0 mg, 0.2100 mmol), HCl in dioxane (2.mL, 0.2100 mmol) was added and stirred at room temperature for 2 h. The reaction mixture was evaporated in vacuo to give [4-[(5-isopropylpyrazolo[1,5-a]pyrimidin-4-ium-7-yl)amino]cyclohexyl]ammonium dichloride (64.82 mg, 0.1796 mmol, 83.865% yield) (6) as an off-white solid. The reaction mixture was monitored by TLC (100% ethyl acetate; Product Rf=0.1, SM Rf=0.8).

Example 7: [4-[(5-sec-butylpyrazolo[1,5-a]pyrimidin-4-ium-7-yl)amino]cyclohexyl]ammonium dichloride (7)

To tert-butyl N-[4-[(5-sec-butylpyrazolo[1,5-a]pyrimidin-7-yl)amino]cyclohexyl]carbamate (65.0 mg, 0.1700 mmol), HCl in dioxane (2.mL, 0.1700 mmol) was added and stirred at room temperature for 2 h. The reaction mixture was evaporated in vacuo to give[4-[(5-sec-butylpyrazolo[1,5-a]pyrimidin-4-ium-7-yl)amino]cyclohexyl]ammonium dichloride (46.75 mg, 0.1297 mmol, 77.35% yield) (7) as an off-white solid. The reaction mixture was monitored by TLC (100% ethyl acetate; Product Rf=0.1, SM Rf=0.78).

Example 8: [4-[(5-cyclopentylpyrazolo[1,5-a]pyrimidin-4-ium-7-yl)amino]cyclohexyl]ammonium dichloride (8)

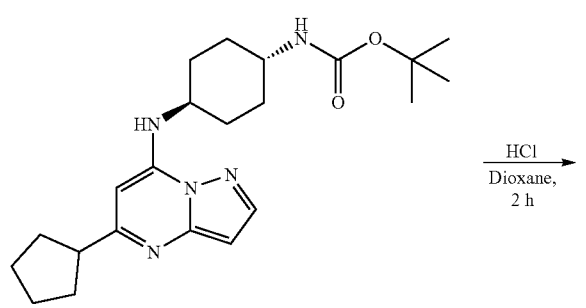

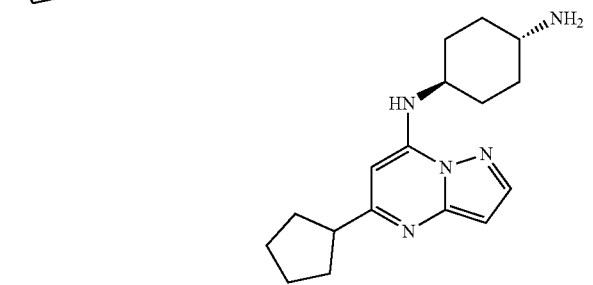

To tert-butyl N-[4-[(5-cyclopentylpyrazolo[1,5-a]pyrimidin-7-yl)amino]cyclohexyl]carbamate (72.17 mg, 0.1800 mmol), HCl in dioxane (2.mL, 0.1800 mmol) was added and stirred at room temperature for 2 h. The reaction mixture was evaporated in vacuo to give[4-[(5-cyclopentylpyrazolo[1,5-a]pyrimidin-4-ium-7-yl)amino]cyclohexyl]ammonium dichloride (59.36 mg, 0.1594 mmol, 88.257% yield) (8) as an off white solid. The reaction mixture was monitored by TLC (100% ethyl acetate; Product Rf=0.1, SM Rf=0.8).

Example 9: [(1S,3S)-3-[(5-cyclopentylpyrazolo[1,5-a]pyrimidin-4-ium-7-yl)amino]cyclopentyl]ammonium dichloride (9)

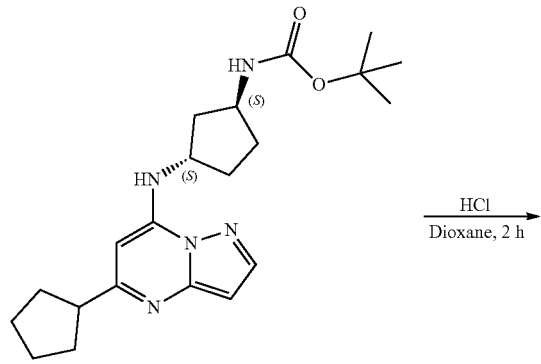

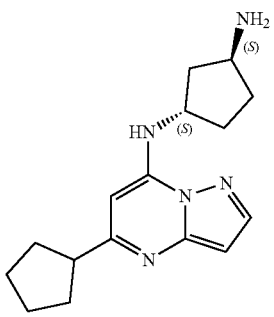

To tert-butyl N-[(1S,3S)-3-[(5-cyclopentylpyrazolo[1,5-a]pyrimidin-7-yl)amino]cyclopentyl]carbamate (105.mg, 0.2700 mmol), HCl in dioxane (2.0 mL, 0.2700 mmol) was added and stirred at room temperature for 2 h. The reaction mixture was evaporated in vacuo to give [(1S,3S)-3-[(5-cyclopentylpyrazolo[1,5-a]pyrimidin-4-ium-7-yl)amino]cyclopentyl]ammonium dichloride (51.28 mg, 0.1431 mmol, 52.544% yield) (9) as a light-yellow solid. The reaction mixture was monitored by TLC (100% ethyl acetate; Product Rf=0.1, SM Rf=0.8).

Example 10: [(1S,3R)-3-[(5-methylpyrazolo[1,5-a]pyrimidin-4-ium-7-yl)amino]cyclopentyl]ammonium dichloride (10)

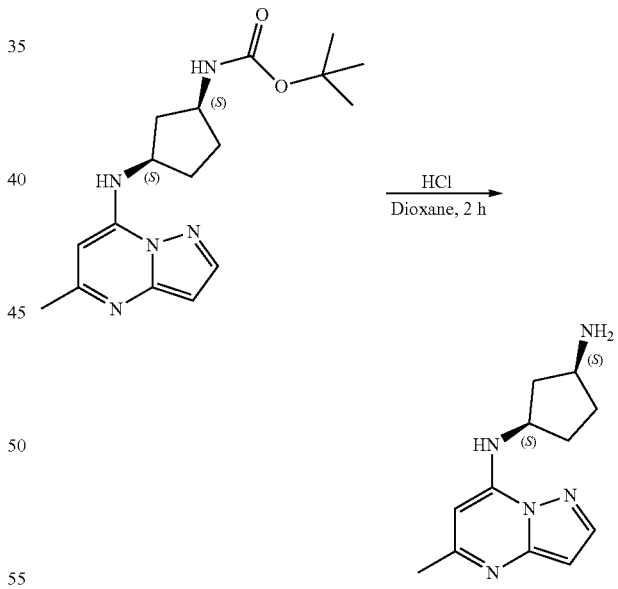

To tert-butyl N-[(1S,3R)-3-[(5-methylpyrazolo[1,5-a]pyrimidin-7-yl)amino]cyclopentyl]carbamate (100.0 mg, 0.3000 mmol), HCl in dioxane (2.mL, 0.3000 mmol) was added and stirred at room temperature for 2 h. The reaction mixture was evaporated in vacuo to give [(1S,3R)-3-[(5-methylpyrazolo[1,5-a]pyrimidin-4-ium-7-yl)amino]cyclopentyl]ammonium dichloride (84.11 mg, 0.2685 mmol, 88.979% yield) (10) as an off-white solid. The reaction mixture was monitored by TLC (100% ethyl acetate; Product Rf=0.1, SM Rf=0.8).

Example 11: [3-[(5-methylpyrazolo[1,5-a]pyrimidin-4-ium-7-yl)amino]cyclobutyl]ammonium dichloride (11)

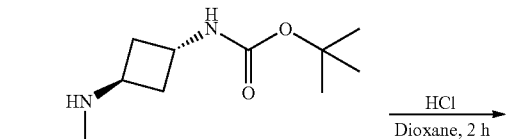

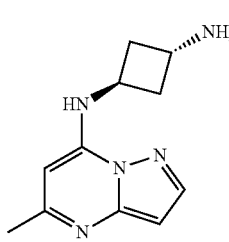

To tert-butyl N-[3-[(5-methylpyrazolo[1,5-a]pyrimidin-7-yl)amino]cyclobutyl]carbamate (90.mg, 0.2800 mmol), HCl in dioxane (2.0 mL, 0.2800 mmol) was added and stirred at room temperature for 2 h. The reaction mixture was evaporated in vacuo to give [3-[(5-methylpyrazolo[1,5-a]pyrimidin-4-ium-7-yl)amino]cyclobutyl]ammonium dichloride (65.42 mg, 0.2240 mmol, 79.009% yield) (11) as light brown solid. The reaction mixture was monitored by TLC (100% ethyl acetate; Product Rf=0.1, SM Rf=0.8).

Example 12: [(1R,3S)-3-[(5-methylpyrazolo[1,5-a]pyrimidin-4-ium-7-yl)amino]cyclopentyl]ammonium dichloride (12)

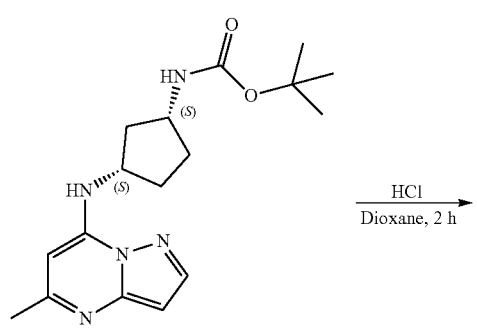

To tert-butyl N-[(1R,3S)-3-[(5-methylpyrazolo[1,5-a]pyrimidin-7-yl)amino]cyclopentyl]carbamate (80.0 mg, 0.2400 mmol), HCl in dioxane (2.0 mL, 0.2400 mmol) was added and stirred at room temperature for 2 h. The reaction mixture was evaporated in vacuo to give [(1R,3S)-3-[(5-methylpyrazolo[1,5-a]pyrimidin-4-ium-7-yl)amino]cyclopentyl]ammonium dichloride (61.39 mg, 0.1993 mmol, 82.568% yield) (12) as an off-white solid. The reaction mixture was monitored by TLC (100% ethyl acetate; Product Rf=0.1, SM Rf=0.8).

Example 13: (1S,3R)—N3-(5-isopropylpyrazolo[1,5-a]pyrimidin-7-yl)cyclopentane-1,3-diamine (13)

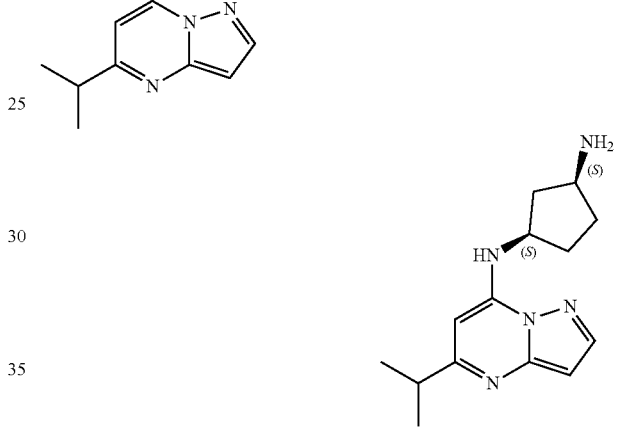

To tert-butyl N-[(1S,3R)-3-[(5-isopropylpyrazolo[1,5-a]pyrimidin-7-yl)amino]cyclopentyl]carbamate (80.0 mg, 0.2200 mmol), HCl in dioxane (2.0 mL, 0.2200 mmol) was added and stirred at room temperature for 2 h. The reaction mixture was evaporated in vacuo and neutralized by PL-HCO3 MP SPE 200MG/6ML cartridge to give (1S,3R)—N3-(5-isopropylpyrazolo[1,5-a]pyrimidin-7-yl)cyclopentane-1,3-diamine (26.03 mg, 0.0978 mmol, 43.966% yield) (13) as a light yellow, amorphous solid. The reaction mixture was monitored by TLC (100% ethyl acetate; Product Rf=0.1, SM Rf=0.8).

Example 14: (1S,3R)—N3-(5-sec-butylpyrazolo[1,5-a]pyrimidin-7-yl)cyclopentane-1,3-diamine (14)

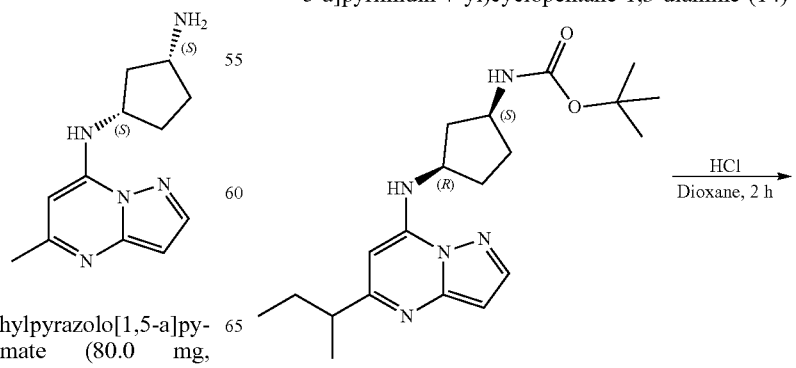

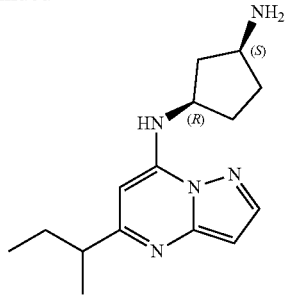

To tert-butyl N-[(1S,3R)-3-[(5-sec-butylpyrazolo[1,5-a]pyrimidin-7-yl)amino]cyclopentyl]carbamate (100.mg, 0.2700 mmol), HCl in dioxane (2.0 mL, 0.2700 mmol) was added and stirred at room temperature for 2 h. The reaction mixture was evaporated in vacuo and neutralized by PL-HCO3 MP SPE 200MG/6ML cartridge to give (1S,3R)—N3-(5-sec-butylpyrazolo[1,5-a]pyrimidin-7-yl)cyclopentane-1,3-diamine (34.04 mg, 0.1245 mmol, 46.505% yield) (14) as a light green, amorphous solid. The reaction mixture was monitored by TLC (100% ethyl acetate; Product Rf=0.1, SM Rf=0.8).

Example 15: tert-butyl N-[(1S,3R)-3-[(5-cyclopentylpyrazolo[1,5-a]pyrimidin-7-yl)amino]cyclopentyl]carbamate (15)

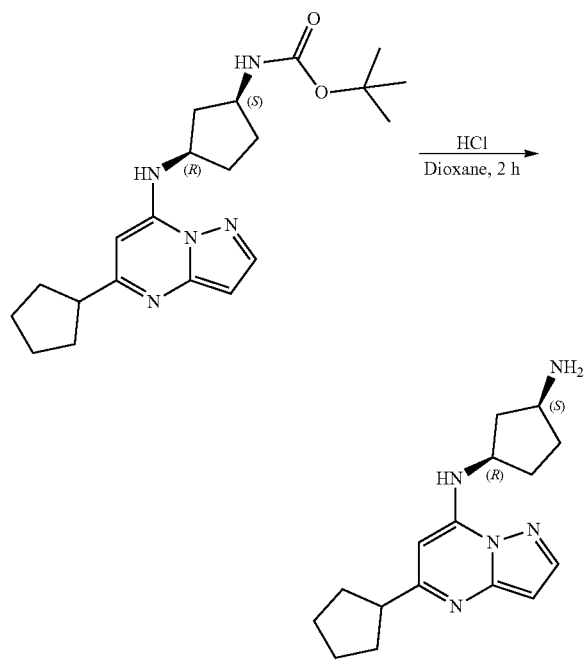

To tert-butyl N-[(1S,3R)-3-[(5-cyclopentylpyrazolo[1,5-a]pyrimidin-7-yl)amino]cyclopentyl]carbamate (100.mg, 0.2600 mmol), HCl in dioxane (2.0 mL, 0.2600 mmol) was added and stirred at room temperature for 2 h. The reaction mixture was evaporated in vacuo and neutralized by PL-HCO3 MP SPE 200MG/6ML cartridge to give (1S,3R)—N3-(5-cyclopentylpyrazolo[1,5-a]pyrimidin-7-yl)cyclopentane-1,3-diamine (31.91 mg, 0.1118 mmol, 43.103% yield) (15) as a light yellow, amorphous solid. The reaction mixture was monitored by TLC (100% ethyl acetate, Product Rf=0.1, SM Rf=0.8).

Example 16: (1R,3S)—N3-(5-isopropylpyrazolo[1,5-a]pyrimidin-7-yl)cyclopentane-1,3-diamine (16)

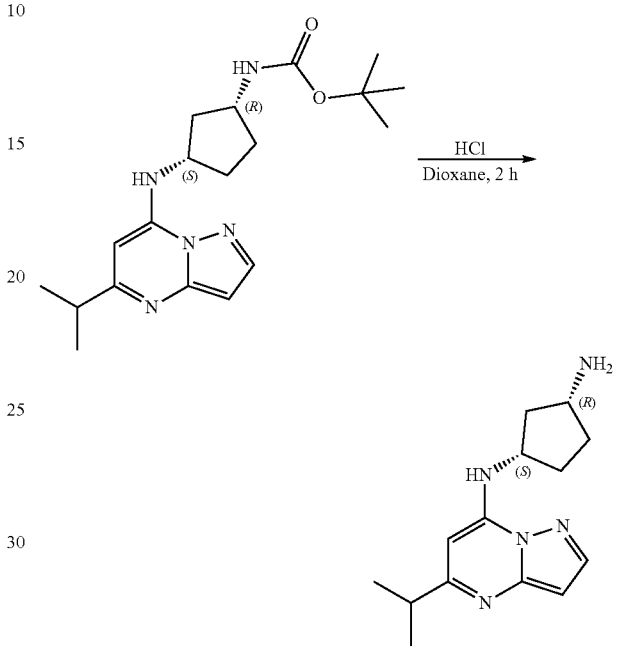

To tert-butyl N-[(1R,3S)-3-[(5-isopropylpyrazolo[1,5-a]pyrimidin-7-yl)amino]cyclopentyl]carbamate (75.mg, 0.2100 mmol), HCl in dioxane (2.0 mL, 0.2100 mmol) was added and stirred at room temperature for 2 h. The reaction mixture was evaporated in vacuo and neutralized by PL-HCO3 MP SPE 200MG/6ML cartridge to give (1R,3S)—N3-(5-isopropylpyrazolo[1,5-a]pyrimidin-7-yl)cyclopentane-1,3-diamine (30.78 mg, 0.1158 mmol, 55.49% yield) (16) as a light yellow, amorphous solid. The reaction mixture was monitored by TLC (100% ethyl acetate; Product Rf=0.1, SM Rf=0.8).

Example 17: (1S,3S)—N3-(5-isopropylpyrazolo[1,5-a]pyrimidin-7-yl)cyclopentane-1,3-diamine (17)

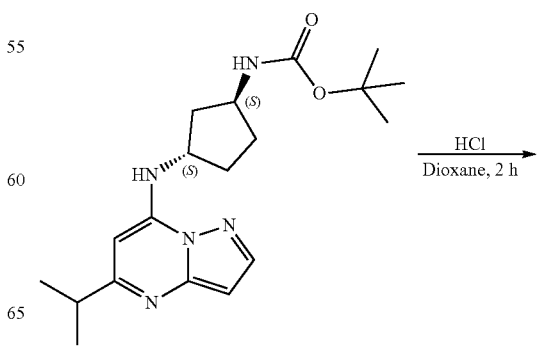

-continued

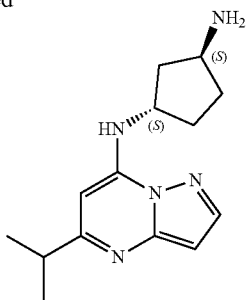

To tert-butyl N-[(1S,3S)-3-[(5-isopropylpyrazolo[1,5-a]pyrimidin-7-yl)amino]cyclopentyl]carbamate (80.0 mg, 0.2200 mmol), HCl in dioxane (2.0 mL, 0.2200 mmol) was added and stirred at room temperature for 2 h. The reaction mixture was evaporated in vacuo and neutralized by PL-HCO3 MP SPE 200MG/6ML cartridge to give (1S,3S)—N3-(5-isopropylpyrazolo[1,5-a]pyrimidin-7-yl)cyclopentane-1,3-diamine (31.02 mg, 0.1160 mmol, 52.142% yield) (17) as light yellow gummy. The reaction mixture was monitored by TLC (100% ethyl acetate; Product Rf=0.1, SM Rf=0.8).

Example 18: (1S,3S)—N3-(5-sec-butylpyrazolo[1,5-a]pyrimidin-7-yl)cyclopentane-1,3-diamine (18)

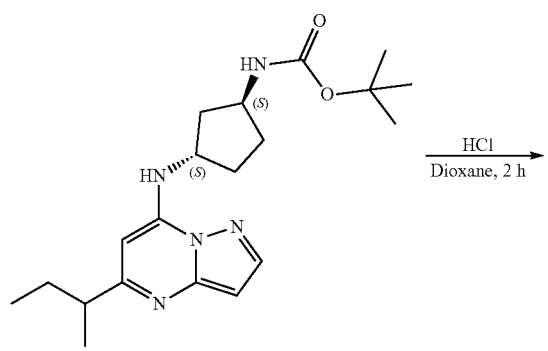

To tert-butyl N-[(1S,3S)-3-[(5-sec-butylpyrazolo[1,5-a]pyrimidin-7-yl)amino]cyclopentyl]carbamate (105.0 mg, 0.2800 mmol), HCl in Dioxane (2.0 mL, 0.2800 mmol) was added and stirred at room temperature for 2 h. The reaction mixture was evaporated in vacuo and neutralized by PL-HCO3 MP SPE 200MG/6ML cartridge to give (1S,3S)—N3-(5-sec-butylpyrazolo[1,5-a]pyrimidin-7-yl)cyclopentane-1,3-diamine (20.55 mg, 0.0752 mmol, 26.738% yield) (18) as a light yellow, amorphous solid. The reaction mixture was monitored by TLC (100% ethyl acetate; Product Rf=0.1, SM Rf=0.8).

Example 19: N1-(5-sec-butylpyrazolo[1,5-a]pyrimidin-7-yl)cyclobutane-1,3-diamine (19)

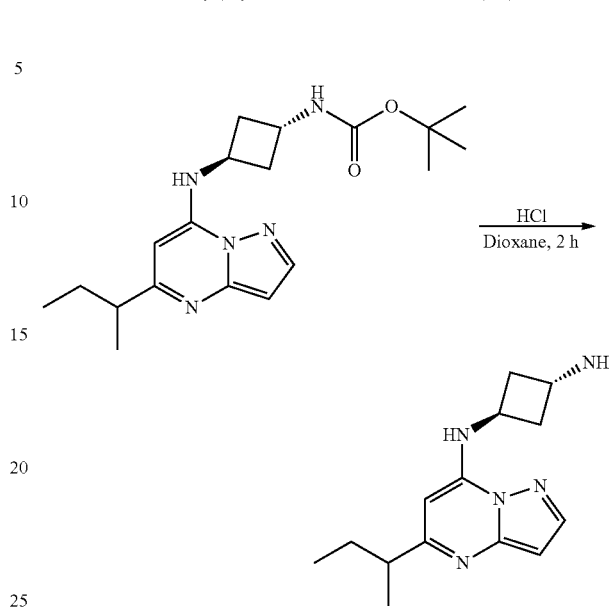

To tert-butyl N-[3-[(5-sec-butylpyrazolo[1,5-a]pyrimidin-7-yl)amino]cyclobutyl]carbamate (85.0 mg, 0.2400 mmol), HCl in dioxane (2.0 mL, 0.2400 mmol) was added and stirred at room temperature for 2 h. The reaction mixture was evaporated in vacuo and neutralized by PL-HCO3 MP SPE 200MG/6ML cartridge to give N1-(5-sec-butylpyrazolo[1,5-a]pyrimidin-7-yl)cyclobutane-1,3-diamine (30.61 mg, 0.1180 mmol, 49.914% yield) (19) as a light yellow, amorphous solid. The reaction mixture was monitored by TLC (100% ethyl acetate; Product Rf=0.1, SM Rf=0.8).

Example 20: N1-(5-cyclopentylpyrazolo[1,5-a]pyrimidin-7-yl)cyclobutane-1,3-diamine (20)

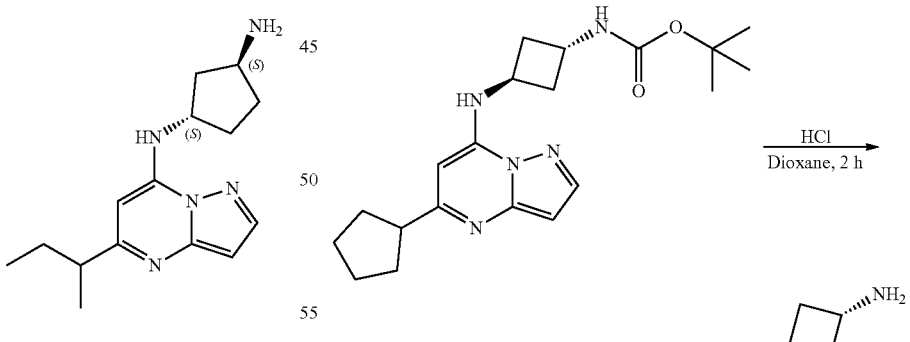

To tert-butyl N-[3-[(5-cyclopentylpyrazolo[1,5-a]pyrimidin-7-yl)amino]cyclobutyl]carbamate (80.0 mg, 0.2200 mmol), HCl in dioxane (2.0 mL, 0.2200 mmol) was added and stirred at room temperature for 2 h. The reaction mixture was evaporated in vacuo and neutralized by PL-HCO3 MP SPE 200MG/6ML cartridge to give N1-(5-cyclopentylpyrazolo[1,5-a]pyrimidin-7-yl)cyclobutane-1,3-diamine (29.52 mg, 0.1088 mmol, 50.514% yield) (20) as a light-yellow gummy. The reaction mixture was monitored by TLC (100% ethyl acetate; Product Rf=0.1, SM Rf=0.8).

Example 21: N1-(5-isopropylpyrazolo[1,5-a]pyrimidin-7-yl)cyclobutane-1,3-diamine (21)

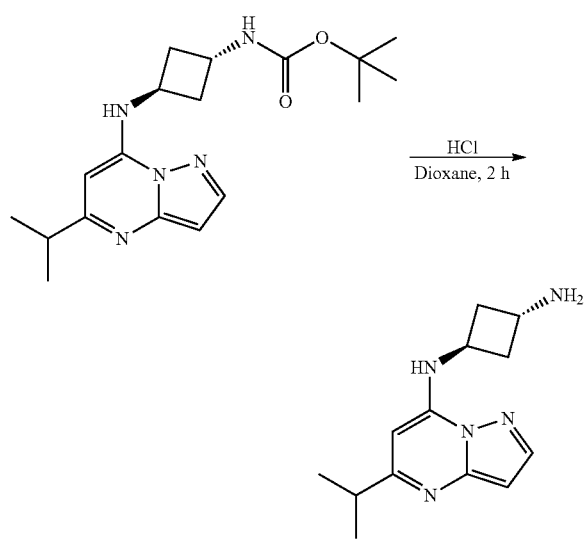

To tert-butyl N-[3-[(5-isopropylpyrazolo[1,5-a]pyrimidin-7-yl)amino]cyclobutyl]carbamate (75.0 mg, 0.2200 mmol), HCl in dioxane (2.0 mL, 0.2200 mmol) was added and stirred at room temperature for 2 h. The reaction mixture was evaporated in vacuo and neutralized by PL-HCO3 MP SPE 200MG/6ML cartridge to give N1-(5-isopropylpyrazolo[1,5-a]pyrimidin-7-yl)cyclobutane-1,3-diamine (32.01 mg, 0.1251 mmol, 57.616% yield) (21) as light yellow, amorphous solid. The reaction mixture was monitored by TLC (100% ethyl acetate; Product Rf=0.1, SM Rf=0.8).

Example 22: (1R,3S)—N3-(5-sec-butylpyrazolo[1,5-a]pyrimidin-7-yl)cyclopentane-1,3-diamine (22)

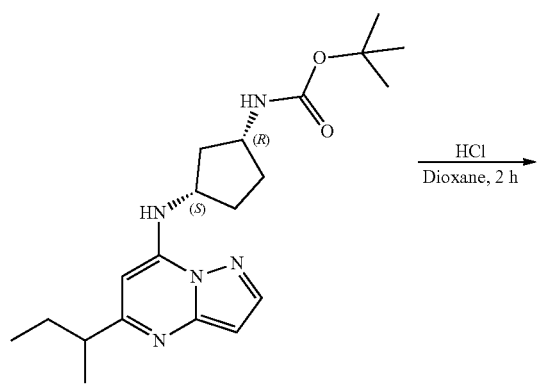

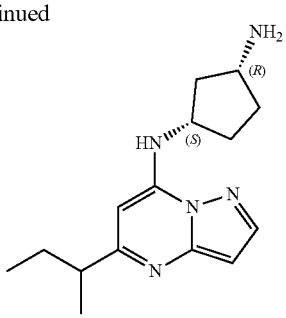

To tert-butyl N-[(1R,3S)-3-[(5-sec-butylpyrazolo[1,5-a]pyrimidin-7-yl)amino]cyclopentyl]carbamate (100.0 mg, 0.2700 mmol), HCl in dioxane (2.0 mL, 0.2700 mmol) was added and stirred at room temperature for 2 h. The reaction mixture was evaporated in vacuo and neutralized by PL-HCO3 MP SPE 200MG/6ML cartridge to give (1R,3S)—N3-(5-sec-butylpyrazolo[1,5-a]pyrimidin-7-yl)cyclopentane-1,3-diamine (28.39 mg, 0.1038 mmol, 38.786% yield) (22) as a light yellow, amorphous solid. The reaction mixture was monitored by TLC (100% ethyl acetate; Product Rf=0.1, SM Rf=0.8).

Example 23: (1R,3S)—N3-(5-cyclopentylpyrazolo[1,5-a]pyrimidin-7-yl)cyclopentane-1,3-diamine (23)

To tert-butyl N-[(1R,3S)-3-[(5-cyclopentylpyrazolo[1,5-a]pyrimidin-7-yl)amino]cyclopentyl]carbamate (100.0 mg, 0.2600 mmol), HCl in dioxane (2.0 mL, 0.2600 mmol) was added and stirred at room temperature for 2 h. The reaction mixture was evaporated in vacuo and neutralized by PL-HCO3 MP SPE 200MG/6ML cartridge to give (1R,3S)—N3-(5-cyclopentylpyrazolo[1,5-a]pyrimidin-7-yl)cyclopentane-1,3-diamine (33.05 mg, 0.1158 mmol, 44.643% yield)

(23) as a light yellow, amorphous solid. The reaction mixture was monitored by TLC (100% ethyl acetate; Product Rf=0.1, SM Rf=0.8).

Example 24: (1S,3S)—N3-(5-methylpyrazolo[1,5-a]pyrimidin-7-yl)cyclopentane-1,3-diamine (24)

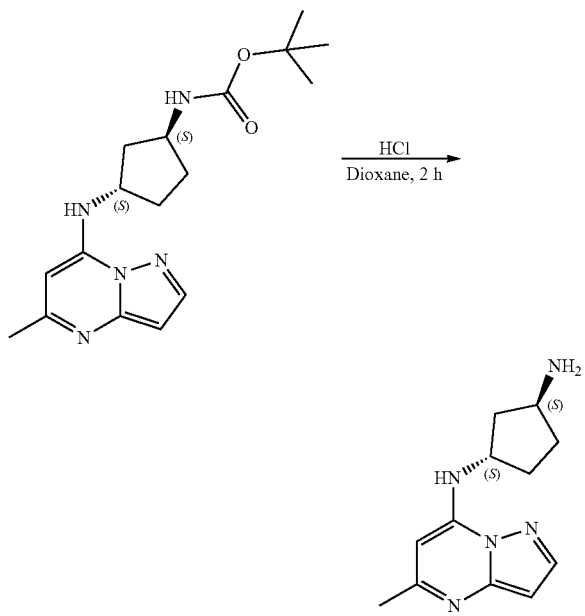

To tert-butyl N-[(1S,3S)-3-[(5-methylpyrazolo[1,5-a]pyrimidin-7-yl)amino]cyclopentyl]carbamate (80.0 mg, 0.2400 mmol), HCl in dioxane (2.0 mL, 0.2400 mmol) was added and stirred at room temperature for 2 h. The reaction mixture was evaporated in vacuo, neutralized by PL-HCO3 MP SPE 200MG/6ML cartridge and purified by prep HPLC to give (1S,3S)—N3-(5-methylpyrazolo[1,5-a]pyrimidin-7-yl)cyclopentane-1,3-diamine (21.15 mg, 0.0899 mmol, 37.263% yield) (24) as an off-white solid. The reaction mixture was monitored by TLC (100% ethyl acetate; Product Rf=0.1, SM Rf=0.8).

Example 25: (1R,3R)—N3-(5-ethylpyrazolo[1,5-a]pyrimidin-7-yl)cyclopentane-1,3-diamine (25)

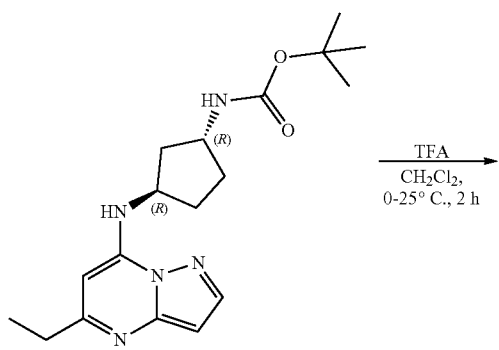

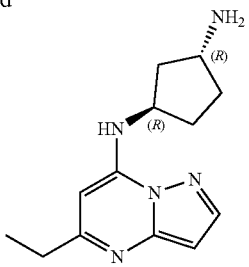

To a stirred solution of tert-butyl N-[(1R,3R)-3-[(5-ethylpyrazolo[1,5-a]pyrimidin-7-yl)amino]cyclopentyl]carbamate (62.0 mg, 0.1800 mmol) in DCM (3.5896 mL) at 0° C. was added trifluoroacetic acid (0.34 mL, 4.49 mmol). The reaction was allowed to warm to room temperature and continuously stirred over 2 hours, whereupon LC-MS revealed reaction complete. The reaction was directly concentrated, washed with pentane and dried to yield (1R,3R)—N3-(5-ethylpyrazolo[1,5-a]pyrimidin-7-yl)cyclopentane-1,3-diamine (35 mg, 0.1427 mmol, 79.491% yield) (25). The reaction mixture was monitored by TLC (100% ethyl acetate; Product Rf=0.1, SM Rf=0.8).

Example 26: (1R,3R)—N3-(5-propylpyrazolo[1,5-a]pyrimidin-7-yl)cyclopentane-1,3-diamine (26)

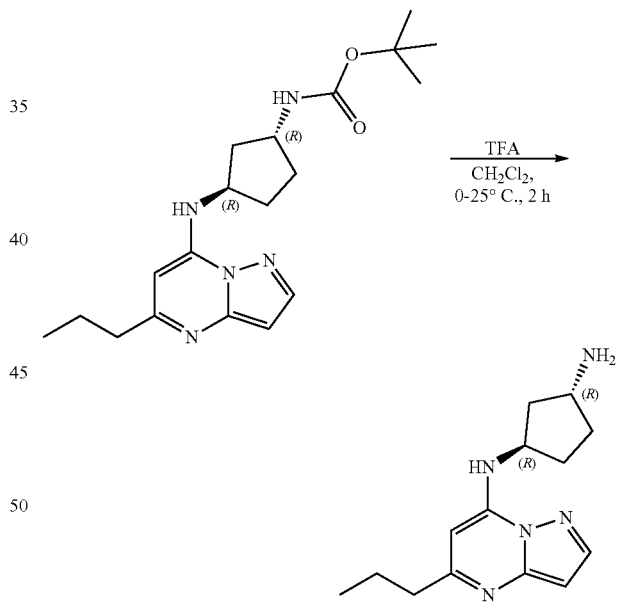

To a stirred solution of tert-butyl N-[(1R,3R)-3-[(5-propylpyrazolo[1,5-a]pyrimidin-7-yl)amino]cyclopentyl]carbamate (41.0 mg, 0.1100 mmol) in DCM (2.2811 mL) at 0° C. was added trifluoroacetic acid (0.22 mL, 2.85 mmol). The reaction was allowed to warm to room temperature and continuously stirred over 2 hours, whereupon LC-MS revealed reaction complete. The reaction was directly concentrated, washed with pentane and dried to yield (1R,3R)—N3-(5-propylpyrazolo[1,5-a]pyrimidin-7-yl)cyclopentane-1,3-diamine (16 mg, 0.0617 mmol, 54.089% yield) (26). The reaction mixture was monitored by TLC (100% ethyl acetate; Product Rf=0.1, SM Rf=0.8)

Example 27: (1S,3S)—N3-(5-propylpyrazolo[1,5-a]pyrimidin-7-yl)cyclopentane-1,3-diamine (27)

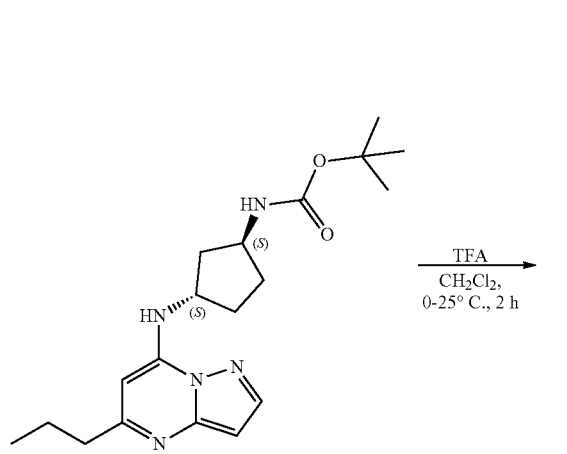

To a stirred solution of tert-butyl N-[(1S,3S)-3-[(5-propylpyrazolo[1,5-a]pyrimidin-7-yl)amino]cyclopentyl]carbamate (47.0 mg, 0.1300 mmol) in DCM (2.615 mL) at 0° C. was added trifluoroacetic acid (0.25 mL, 3.27 mmol). The reaction was allowed to warm to room temperature and continuously stirred at room temperature over 2 hours, whereupon LC-MS revealed reaction complete. The reaction was directly concentrated, washed with pentane and dried to yield (1S,3S)—N3-(5-propylpyrazolo[1,5-a]pyrimidin-7-yl)cyclopentane-1,3-diamine (33 mg, 0.1272 mmol, 97.318% yield) (27). The reaction mixture was monitored by TLC (100% ethyl acetate; Product Rf=0.1, SM Rf=0.8)

Example 28: (1S,3S)—N3-(5-ethylpyrazolo[1,5-a]pyrimidin-7-yl)cyclopentane-1,3-diamine (28)

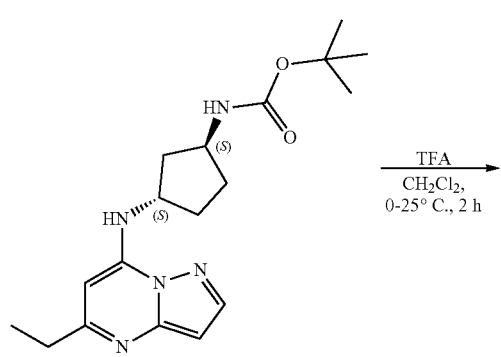

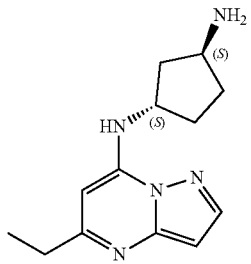

To a stirred solution of tert-butyl N-[(1S,3S)-3-[(5-ethylpyrazolo[1,5-a]pyrimidin-7-yl)amino]cyclopentyl]carbamate (64.0 mg, 0.1900 mmol) in DCM (3.7054 mL) at 0° C. was added trifluoroacetic acid (0.35 mL, 4.63 mmol). The reaction was allowed to warm to room temperature and continuously stirred over 2 hours, whereupon LC-MS revealed reaction complete. The reaction was directly concentrated, washed with pentane and dried to yield (1S,3S)—N3-(5-ethylpyrazolo[1,5-a]pyrimidin-7-yl)cyclopentane-1,3-diamine (17 mg, 0.0693 mmol, 37.403% yield) (28). The reaction mixture was monitored by TLC (100% ethyl acetate; Product Rf=0.1, SM Rf=0.8).

Example 29: N-cyclohexyl-5-isopropyl-pyrazolo[1,5-a]pyrimidin-7-amine (29)

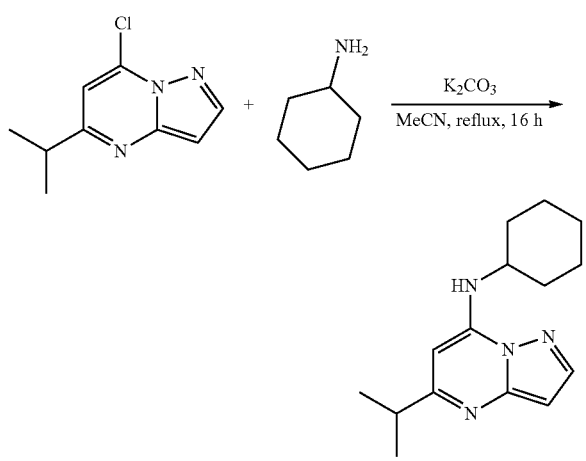

A stirred solution 7-chloro-5-isopropyl-pyrazolo[1,5-a]pyrimidine (100.0 mg, 0.4800 mmol), cyclohexanamine (56.76 mg, 0.5700 mmol) and K$_2$CO$_3$ (197.44 mg, 1.43 mmol) in MeCN (10 mL) was heated to reflux for 16 h. The reaction mixture was monitored by TLC (20% ethyl acetate in hexanes; Product Rf=0.3, SM Rf=0.6). Upon completion, the reaction mixture was concentrated under reduced pressure. Water was then added (50 ml) and extracted with ethyl acetate (20 ml×2). The combined organic layers were combined, dried using anhydrous Na$_2$SO$_4$, filtered, concentrated and purified via column chromatography (20% ethyl acetate in hexanes) to give N-cyclohexyl-5-isopropyl-pyrazolo[1,5-a]pyrimidin-7-amine (110 mg, 0.4216 mmol, 88.399% yield) (29) as an off-white solid.

Example 30: 5-isopropyl-N-[(3R)-tetrahydrofuran-3-yl]pyrazolo[1,5-a]pyrimidin-7-amine (30)

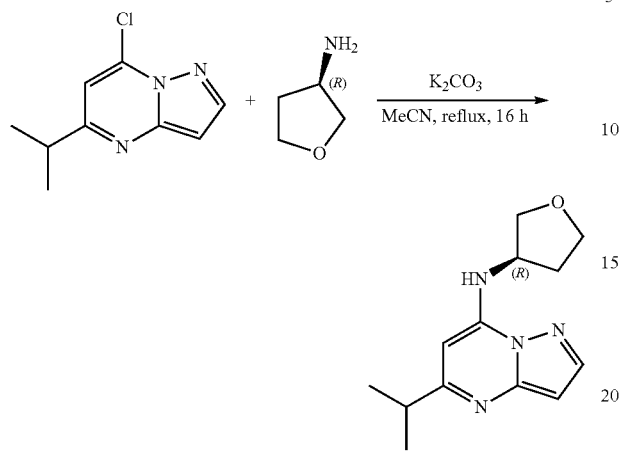

A stirred solution 7-chloro-5-isopropyl-pyrazolo[1,5-a]pyrimidine (100.0 mg, 0.4800 mmol), (3R)-tetrahydrofuran-3-amine (49.86 mg, 0.5700 mmol) and K₂CO₃ (197.44 mg, 1.43 mmol) in MeCN (10 mL) was heated to reflux for 16 h. The reaction mixture was concentrated under reduced pressure, then water was added (50 ml) and extracted with ethyl acetate (20 ml×2). The combined organic layers were dried under anhydrous Na₂SO₄ and concentrated. The crude was purified via column chromatography (20% ethyl acetate in hexane) to give 5-isopropyl-N-[(3R)-tetrahydrofuran-3-yl]pyrazolo[1,5-a]pyrimidin-7-amine (50 mg, 0.2016 mmol, 42.275% yield) (30) as a colourless, thick liquid.

Example 31: N-cyclobutyl-5-isopropyl-pyrazolo[1,5-a]pyrimidin-7-amine (31)

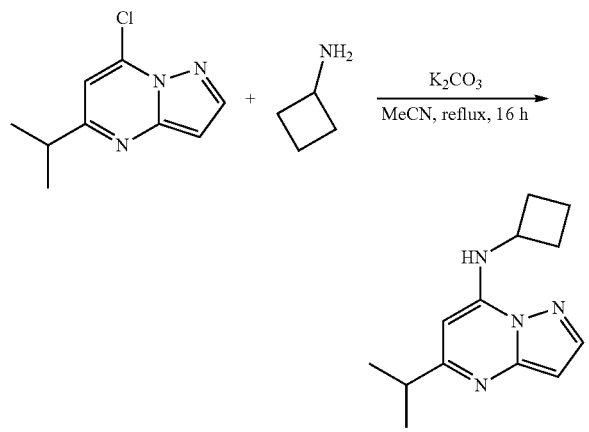

To a stirred solution 7-chloro-5-isopropyl-pyrazolo[1,5-a]pyrimidine (100.0 mg, 0.4800 mmol), cyclobutanamine (40.7 mg, 0.5700 mmol) and K₂CO₃ (197.44 mg, 1.43 mmol) in MeCN (10 mL) were heated to reflux for 16 h. The reaction mixture was concentrated under reduced pressure, then was added water (50 ml) and extracted with ethyl acetate (20 ml×2). The combined organic layers were dried under anhydrous Na₂SO₄. The crude was purified via column chromatography (20% ethyl acetate in hexane) to give N-cyclobutyl-5-isopropyl-pyrazolo[1,5-a]pyrimidin-7-amine (50 mg, 0.2135 mmol, 44.77% yield) (31) as an off-white solid

Example 32: [(1R,3R)-3-[(5-cyclopropylpyrazolo[1,5-a]pyrimidin-7-yl)amino]cyclopentyl]ammonium; 2,2,2-trifluoroacetate (32)

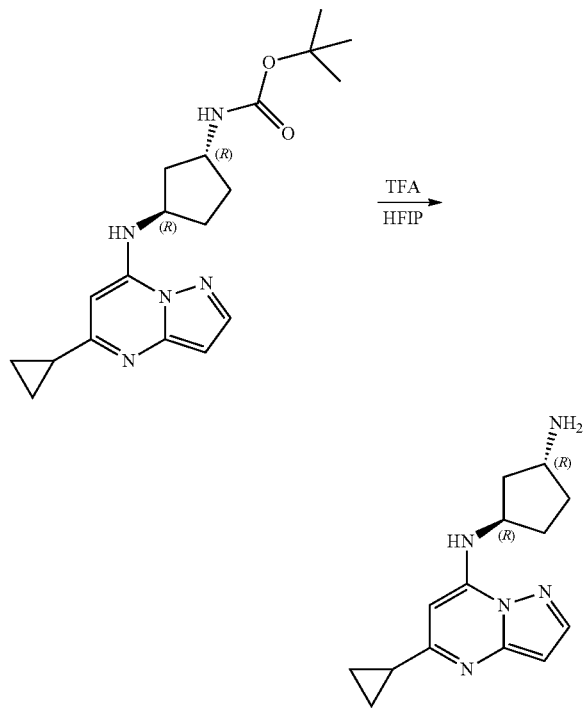

To a stirred solution of tert-butyl N-[(1R,3R)-3-[(5-cyclopropylpyrazolo[1,5-a]pyrimidin-7-yl)amino]cyclopentyl]carbamate (110.0 mg, 0.3100 mmol) in HFIP (51.71 mg, 0.3100 mmol), tert-butyl N-[(1R,3R)-3-[(5-cyclopropylpyrazolo[1,5-a]pyrimidin-7-yl)amino]cyclopentyl]carbamate (110.0 mg, 0.3100 mmol) and trifluoroacetic acid (0.12 mL, 1.54 mmol) were added and stirred at room temperature for 2 h. The reaction mixture was concentrated and the resultant solid was triturated with ether to give [(1R,3R)-3-[(5-cyclopropylpyrazolo[1,5-a]pyrimidin-7-yl)amino]cyclopentyl]ammonium; 2,2,2-trifluoroacetate (58.37 mg, 0.1572 mmol, 51.076% yield) as light brown amorphous solid. The reaction mixture was monitored by TLC (100% ethyl acetate; Product Rf=0.1, SM Rf=0.8).

Representative Synthetic Scheme for Compounds 33 and 34:

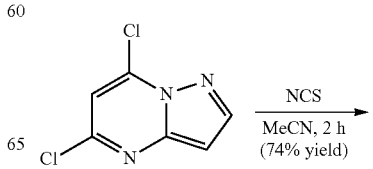

Example 33b

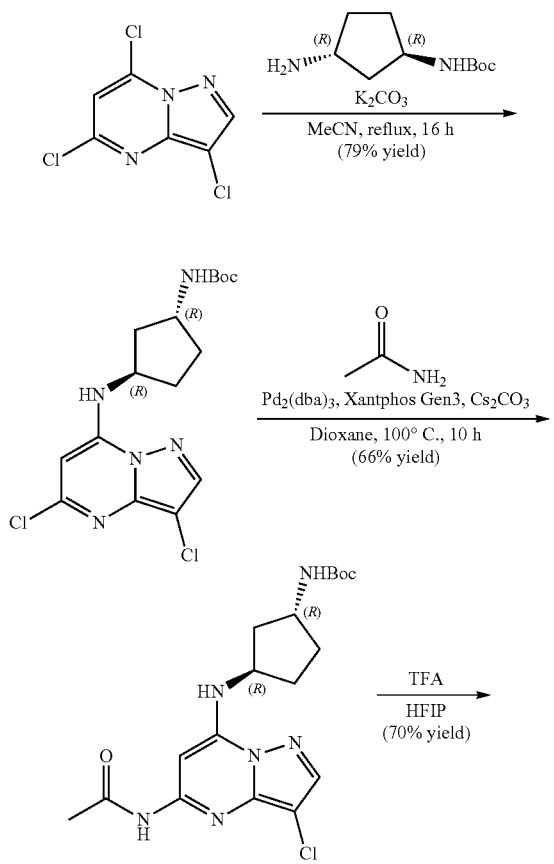

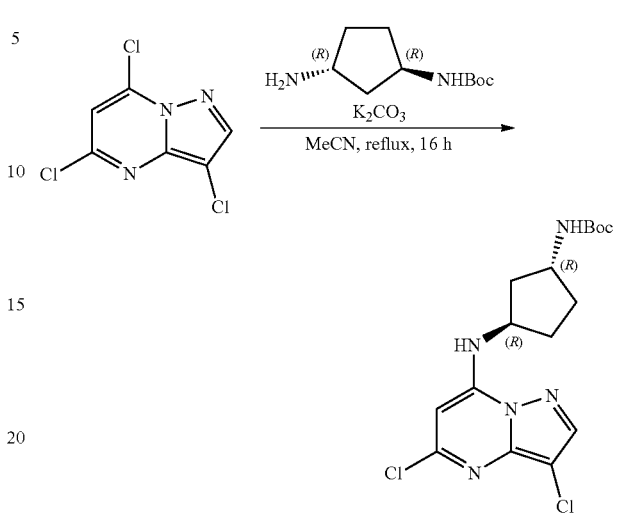

A stirred solution 3,5,7-trichloropyrazolo[1,5-a]pyrimidine (0.4 g, 1.8 mmol), tert-butyl N-[(1R,3R)-3-aminocyclopentyl]carbamate (0.4 g, 1.98 mmol) and K₂CO₃ (0.74 g, 5.39 mmol) in MeCN (20 mL) was heated to reflux for 16 h. The reaction mixture was filtered, concentrated, and purified via column chromatography (30% ethyl acetate in hexanes) to give tert-butyl N-[(1R,3R)-3-[(3,5-dichloropyrazolo[1,5-a]pyrimidin-7-yl)amino]cyclopentyl]carbamate (0.5500 g, 1.4238 mmol, 79.187% yield) as an off-white solid. The reaction mixture was monitored by TLC (40% ethyl acetate in hexanes; Product Rf=0.5, SM Rf=0.8).

Example 33c

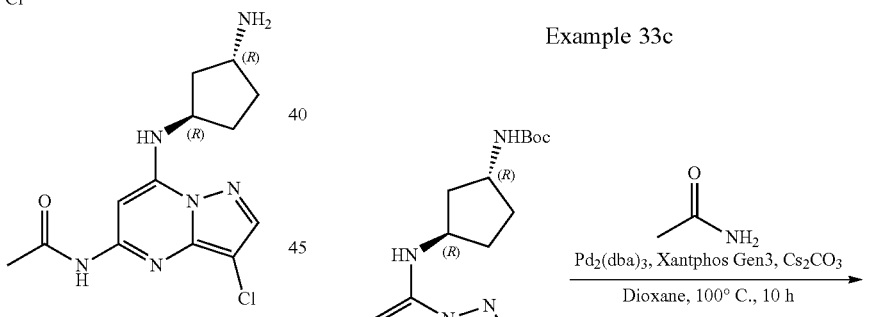

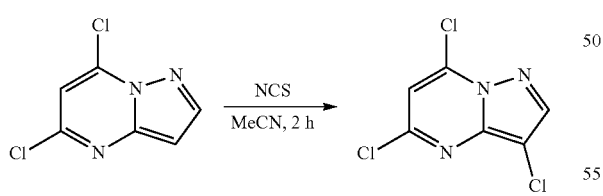

Example 33a

To a solution 5,7-dichloropyrazolo[1,5-a]pyrimidine (200.0 mg, 1.06 mmol) in MeCN (5 mL) was added N-chlorosuccinimide (149.15 mg, 1.12 mmol) at 0° C. The resulting mixture was stirred at room temperature for 2 h. The reaction mixture was concentrated under reduced pressure, purified via column chromatography to give 3,5,7-trichloropyrazolo[1,5-a]pyrimidine (175 mg, 0.7867 mmol, 73.95% yield) as a light yellow solid. The reaction mixture was monitored by TLC (20% ethyl acetate in hexanes; Product Rf=0.6, SM Rf=0.5).

A stirred solution tert-butyl N-[(1R,3R)-3-[(3,5-dichloropyrazolo[1,5-a]pyrimidin-7-yl)amino]cyclopentyl]carbamate (100.0 mg, 0.2600 mmol), acetamide (22.94 mg, 0.3900 mmol), Cs₂CO₃ (252.41 mg, 0.7800 mmol), Pd₂(dba)₃ (23.71 mg, 0.0300 mmol) and Xantphos (43.83 mg, 0.0500 mmol) in dioxane (5 mL) were heated at 100° C. in a sealed tube for 10 h. The reaction mixture was filtered through a pad of celite, concentrated under reduced pressure and purified by column chromatography to give tert-butyl N-[(1R,3R)-3-[(5-acetamido-3-chloro-pyrazolo[1,5-a]pyrimidin-7-yl)amino]cyclopentyl]carbamate (70 mg, 0.1712 mmol, 66.131% yield) as a brown liquid. The reaction mixture was monitored by TLC (30% ethyl acetate in hexanes; Product Rf=0.4, SM Rf=0.6).

Example 33: [(1R,3R)-3-[(5-acetamido-3-chloro-pyrazolo[1,5-a]pyrimidin-7-yl)amino]cyclopentyl]ammonium; 2,2,2-trifluoroacetate (33)

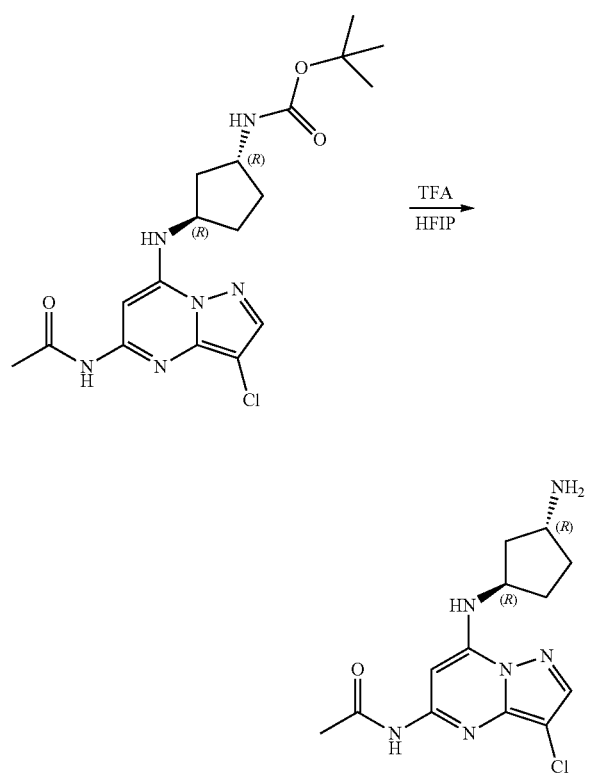

To a stirred solution of tert-butyl N-[(1R,3R)-3-[(5-acetamido-3-chloro-pyrazolo[1,5-a]pyrimidin-7-yl)amino]cyclopentyl]carbamate (65.0 mg, 0.1600 mmol) in HFIP (1.1 mL, 0.1600 mmol), trifluoracetic acid (0.06 mL, 0.7900 mmol) was added and stirred at room temperature for 2 h. The reaction mixture was concentrated and the resultant solid was triturated with ether to give [(1R,3R)-3-[(5-acetamido-3-chloro-pyrazolo[1,5-a]pyrimidin-7-yl)amino]cyclopentyl]ammonium; 2,2,2-trifluoroacetate (47.21 mg, 0.1117 mmol, 70.241% yield) (33) as an off-white amorphous solid. The reaction mixture was monitored by TLC (100% ethyl acetate; Product Rf=0.1, SM Rf=0.8).

Example 34: [(1R,3R)-3-[(5-acetamidopyrazolo[1,5-a]pyrimidin-7-yl)amino]cyclopentyl]ammonium; 2,2,2-trifluoroacetate (34)

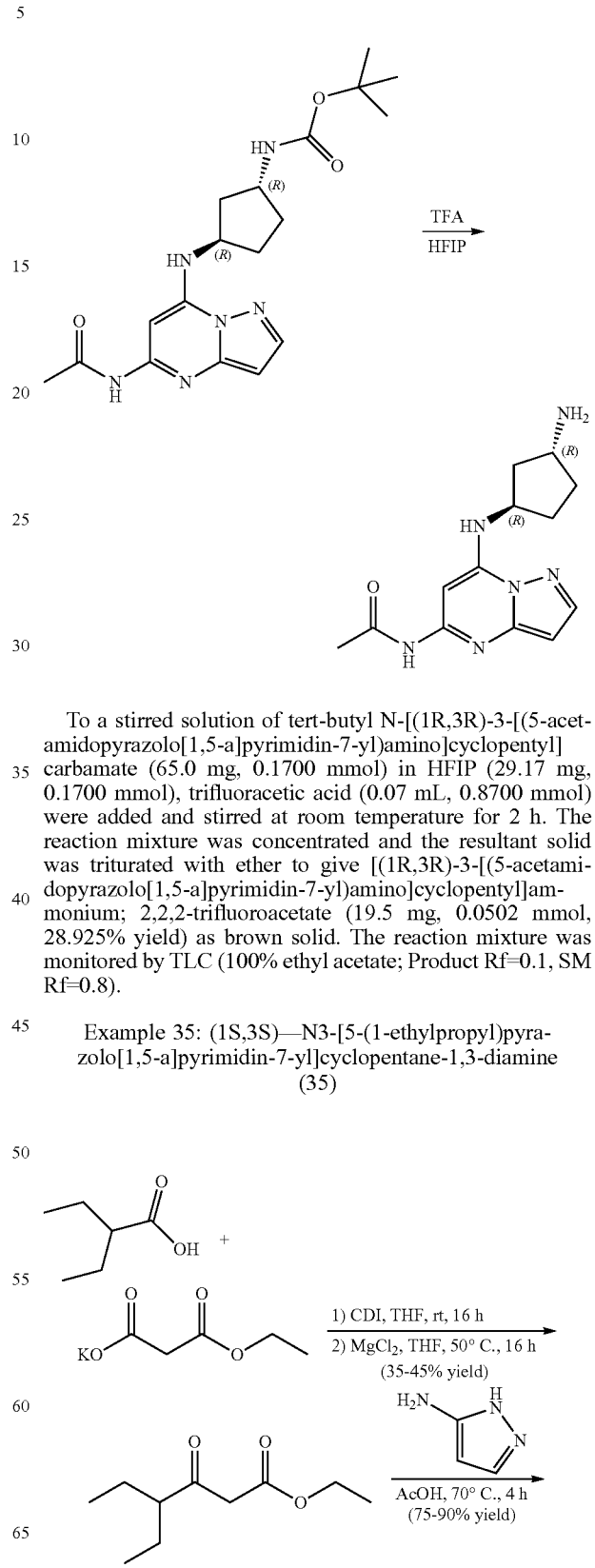

To a stirred solution of tert-butyl N-[(1R,3R)-3-[(5-acetamidopyrazolo[1,5-a]pyrimidin-7-yl)amino]cyclopentyl]carbamate (65.0 mg, 0.1700 mmol) in HFIP (29.17 mg, 0.1700 mmol), trifluoracetic acid (0.07 mL, 0.8700 mmol) were added and stirred at room temperature for 2 h. The reaction mixture was concentrated and the resultant solid was triturated with ether to give [(1R,3R)-3-[(5-acetamidopyrazolo[1,5-a]pyrimidin-7-yl)amino]cyclopentyl]ammonium; 2,2,2-trifluoroacetate (19.5 mg, 0.0502 mmol, 28.925% yield) as brown solid. The reaction mixture was monitored by TLC (100% ethyl acetate; Product Rf=0.1, SM Rf=0.8).

Example 35: (1S,3S)—N3-[5-(1-ethylpropyl)pyrazolo[1,5-a]pyrimidin-7-yl]cyclopentane-1,3-diamine (35)

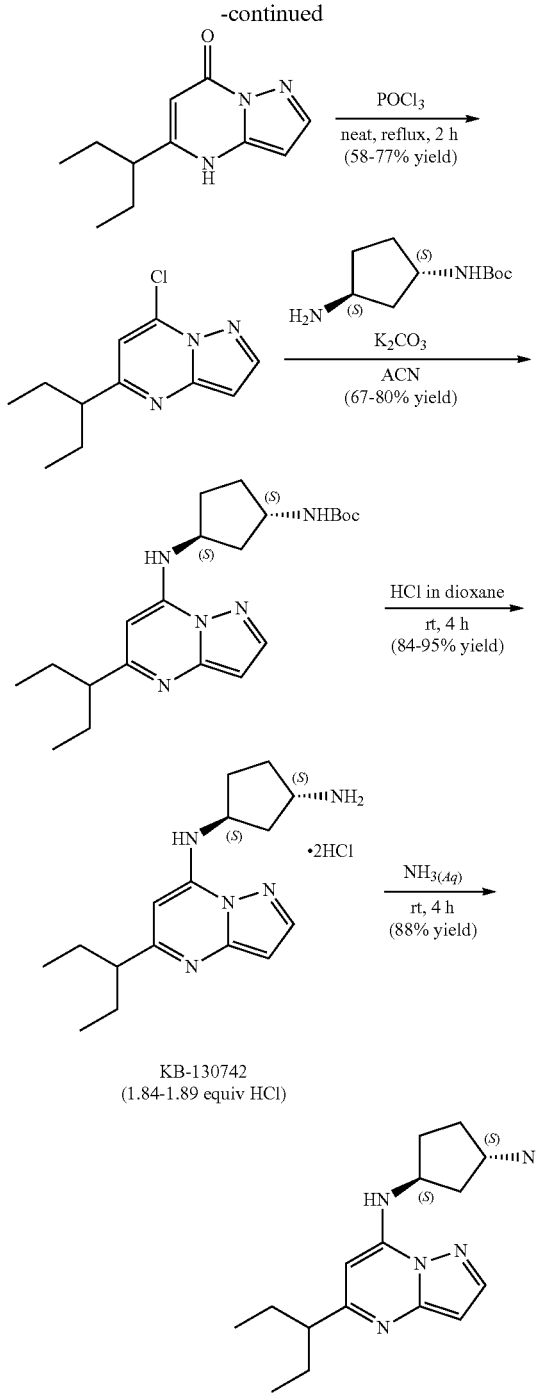

KB-130742
(1.84-1.89 equiv HCl)

↓

KB-130742
(free-base)

Step 1

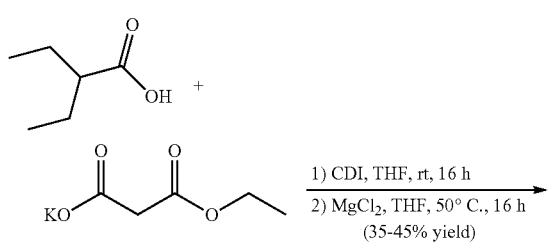

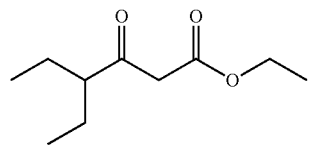

2-Ethylbutanoic acid (7.5 g, 64.57 mmol) was dissolved in THF (150 mL) and cooled to 0° C. Within 20 min CDI (16.23 g, 100.08 mmol) was added portion-wise. The reaction warmed to room temp (rt) and the mixture was stirred at rt overnight (Solution A). In another flask $MgCl_2$ (6.14 g, 64.57 mmol) and potassium 3-ethoxy-3-oxo-propanoate (17 g, 100.1 mmol) were mixed with THF (150 mL) and stirred under argon overnight at 50° C. The resultant white suspension was cooled to rt and solution A was added dropwise over 10 min and the reaction mixture (RM) was stirred for 16 h at room temperature. After several minutes a sticky, amorphous solid appeared whereupon after several hours the reaction mixture became homogenous in appearance. The RM was concentrated to about a third, taken up in half sat. potassium bisulphate solution and extracted twice with ethyl acetate. The organic layers were subsequently washed with a sat. sodium bicarbonate solution, combined, dried over anhydrous sodium sulfate, filtered and evaporated. Purification by column chromatography gave ethyl 4-ethyl-3-oxo-hexanoate (4.3 g, 23.087 mmol, 35.8% yield) as a transparent liquid. The RM was monitored by TLC (10% EA in Hex, Product Rf=0.6, SM Rf=0.1).

Step 2

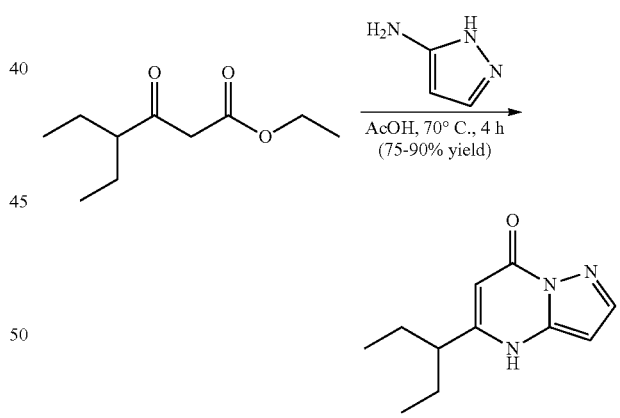

To a suspension of ethyl 4-ethyl-3-oxo-hexanoate (4.4 g, 23.62 mmol) in acetic acid (11 mL) at 70° C. was added 1H-pyrazol-5-amine (4.71 g, 56.7 mmol) in two portions (the second portion was added after 2 hours of stirring the first portion) over a 4 hour period. Upon consumption of SM as indicated by TLC, the reaction was cooled to rt and the solvent was evaporated in a rotary evaporator. The residue was treated with ethyl acetate and filtered to give 5-(1-ethylpropyl)-4H-pyrazolo[1,5-a]pyrimidin-7-one (3.7 g, 17.7 mmol, 74.9% yield) as an off-white solid. The reaction mixture was monitored by TLC (5% MeOH in DCM, Product Rf=0.3, SM Rf=0.8).

Step 3

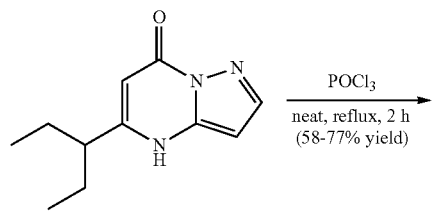

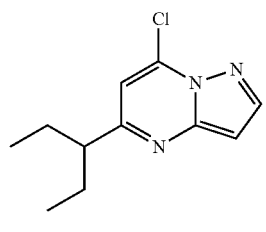

A stirred solution of 5-(1-ethylpropyl)-4H-pyrazolo[1,5-a]pyrimidin-7-one (3.7 g, 18.03 mmol) in POCl₃ (33.7 mL, 360.52 mmol) was heated to reflux for 4 hours. The reaction mixture was cooled to room temperature, excess reagent was evaporated in a rotary evaporator, and the residue was treated with ice-water. The chlorinated product was extracted from aqueous mixture by DCM. The organic layer was separated, dried over anhydrous Na₂SO₄, filtered and purified by column chromatography to give 7-chloro-5-(1-ethylpropyl)pyrazolo[1,5-a]pyrimidine (3.1 g, 13.9 mmol, 76.9% yield) as a light yellow liquid. The reaction mixture was monitored by TLC (20% EA in Hex, Product Rf=0.6, SM Rf=0.1).

Step 4

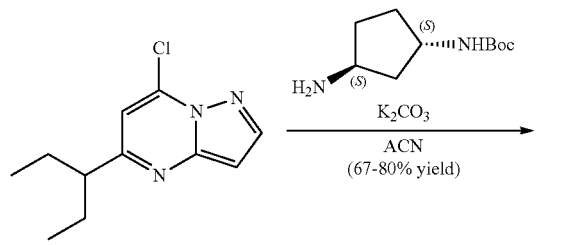

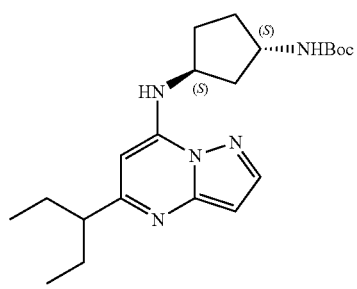

To a stirred solution 7-chloro-5-(1-ethylpropyl)pyrazolo [1,5-a]pyrimidine (2.3 g, 10.28 mmol), tert-Butyl ((1S,3S)-3-aminocyclopentyl)carbamate (2.27 g, 11.31 mmol) and K₂CO₃ (4.26 g, 30.84 mmol) in MeCN (20 mL) were heated to reflux for 16 hours. The reaction mixture was filtered, concentrated under reduced pressure and purified by column chromatography, eluent 30% EA in hexane to give tert-butyl N-[(1S,3S)-3-[[5-(1-ethylpropyl)pyrazolo[1,5-a]pyrimidin-7-yl]amino]cyclopentyl]carbamate (4.5 g, 11.6 mmol, 112.8% yield) as an off-white solid. The reaction mixture was monitored by TLC (40% EA in Hex, Product Rf=0.5, SM Rf=0.7).

Step 5

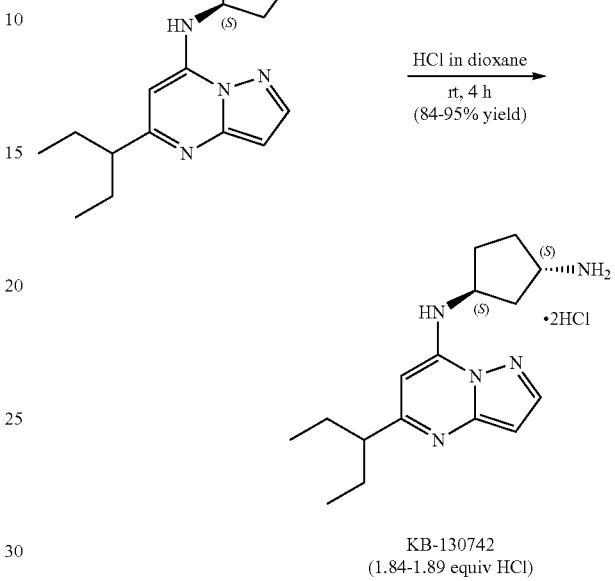

KB-130742
(1.84-1.89 equiv HCl)

To tert-butyl N-[(1S,3S)-3-[[5-(1-ethylpropyl)pyrazolo[1,5-a]pyrimidin-7-yl]amino]cyclopentyl]carbamate (1.0 g, 2.58 mmol) in 1,4-Dioxane (0.2 mL), 4 M HCl in Dioxane (3.22 mL, 12.9 mmol) was added and stirred at room temperature for 4 hours. The reaction mixture was evaporated in vacuo, triturated with pentane and lyophilized from MeCN:H2O to give [(1S,3S)-3-[[5-(1-ethylpropyl)pyrazolo[1,5-a]pyrimidin-4-ium-7-yl]amino]cyclopentyl]ammonium dichloride (0.9 g, 2.5 mmol, 96.8% yield) as a pale-yellow sticky solid. The reaction mixture was monitored by TLC (100% EA, Product Rf=0.1, SM Rf=0.8). 1H NMR (400 MHz, DMSO-d6) δ 15.00 (s, 1H), 9.93-9.86 (m, 1H), 8.51 (s, 3H), 8.30 (s, 1H), 6.84 (s, 1H), 6.58 (s, 1H), 4.95 (q, J=7.8 Hz, 1H), 3.77-3.66 (m, 1H), 2.84-2.71 (m, 1H), 2.29-2.05 (m, 4H), 1.94-1.63 (m, 6H), 0.81 (t, J=7.4 Hz, 6H). LC-MS (m/z 287.21, found 288.0 [M+H+])

Step 6

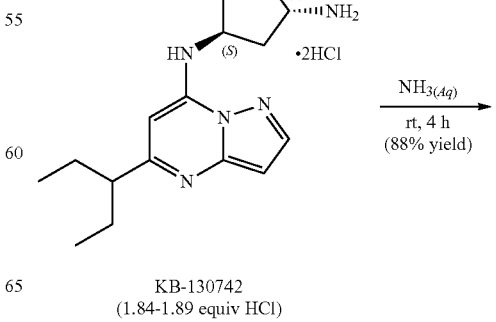

KB-130742
(1.84-1.89 equiv HCl)

-continued

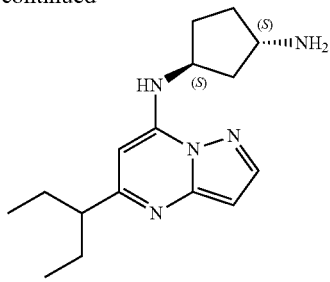

KB-130742
(free base)

To [(1S,3S)-3-[[5-(1-ethylpropyl)pyrazolo[1,5-a]pyrimidin-4-ium-7-yl]amino]cyclopentyl]ammonium-dichloride (0.2 g, 0.5600 mmol) in aq. NH₃ (4.0 mL, 0.56 mmol) was added and stirred at room temperature for 4 hours. The reaction mixture was evaporated in vacuo, triturated with pentane and lyophilized from MeCN:H2O to give (1S,3S)—N3-[5-(1-ethylpropyl)pyrazolo[1,5-a]pyrimidin-7-yl]cyclopentane-1,3-diamine (140 mg, 0.49 mmol, 87.8% yield) as a pale-yellow sticky solid. The reaction mixture was monitored by TLC (100% EA, Product Rf=0.1, SM Rf=0.8). 1H NMR (400 MHz, DMSO-d6) δ 7.95 (d, J=2.2 Hz, 1H), 6.86 (s, 1H), 6.29 (d, J=2.2 Hz, 1H), 5.95 (s, 1H), 4.31-4.19 (m, 1H), 3.57-3.44 (m, 1H), 2.52-2.44 (m, 1H), 2.36-2.22 (m, 1H), 2.09-1.79 (m, 3H), 1.80-1.59 (m, 5H), 1.58-1.24 (m, 3H), 0.83 (t, J=7.4 Hz, 6H). LC-MS (m/z 287.21, found 288.5 [M+H+]).

TABLE

Compound Data

| Compound | MF | Mass | [M + X] | Mass Found |
|---|---|---|---|---|
| 1 | C12H16N4 | 216.1375 | [M + H] | 216.8 |
| 2 | C14H20N4 | 244.1688 | [M + H] | 244.7 |
| 3 | C15H22N4 | 258.1844 | [M + H] | 258.7 |
| 4 | C13H19N5 | 245.164 | [M + H] | 246 |
| 5 | C16H22N4 | 270.1844 | [M + H] | 270.7 |
| 6 | C15H23N5 | 273.1953 | [M + H] | 274.2 |
| 7 | C16H25N5 | 287.211 | [M + H] | 287.7 |
| 8 | C17H25N5 | 299.211 | [M + H] | 299.8 |
| 9 | C16H23N5 | 285.1953 | [M + H] | 285.8 |
| 10 | C12H17N5 | 231.1484 | [M + H] | 232.2 |
| 11 | C11H15N5 | 217.1327 | [M + H] | 218.3 |
| 12 | C12H17N5 | 231.1484 | [M + H] | 232.3 |
| 13 | C14H21N5 | 259.1797 | [M + H] | 259.8 |
| 14 | C15H23N5 | 273.1953 | [M + H] | 273.9 |
| 15 | C16H23N5 | 285.1953 | [M + H] | 286.4 |
| 16 | C14H21N5 | 259.1797 | [M + H] | 259.8 |
| 17 | C14H21N5 | 259.1797 | [M + H] | 260.2 |
| 18 | C15H23N5 | 273.1953 | [M + H] | 273.8 |
| 19 | C14H21N5 | 259.1797 | [M + H] | 260 |
| 20 | C15H21N5 | 271.1797 | [M + H] | 372 |
| 21 | C13H19N5 | 245.164 | [M + H] | 245.9 |
| 22 | C15H23N5 | 273.1953 | [M + H] | 274.3 |
| 23 | C16H23N5 | 285.1953 | [M + H] | 286.2 |
| 24 | C12H17N5 | 231.1484 | [M + H] | 231.7 |
| 25 | C13H19N5 | 245.164 | [M + H] | 246.2 |
| 26 | C14H21N5 | 259.1797 | [M + H] | 260.2 |
| 27 | C14H21N5 | 259.1797 | [M + H] | 260.2 |
| 28 | C13H19N5 | 245.164 | [M + H] | 246.2 |
| 29 | C15H22N4 | 258.1844 | [M + H] | 259 |
| 30 | C13H18N4O | 246.1481 | [M + H] | 246.9 |
| 31 | C13H18N4 | 230.1531 | [M + H] | 231 |
| 32 | C14H19N5 | 257.164 | [M + H] | 257.7 |
| 33 | C13H17ClN6O | 308.1152 | [M + H] | 308.9 |
| 34 | C13H18N6O | 274.1542 | [M + H] | 275.3 |
| 35 | C16H25N5 | 287.211 | [M + H] | 288 |
| 36 | C13H17ClN6O | 308.1152 | [M + H] | 308.9 |
| 37 | C13H18N6O | 274.1542 | [M + H] | 275.3 |
| 38 | C15H23N5 | 273.1953 | [M + H] | 274.4 |
| 39 | C15H23N5 | 273.1953 | [M + H] | 273.7 |
| 40 | C14H20ClN5 | 293.1407 | [M + H] | 293.8 |
| 41 | C13H19N5 | 245.164 | [M + H] | 245.9 |
| 42 | C15H21N5 | 271.18 | [M + H] | 271.9 |
| 43 | C14H19N5 | 257.164 | [M + H] | 257.7 |
| 44 | C14H21N5 | 259.1797 | [M + H] | 260.1 |
| 45 | C14H20ClN5 | 293.1407 | [M + H] | 293.8 |
| 46 | C15H21N5O | 287.1746 | [M + H] | 288.3 |
| 47 | C13H19N5 | 245.164 | [M + H] | 246.4 |
| 48 | C14H21N5 | 259.1797 | [M + H] | 260 |
| 49 | C18H27N5O2 | 345.2165 | [M + H] | 346.3 |
| 50 | C22H27N5O2 | 393.2165 | [M + H] | 394.5 |
| 51 | C15H19N5O | 285.159 | [M + H] | 285.8 |
| 52 | C16H23N5O | 301.1903 | [M + H] | 301.8 |
| 53 | C15H23N5 | 273.1953 | [M + H] | 273.9 |
| 54 | C16H23N5O2 | 317.1852 | [M + H] | 318 |
| 55 | C16H23N5O | 301.1903 | [M + H] | 301.8 |
| 56 | C16H24N6O | 316.2012 | [M + H] | 317 |
| 57 | C22H29N7O | 407.2434 | [M + H] | 408 |
| 58 | C21H28N6 | 364.2375 | [M + H] | 265.4 |
| 59 | C17H27N5O | 317.2216 | [M + H] | 318.1 |
| 60 | C15H22N6O2 | 318.1804 | [M + H] | 319 |
| 61 | C18H19N5O2 | 337.1539 | [M + H] | 338 |
| 62 | C20H33N5O | 359.2685 | [M + H] | 360 |
| 63 | C17H24N8 | 340.2124 | [M + H] | 340.9 |
| 64 | C15H20N6 | 284.1749 | [M + H] | 285.2 |
| 65 | C16H24N6 | 300.2062 | [M + H] | 301 |
| 66 | C15H23N7 | 301.2015 | [M + H] | 302 |
| 67 | C22H26ClN5O2 | 427.1775 | [M + H] | 428.2 |
| 68 | C18H26ClN5O2 | 379.1775 | [M + H] | 380.2 |
| 69 | C21H21N5 | 343.1797 | [M + H] | 344.5 |
| 70 | C19H23N5O | 337.1903 | [M + H] | 338.3 |
| 71 | C21H22N6 | 358.1906 | [M + H] | 359.3 |
| 72 | C15H22N6O | 302.1855 | [M + H] | 303.2 |
| 73 | C18H21N5 | 307.1797 | [M + H] | 308.3 |
| 74 | C18H20ClN5O | 357.1356 | [M + H] | 357.8 |
| 75 | C17H18ClN5 | 327.1251 | [M + H] | 327.8 |
| 76 | C15H22ClN5 | 307.1564 | [M + H] | 307.8 |
| 77 | C12H17N5 | 247.1433 | [M + H] | 248.1 |
| 78 | C16H19N7O | 325.1651 | [M + H] | 326.3 |
| 79 | C15H24N6 | 288.2062 | [M + H] | 288.9 |
| 80 | C21H22N6 | 358.1906 | [M + H] | 358.9 |
| 81 | C21H21N5 | 343.1797 | [M + H] | 344.1 |
| 82 | C17H17Cl2N5 | 361.0861 | [M + H] | 362.3 |
| 83 | C15H19N7 | 297.1702 | [M + H] | 298.2 |
| 84 | C22H25N5O2 | 391.2008 | [M + H] | 392 |
| 85 | C19H29N5O2 | 359.2321 | [M + H] | 360.3 |
| 86 | C15H24N6 | 288.2062 | [M + H] | 289.3 |
| 87 | C23H29N5O2 | 407.2321 | [M + H] | 408.4 |
| 88 | C14H22N6O | 290.1855 | [M + H] | 291.2 |
| 89 | C16H21N5O2 | 315.1695 | [M + H] | 316.3 |
| 90 | C14H22N6O | 290.1855 | [M + H] | 291.5 |
| 91 | C13H19N5O | 261.159 | [M + H] | 262.3 |
| 92 | C14H22N6 | 274.1906 | [M + H] | 275.2 |
| 93 | C16H25N5 | 287.211 | [M + H] | 288.3 |
| 94 | C18H21N5O | 323.1746 | [M + H] | 324 |
| 95 | C18H21N5O | 323.1746 | [M + H] | 324.2 |
| 96 | C18H21N5O | 323.1746 | [M + H] | 324.4 |
| 97 | C19H24N6 | 336.2062 | [M + H] | 337.4 |
| 98 | C13H20N6 | 260.1749 | [M + H] | 261.3 |
| 99 | C16H25N7 | 315.2171 | [M + H] | 316.4 |
| 100 | C17H20N6 | 308.1749 | [M + H] | 309.1 |
| 101 | C17H20N6O | 324.1699 | [M + H] | 325.1 |
| 102 | C16H23N7O | 329.1964 | [M + H] | 330.3 |
| 103 | C16H19N7 | 309.1702 | [M + H] | 310.3 |
| 104 | C18H18ClN5O2 | 371.1149 | [M + H] | 372.3 |
| 105 | C19H23N5 | 321.1953 | [M + H] | 322.4 |
| 106 | C16H24ClN5 | 321.172 | [M + H] | 322.4 |
| 107 | C17H18FN5 | 311.1546 | [M + H] | 312.1 |
| 108 | C20H25N5 | 335.211 | [M + H] | 336.2 |
| 109 | C17H23N5 | 297.1953 | [M + H] | 298.2 |
| 110 | C16H21N5O | 299.1746 | [M + H] | 300.2 |
| 111 | C17H18FN5 | 311.1546 | [M + H] | 312.1 |

TABLE-continued

Compound Data

| Compound | MF | Mass | [M + X] | Mass Found |
|---|---|---|---|---|
| 112 | C16H21N5O | 299.1746 | [M + H] | 300.2 |
| 113 | C21H24N6 | 360.2062 | [M + H] | 361.3 |
| 114 | C20H23N5 | 333.1953 | [M + H] | 334.3 |
| 115 | C17H25N5 | 299.211 | [M + H] | 300.1 |
| 116 | C15H19N7 | 297.1702 | [M + H] | 298.2 |
| 117 | C16H23N5 | 285.1953 | [M + H] | 286.2 |
| 118 | C19H19N5 | 317.164 | [M + H] | 318 |
| 119 | C19H25N5 | 323.211 | [M + H] | 324.1 |
| 120 | C16H19N5 | 281.164 | [M + H] | 282.1 |
| 121 | C20H25N5 | 335.211 | [M + H] | 336.1 |
| 122 | C18H27N5 | 313.2266 | [M + H] | 314.1 |
| 123 | C15H21N5 | 271.1797 | [M + H] | 272.1 |
| 124 | C15H21N5O | 287.1746 | [M + H] | 288.3 |
| 125 | C17H23F2N5 | 335.1922 | [M + H] | 336.1 |
| 126 | C15H19N5O | 285.159 | [M + H] | 286 |
| 127 | C13H17C1N6O | 308.1152 | [M + H] | 308.9 |
| 128 | C13H18N6O | 274.1542 | [M + H] | 275.3 |
| 129 | C15H23N5 | 273.1953 | [M + H] | 274.4 |
| 130 | C15H23N5 | 273.1953 | [M + H] | 273.7 |
| 131 | C14H20C1N5 | 293.1407 | [M + H] | 293.8 |
| 132 | C13H19N5 | 245.164 | [M + H] | 245.9 |
| 133 | C15H21N5 | 271.18 | [M + H] | 271.9 |
| 134 | C14H19N5 | 257.164 | [M + H] | 257.7 |
| 135 | C14H21N5 | 259.1797 | [M + H] | 260.1 |
| 136 | C14H20C1N5 | 293.1407 | [M + H] | 293.8 |
| 137 | C15H21N5O | 287.1746 | [M + H] | 288.3 |
| 138 | C13H19N5 | 245.164 | [M + H] | 246.4 |
| 139 | C14H21N5 | 259.1797 | [M + H] | 260 |
| 140 | C18H27N5O2 | 345.2165 | [M + H] | 346.3 |
| 141 | C22H27N5O2 | 393.2165 | [M + H] | 394.5 |
| 142 | C15H19N5O | 285.159 | [M + H] | 285.8 |
| 143 | C16H23N5O | 301.1903 | [M + H] | 301.8 |
| 144 | C15H23N5 | 273.1953 | [M + H] | 273.9 |
| 145 | C16H23N5O2 | 317.1852 | [M + H] | 318 |
| 146 | C16H23N5O | 301.1903 | [M + H] | 301.8 |
| 147 | C16H24N6O | 316.2012 | [M + H] | 317 |
| 148 | C22H29N7O | 407.2434 | [M + H] | 408 |
| 149 | C21H28N6 | 364.2375 | [M + H] | 265.4 |
| 150 | C17H27N5O | 317.2216 | [M + H] | 318.1 |
| 151 | C15H22N6O2 | 318.1804 | [M + H] | 319 |
| 152 | C18H19N5O2 | 337.1539 | [M + H] | 338 |
| 153 | C20H33N5O | 359.2685 | [M + H] | 360 |
| 154 | C17H24N8 | 340.2124 | [M + H] | 340.9 |
| 155 | C15H20N6 | 284.1749 | [M + H] | 285.2 |
| 156 | C16H24N6 | 300.2062 | [M + H] | 301 |
| 157 | C15H23N7 | 301.2015 | [M + H] | 302 |
| 158 | C22H26C1N5O2 | 427.1775 | [M + H] | 428.2 |
| 159 | C18H26C1N5O2 | 379.1775 | [M + H] | 380.2 |
| 160 | C21H21N5 | 343.1797 | [M + H] | 344.5 |
| 161 | C19H23N5O | 337.1903 | [M + H] | 338.3 |
| 162 | C21H22N6 | 358.1906 | [M + H] | 359.3 |
| 163 | C15H22N6O | 302.1855 | [M + H] | 303.2 |
| 164 | C18H21N5 | 307.1797 | [M + H] | 308.3 |
| 165 | C18H20C1N5O | 357.1356 | [M + H] | 357.8 |
| 166 | C17H18C1N5 | 327.1251 | [M + H] | 327.8 |
| 167 | C15H22C1N5 | 307.1564 | [M + H] | 307.8 |
| 168 | C12H17N5O | 247.1433 | [M + H] | 248.1 |
| 169 | C16H19N7O | 325.1651 | [M + H] | 326.3 |
| 170 | C15H24N6 | 288.2062 | [M + H] | 288.9 |
| 171 | C21H22N6 | 358.1906 | [M + H] | 358.9 |
| 172 | C21H21N5 | 343.1797 | [M + H] | 344.1 |
| 173 | C17H17C12N5 | 361.0861 | [M + H] | 362.3 |
| 174 | C15H19N7 | 297.1702 | [M + H] | 298.2 |
| 175 | C22H25N5O2 | 391.2008 | [M + H] | 392 |
| 176 | C19H29N5O2 | 359.2321 | [M + H] | 360.3 |
| 177 | C15H24N6 | 288.2062 | [M + H] | 289.3 |
| 178 | C23H29N5O2 | 407.2321 | [M + H] | 408.4 |
| 179 | C14H22N6O | 290.1855 | [M + H] | 291.2 |
| 180 | C16H21N5O2 | 315.1695 | [M + H] | 316.3 |
| 181 | C14H22N6O | 290.1855 | [M + H] | 291.5 |
| 182 | C13H19N5O | 261.1594 | [M + H] | 262.3 |
| 183 | C14H22N6 | 274.1906 | [M + H] | 275.2 |
| 184 | C16H25N5 | 287.211 | [M + H] | 288.3 |
| 185 | C18H21N5O | 323.1746 | [M + H] | 324 |
| 186 | C18H21N5O | 323.1746 | [M + H] | 324.2 |
| 187 | C18H21N5O | 323.1746 | [M + H] | 324.4 |
| 188 | C19H24N6 | 336.2062 | [M + H] | 337.4 |
| 189 | C13H20N6 | 260.1749 | [M + H] | 261.3 |
| 190 | C16H25N7 | 315.2171 | [M + H] | 316.4 |
| 191 | C17H20N6 | 308.1749 | [M + H] | 309.1 |
| 192 | C17H20N6O | 324.1699 | [M + H] | 325.1 |
| 193 | C16H23N7O | 329.1964 | [M + H] | 330.3 |
| 194 | C16H19N7 | 309.1702 | [M + H] | 310.3 |
| 195 | C18H18C1N5O2 | 371.1149 | [M + H] | 372.3 |
| 196 | C19H23N5 | 321.1953 | [M + H] | 322.4 |
| 197 | C16H24C1N5 | 321.172 | [M + H] | 322.4 |
| 198 | C17H18FN5 | 311.1546 | [M + H] | 312.1 |
| 199 | C20H25N5 | 335.211 | [M + H] | 336.2 |
| 200 | C17H23N5 | 297.1953 | [M + H] | 298.2 |
| 201 | C16H21N5O | 299.1746 | [M + H] | 300.2 |
| 202 | C17H18FN5 | 311.1546 | [M + H] | 312.1 |
| 203 | C16H21N5O | 299.1746 | [M + H] | 300.2 |
| 204 | C21H24N6 | 360.2062 | [M + H] | 361.3 |
| 205 | C20H23N5 | 333.1953 | [M + H] | 334.3 |
| 206 | C17H25N5 | 299.211 | [M + H] | 300.1 |
| 207 | C15H19N7 | 297.1702 | [M + H] | 298.2 |
| 208 | C16H23N5 | 285.1953 | [M + H] | 286.2 |

Example 35: CDK9/Cyclin T1 Inhibition

Exemplary compounds of the invention (1-34) were tested for inhibition of CDK9/cyclin T1. Using a radiometric assay (reaction time 60 minutes) the compounds were tested in 10-dose IC50 duplicate mode with a 3-fold serial dilution starting at 10 µM. A control compound (Staurosporine) was tested in 10-dose IC50 mode with 3-fold serial dilution starting at 10 µM. Reactions were carried out at 10 µM ATP. Results for the tested compounds are shown in the Table below. Data was normalized to positive and negative controls and curve fits were executed with GraphPad software and were performed where the enzyme activities at the highest concentration of compounds were less than 65%.

Exemplary compounds of the invention (35-126) were tested for inhibition of CDK9/cyclin T1 kinase. Using a LANCE assay (reaction time 60 minutes), the compounds were tested in 10-dose IC50 duplicate mode with a 3-fold serial dilution starting at 4.3 µM. A control compound (SNS-032) was tested in 10-dose IC50 mode with 3-fold serial dilution starting at 10 µM. Reactions were carried out at 10 µM ATP. Results for the tested compounds are shown in the Table below. Data was normalized to positive and negative controls and curve fits were analyzed with XLFIT5 as % inhibition vs. log [compound concentration] using a 4-parameter logistic model 205. Fit=(A+((B−A)/(1+((C/x)^D)))); Res=(y-fit).

TABLE

Results of cyclin T1 inhibition
Potency grade: A = 1-500 nM; B = 501-1000 nM; C ≥ 1001 nM

| Compound | CDK9/cyclin T1 Potency Grade |
|---|---|
| 1 | C |
| 2 | A |
| 3 | A |
| 4 | B |
| 5 | A |
| 6 | A |
| 7 | A |
| 8 | A |
| 9 | A |
| 10 | C |

TABLE-continued

Results of cyclin T1 inhibition
Potency grade: A = 1-500 nM; B = 501-1000 nM; C ≥ 1001 nM

| Compound | CDK9/cyclin T1 Potency Grade |
| --- | --- |
| 11 | B |
| 12 | B |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | B |
| 25 | B |
| 26 | N/A |
| 27 | N/A |
| 28 | A |
| 29 | A |
| 30 | C |
| 31 | A |
| 32 | A |
| 33 | A |
| 34 | C |
| 35 | A |
| 36 | A |
| 37 | C |
| 38 | N/A |
| 39 | A |
| 40 | A |
| 41 | A |
| 42 | A |
| 43 | A |
| 44 | C |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | B |
| 69 | B |
| 70 | A |
| 71 | A |
| 72 | A |
| 73 | A |
| 74 | A |
| 75 | A |
| 76 | A |
| 77 | B |
| 78 | B |
| 79 | A |
| 80 | A |
| 81 | A |
| 82 | A |
| 83 | A |
| 84 | C |
| 85 | A |
| 86 | A |
| 87 | A |
| 88 | B |
| 89 | C |
| 90 | A |
| 91 | B |
| 92 | C |
| 93 | A |
| 94 | A |
| 95 | A |
| 96 | A |
| 97 | A |
| 98 | A |
| 99 | C |
| 100 | A |
| 101 | A |
| 102 | A |
| 103 | B |
| 104 | A |
| 105 | A |
| 106 | A |
| 107 | A |
| 108 | A |
| 109 | A |
| 110 | B |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | B |
| 125 | A |
| 126 | B |
| 127 | A |
| 128 | C |
| 129 | N/A |
| 130 | A |
| 131 | A |
| 132 | A |
| 133 | A |
| 134 | A |
| 135 | C |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | B |
| 160 | B |

TABLE-continued

Results of cyclin T1 inhibition
Potency grade: A = 1-500 nM; B = 501-1000 nM; C ≥ 1001 nM

| Compound | CDK9/cyclin T1 Potency Grade |
|---|---|
| 161 | A |
| 162 | A |
| 163 | A |
| 164 | A |
| 165 | A |
| 166 | A |
| 167 | A |
| 168 | B |
| 169 | B |
| 170 | A |
| 171 | A |
| 172 | A |
| 173 | A |
| 174 | A |
| 175 | C |
| 176 | A |
| 177 | A |
| 178 | A |
| 179 | B |
| 180 | C |
| 181 | A |
| 182 | B |
| 183 | C |
| 184 | A |
| 185 | A |
| 186 | A |
| 187 | A |
| 188 | A |
| 189 | A |
| 190 | C |
| 191 | A |
| 192 | A |
| 193 | A |
| 194 | B |
| 195 | A |
| 196 | A |
| 197 | A |
| 198 | A |
| 199 | A |
| 200 | A |
| 201 | B |
| 202 | A |
| 203 | A |
| 204 | A |
| 205 | A |
| 206 | A |
| 207 | A |
| 208 | A |
| Staurosporine | A |

The test data shows that the compounds disclosed herein are effective as CDK9 inhibitors and would be suitable candidates for therapy relating to CDK9-mediated disorders.

The contents of all references, pending patent applications and published patents, cited throughout this application are hereby expressly incorporated by reference.

The foregoing embodiments are presented by way of example only. A person of ordinary skill in the relevant field would understand that various modifications may be made without deviating from the spirit and scope of the present invention.

The invention claimed is:

1. A method for modulating cyclin-dependent kinase 9/cyclin T1 activity in a patient, wherein the method comprises administering to the patient in need thereof a therapeutically effective amount of a compound of the following formula:

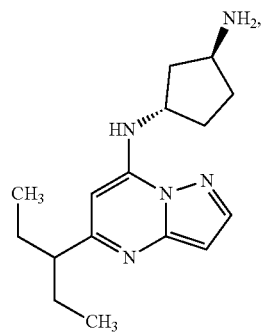 [SMILES: CCC(CC)c1cc(N[C@H]2CC[C@H](N)C2)n2nccc2n1]

or a pharmaceutically acceptable salt thereof.

2. The method of claim 1, wherein the patient has a cyclin-dependent kinase 9 mediated disease selected from the group consisting of acute lymphoblastic leukemia, acute myelogenous leukemia, advanced breast cancer, biphenotypic acute leukemia, chronic lymphocytic leukemia, liver cancer, non-Hodgkin's lymphoma, non-small cell lung cancer, primary peritoneal carcinoma, and relapsed multiple myeloma.

3. The method of claim 1, wherein the patient has a cyclin-dependent kinase 9 mediated disease selected from the group consisting of a cancer caused by aberrant expression of MCL-1, a cancer caused by aberrant expression of MYC, a hematologic malignancy, and a solid tumor.

4. The method of claim 3, wherein the patient has a cancer caused by aberrant expression of MCL-1.

5. The method of claim 3, wherein the patient has a cancer caused by aberrant expression of MYC.

6. The method of claim 1, wherein the pharmaceutically acceptable salt is the dihydrochloride salt.

7. A method for modulating cyclin-dependent kinase 9/cyclin T1 activity in a patient, wherein the method comprises administering to the patient in need thereof a therapeutically effective amount of a pharmaceutical composition comprising a pharmaceutically acceptable carrier and a compound of the following formula:

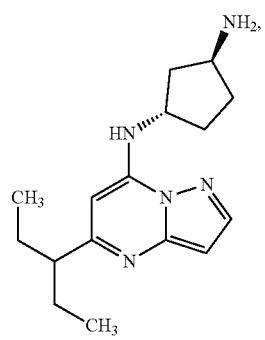 [SMILES: CCC(CC)c1cc(N[C@H]2CC[C@H](N)C2)n2nccc2n1]

or a pharmaceutically acceptable salt thereof.

8. The method of claim 7, wherein the patient has a cyclin-dependent kinase 9 mediated disease selected from the group consisting of acute lymphoblastic leukemia, acute myelogenous leukemia, advanced breast cancer, biphenotypic acute leukemia, chronic lymphocytic leukemia, liver cancer, non-Hodgkin's lymphoma, non-small cell lung cancer, primary peritoneal carcinoma, and relapsed multiple myeloma.

9. The method of claim 7, wherein the patient has a cyclin-dependent kinase 9 mediated disease selected from the group consisting of a cancer caused by aberrant expression of MCL-1, a cancer caused by aberrant expression of MYC, a hematologic malignancy, and a solid tumor.

10. The method of claim 9, wherein the patient has a cancer caused by aberrant expression of MCL-1.

11. The method of claim 9, wherein the patient has a cancer caused by aberrant expression of MYC.

* * * * *